(12) United States Patent
Kuliopulos et al.

(10) Patent No.: US 9,376,499 B2
(45) Date of Patent: Jun. 28, 2016

(54) PAR-1 ACTIVATION BY METALLOPROTEINASE-1 (MMP-1)

(71) Applicant: Tufts Medical Center, Inc., Boston, MA (US)

(72) Inventors: Athan Kuliopulos, Winchester, MA (US); Georgios Koukos, Boston, MA (US)

(73) Assignee: Tufts Medical Center, Inc., Boston, MA (US)

( * ) Notice: Subject to any disclaimer, the term of this patent is extended or adjusted under 35 U.S.C. 154(b) by 73 days.

(21) Appl. No.: 14/460,353

(22) Filed: Aug. 14, 2014

(65) Prior Publication Data

US 2015/0023975 A1    Jan. 22, 2015

Related U.S. Application Data

(63) Continuation of application No. 13/263,715, filed as application No. PCT/US2010/030783 on Apr. 12, 2010, now abandoned.

(60) Provisional application No. 61/168,360, filed on Apr. 10, 2009, provisional application No. 61/168,353, filed on Apr. 10, 2009.

(51) Int. Cl.
| | |
|---|---|
| *C07K 16/40* | (2006.01) |
| *A61K 31/00* | (2006.01) |
| *A61K 45/06* | (2006.01) |
| *A61L 17/00* | (2006.01) |
| *A61L 27/54* | (2006.01) |
| *A61L 29/16* | (2006.01) |
| *A61L 31/16* | (2006.01) |
| *A61K 31/65* | (2006.01) |
| *A61K 38/08* | (2006.01) |
| *A61K 38/10* | (2006.01) |
| *A61K 39/395* | (2006.01) |
| *A61K 39/00* | (2006.01) |

(52) U.S. Cl.
CPC ............... *C07K 16/40* (2013.01); *A61K 31/00* (2013.01); *A61K 31/65* (2013.01); *A61K 38/08* (2013.01); *A61K 38/10* (2013.01); *A61K 39/3955* (2013.01); *A61K 45/06* (2013.01); *A61L 17/005* (2013.01); *A61L 27/54* (2013.01); *A61L 29/16* (2013.01); *A61L 31/16* (2013.01); *A61K 2039/505* (2013.01); *A61L 2300/42* (2013.01); *A61L 2300/434* (2013.01); *A61L 2300/436* (2013.01); *C07K 2317/76* (2013.01)

(58) Field of Classification Search
CPC ........................................................ C07K 16/40
See application file for complete search history.

(56) References Cited

PUBLICATIONS

Tressel et al., 2011, A matrix metalloprotease-PAR1 system regulates vascular integrity, systemic inflammation, and death in sepsis, EMBO Molecular medicine, 3: 370-384.*

* cited by examiner

*Primary Examiner* — Amber D Steele
(74) *Attorney, Agent, or Firm* — Duan Wu

(57) ABSTRACT

Matrix metalloproteases (MMPs) play many important roles in normal and pathological remodeling processes including atherothrombotic disease, inflammation, angiogenesis and cancer. This invention relates to the activation of protease-activated receptor-1 (PAR-1) by endogenous platelet MMP-1 collagenase on the surface of platelets. Exposure of platelets to fibrillar collagen converts the surface-bound pro-MMP-1 zymogen to active MMP-1, which promotes aggregation through PAR-1. MMP-1 is shown to cleave the PAR-1 extracellular domain at a novel site, which then strongly activates Rho-GTP signaling pathways, cell shape change and motility, and MAPK signaling. Blockade of MMP-PAR1 suppresses thrombogenesis under arterial flow conditions and inhibited thrombosis in animals. These studies provide a link between matrix-dependent activation of metalloproteases and platelet-G protein signaling and identify MMP-1/PAR-1 as a new target for the treatment and prevention of arterial thrombosis and other thrombotic diseases.

22 Claims, 18 Drawing Sheets

G

H

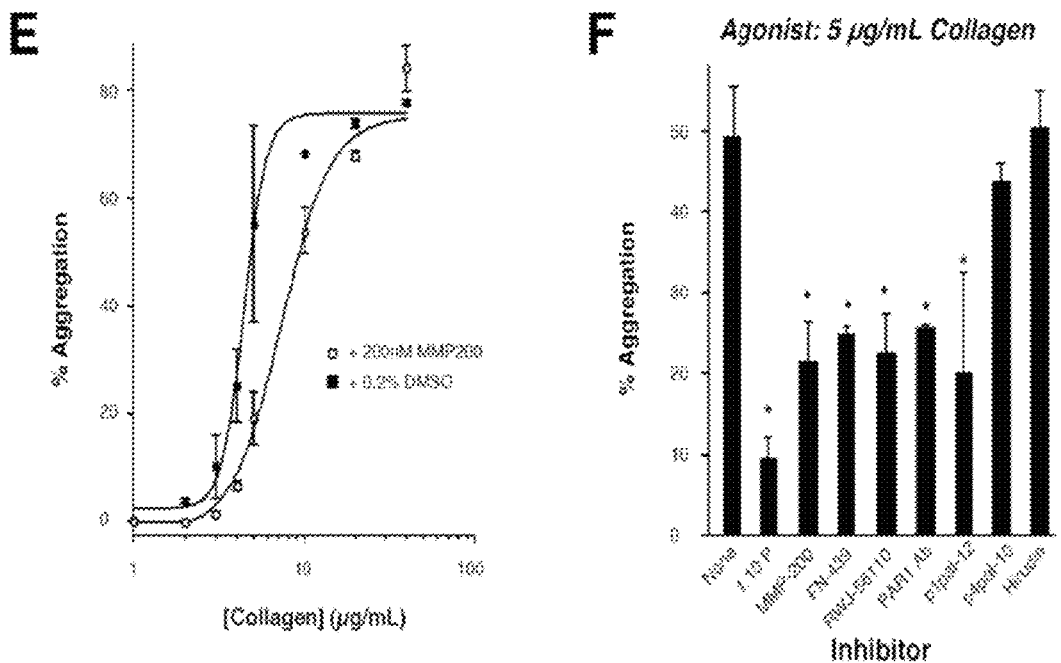

FIGs. 8E-8F

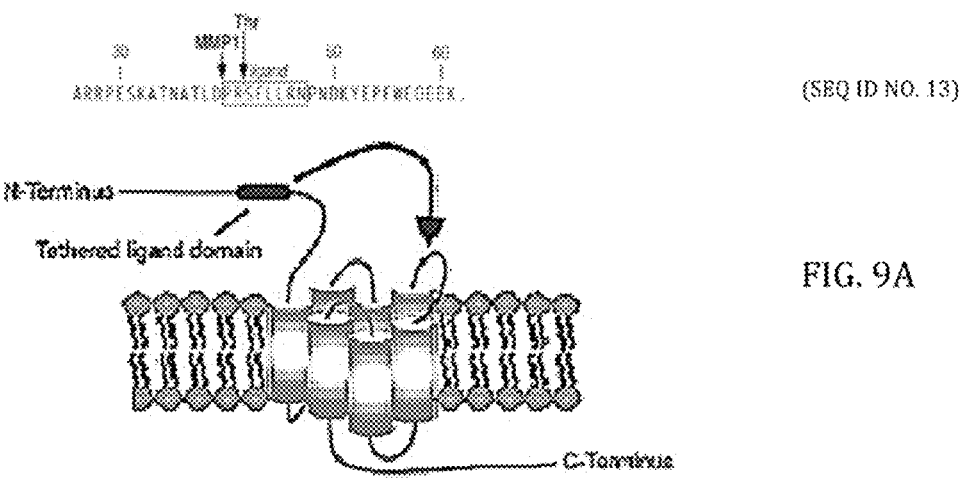

(SEQ ID NO. 13)

FIG. 9A

```
  1 mgprrlllva acfslcqpll sartrarrpe skatnatldp rsfllrnpnd kyepfwedee
 61 knesglteyr lvsinkasspl qkqlpafise dasgyltssw ltlfvpsvyt gvfvvslpln
121 imaivvfilk mkvkkpavvy mlhlatadvl fvsvlpfkis yyfsgsdwqf gselcrfvta
181 afycnmyasi llmtvisidr flavvypmqs lswrtlgras ftclaiwala iagvvplllk
241 eqtiqvpgln ittchdvlne tllegyyayy fsafsavfff vpliistvcy vsiirclass
301 avanrakksr alflsaavfc ifiicfgptn vlliahysfl shtstteaay fayllcvcvs
361 sisccidpli yyyassecqr yvysilccke ssdpssynss gqlmaskmdt cssnlnnsiy
421 kkllt                        (SEQ ID NO. 25)
```

FIG. 9B

SEQUENCE LISTING

```
<160> NUMBER OF SEQ ID NOS: 31

<210> SEQ ID NO 1
<211> LENGTH: 8
<212> TYPE: PRT
<213> ORGANISM: Homo sapiens

<400> SEQUENCE: 1

Pro Arg Ser Phe Leu Leu Arg Asn
1               5

<210> SEQ ID NO 2
<211> LENGTH: 7
<212> TYPE: PRT
<213> ORGANISM: Artificial Sequence
<220> FEATURE:
```

```
<223> OTHER INFORMATION: PAR1 pepducin lipopeptide

<400> SEQUENCE: 2

Lys Lys Ser Arg Ala Leu Phe
1               5

<210> SEQ ID NO 3
<211> LENGTH: 12
<212> TYPE: PRT
<213> ORGANISM: Artificial Sequence
<220> FEATURE:
<223> OTHER INFORMATION: PAR1 pepducin lipopeptide

<400> SEQUENCE: 3

Arg Cys Leu Ser Ser Ser Ala Val Ala Asn Arg Ser
1               5                   10

<210> SEQ ID NO 4
<211> LENGTH: 12
<212> TYPE: PRT
<213> ORGANISM: Artificial Sequence
<220> FEATURE:
<223> OTHER INFORMATION: PAR1 pepducin lipopeptide

<400> SEQUENCE: 4

Arg Ser Leu Ser Ser Ser Ala Val Ala Asn Arg Ser
1               5                   10

<210> SEQ ID NO 5
<211> LENGTH: 10
<212> TYPE: PRT
<213> ORGANISM: Artificial Sequence
<220> FEATURE:
<223> OTHER INFORMATION: PAR1 pepducin lipopeptide

<400> SEQUENCE: 5

Asn Arg Ser Lys Lys Ser Ser Ala Leu Phe
1               5                   10

<210> SEQ ID NO 6
<211> LENGTH: 11
<212> TYPE: PRT
<213> ORGANISM: Artificial Sequence
<220> FEATURE:
<223> OTHER INFORMATION: PAR1 pepducin lipopeptide

<400> SEQUENCE: 6

Ile Leu Lys Met Lys Val Lys Lys Pro Ala Val
1               5                   10

<210> SEQ ID NO 7
<211> LENGTH: 7
<212> TYPE: PRT
<213> ORGANISM: Artificial Sequence
<220> FEATURE:
<223> OTHER INFORMATION: PAR1 pepducin lipopeptide

<400> SEQUENCE: 7

Thr Leu Gly Arg Ala Ser Phe
1               5

<210> SEQ ID NO 8
<211> LENGTH: 11
<212> TYPE: PRT
<213> ORGANISM: Artificial Sequence
<220> FEATURE:
<223> OTHER INFORMATION: PAR1 pepducin lipopeptide
```

```
<400> SEQUENCE: 8

Leu Ser Trp Arg Thr Leu Gly Arg Ala Ser Phe
1               5                   10

<210> SEQ ID NO 9
<211> LENGTH: 16
<212> TYPE: PRT
<213> ORGANISM: Artificial Sequence
<220> FEATURE:
<223> OTHER INFORMATION: PAR1 pepducin lipopeptide

<400> SEQUENCE: 9

Tyr Pro Met Gln Ser Leu Ser Trp Arg Thr Leu Gly Arg Ala Ser Phe
1               5                   10                  15

<210> SEQ ID NO 10
<211> LENGTH: 21
<212> TYPE: PRT
<213> ORGANISM: Artificial Sequence
<220> FEATURE:
<223> OTHER INFORMATION: PAR1 pepducin lipopeptide

<400> SEQUENCE: 10

Phe Leu Ala Val Val Tyr Pro Met Gln Ser Leu Ser Trp Arg Thr Leu
1               5                   10                  15

Gly Arg Ala Ser Phe
            20

<210> SEQ ID NO 11
<211> LENGTH: 13
<212> TYPE: PRT
<213> ORGANISM: Artificial Sequence
<220> FEATURE:
<223> OTHER INFORMATION: PAR1 pepducin lipopeptide

<400> SEQUENCE: 11

Ala Ser Ser Glu Ser Gln Arg Tyr Val Tyr Ser Ile Leu
1               5                   10

<210> SEQ ID NO 12
<211> LENGTH: 13
<212> TYPE: PRT
<213> ORGANISM: Artificial Sequence
<220> FEATURE:
<223> OTHER INFORMATION: PAR1 pepducin lipopeptide

<400> SEQUENCE: 12

Leu Ile Ser Tyr Val Tyr Arg Gln Ser Glu Ser Ser Ala
1               5                   10

<210> SEQ ID NO 13
<211> LENGTH: 36
<212> TYPE: PRT
<213> ORGANISM: Homo sapiens

<400> SEQUENCE: 13

Ala Arg Arg Pro Glu Ser Lys Ala Thr Asn Ala Thr Leu Asp Pro Arg
1               5                   10                  15

Ser Phe Leu Leu Arg Asn Pro Asn Asp Lys Tyr Glu Pro Phe Trp Glu
                20                  25                  30

Asp Glu Glu Lys
            35
```

```
<210> SEQ ID NO 14
<211> LENGTH: 36
<212> TYPE: PRT
<213> ORGANISM: Artificial Sequence
<220> FEATURE:
<223> OTHER INFORMATION: PAR1 N-terminal extracellular mutant

<400> SEQUENCE: 14

Met Ala Ser Met Thr Gly Gly Gln Gln Met Gly Thr Leu Asp Pro Arg
1               5                   10                  15

Ser Phe Leu Leu Arg Asn Pro Asn Asp Lys Tyr Glu Pro Phe Trp Glu
                20                  25                  30

Asp Glu Glu Lys
            35

<210> SEQ ID NO 15
<211> LENGTH: 26
<212> TYPE: PRT
<213> ORGANISM: Artificial Sequence
<220> FEATURE:
<223> OTHER INFORMATION: PAR1 N-terminal extracellular mutant

<400> SEQUENCE: 15

Ala Thr Leu Asp Pro Arg Ser Phe Leu Leu Arg Asn Pro Asn Asp Lys
1               5                   10                  15

Tyr Glu Pro Phe Trp Glu Asp Glu Glu Ser
                20                  25

<210> SEQ ID NO 16
<211> LENGTH: 20
<212> TYPE: PRT
<213> ORGANISM: Artificial Sequence
<220> FEATURE:
<223> OTHER INFORMATION: PAR1 N-terminal extracellular mutant

<400> SEQUENCE: 16

Ser Phe Leu Leu Arg Asn Pro Asn Asp Lys Tyr Glu Pro Phe Trp Glu
1               5                   10                  15

Asp Glu Glu Ser
            20

<210> SEQ ID NO 17
<211> LENGTH: 22
<212> TYPE: PRT
<213> ORGANISM: Artificial Sequence
<220> FEATURE:
<223> OTHER INFORMATION: PAR1 N-terminal extracellular mutant

<400> SEQUENCE: 17

Pro Arg Ser Phe Leu Leu Arg Asn Pro Asn Asp Lys Tyr Glu Pro Phe
1               5                   10                  15

Trp Glu Asp Glu Glu Ser
                20

<210> SEQ ID NO 18
<211> LENGTH: 26
<212> TYPE: PRT
<213> ORGANISM: Artificial Sequence
<220> FEATURE:
<223> OTHER INFORMATION: PAR1 N-terminal extracellular mutant

<400> SEQUENCE: 18

Ala Thr Leu Asp Asn Arg Ser Phe Leu Leu Arg Asn Pro Asn Asp Lys
1               5                   10                  15
```

```
Tyr Glu Pro Phe Trp Glu Asp Glu Glu Lys
            20                  25

<210> SEQ ID NO 19
<211> LENGTH: 36
<212> TYPE: PRT
<213> ORGANISM: Artificial Sequence
<220> FEATURE:
<223> OTHER INFORMATION: PAR1 N-terminal extracellular mutant

<400> SEQUENCE: 19

Met Ala Ser Met Thr Gly Gly Gln Gln Met Gly Thr Leu Asp Asn Arg
1               5                   10                  15

Ser Phe Leu Leu Arg Asn Pro Asn Asp Lys Tyr Glu Pro Phe Trp Glu
                20                  25                  30

Asp Glu Glu Lys
            35

<210> SEQ ID NO 20
<211> LENGTH: 36
<212> TYPE: PRT
<213> ORGANISM: Artificial Sequence
<220> FEATURE:
<223> OTHER INFORMATION: PAR1 N-terminal extracellular mutant

<400> SEQUENCE: 20

Met Ala Ser Met Thr Gly Gly Gln Gln Met Gly Thr Leu Asp Pro Arg
1               5                   10                  15

Asp Phe Leu Leu Arg Asn Pro Asn Asp Lys Tyr Glu Pro Phe Trp Glu
                20                  25                  30

Asp Glu Glu Lys
            35

<210> SEQ ID NO 21
<211> LENGTH: 8
<212> TYPE: PRT
<213> ORGANISM: Artificial Sequence
<220> FEATURE:
<223> OTHER INFORMATION: PAR1 N-terminal extracellular mutant

<400> SEQUENCE: 21

Arg Pro Ser Phe Leu Leu Arg Asn
1               5

<210> SEQ ID NO 22
<211> LENGTH: 7
<212> TYPE: PRT
<213> ORGANISM: Artificial Sequence
<220> FEATURE:
<223> OTHER INFORMATION: PAR1 N-terminal extracellular mutant

<400> SEQUENCE: 22

Arg Ser Phe Leu Leu Arg Asn
1               5

<210> SEQ ID NO 23
<211> LENGTH: 6
<212> TYPE: PRT
<213> ORGANISM: Artificial Sequence
<220> FEATURE:
<223> OTHER INFORMATION: PAR1 N-terminal extracellular mutant

<400> SEQUENCE: 23

Ser Phe Leu Leu Arg Asn
1               5
```

<210> SEQ ID NO 24
<211> LENGTH: 9
<212> TYPE: PRT
<213> ORGANISM: Artificial Sequence
<220> FEATURE:
<223> OTHER INFORMATION: PAR1 N-terminal extracellular mutant

<400> SEQUENCE: 24

Asp Pro Arg Ser Phe Leu Leu Arg Asn
1               5

<210> SEQ ID NO 25
<211> LENGTH: 425
<212> TYPE: PRT
<213> ORGANISM: Homo sapiens

<400> SEQUENCE: 25

Met Gly Pro Arg Arg Leu Leu Leu Val Ala Ala Cys Phe Ser Leu Cys
1               5                   10                  15

Gly Pro Leu Leu Ser Ala Arg Thr Arg Ala Arg Arg Pro Glu Ser Lys
            20                  25                  30

Ala Thr Asn Ala Thr Leu Asp Pro Arg Ser Phe Leu Leu Arg Asn Pro
        35                  40                  45

Asn Asp Lys Tyr Glu Pro Phe Trp Glu Asp Glu Glu Lys Asn Glu Ser
50                  55                  60

Gly Leu Thr Glu Tyr Arg Leu Val Ser Ile Asn Lys Ser Ser Pro Leu
65                  70                  75                  80

Gln Lys Gln Leu Pro Ala Phe Ile Ser Glu Asp Ala Ser Gly Tyr Leu
                85                  90                  95

Thr Ser Ser Trp Leu Thr Leu Phe Val Pro Ser Val Tyr Thr Gly Val
            100                 105                 110

Phe Val Val Ser Leu Pro Leu Asn Ile Met Ala Ile Val Val Phe Ile
        115                 120                 125

Leu Lys Met Lys Val Lys Lys Pro Ala Val Val Tyr Met Leu His Leu
130                 135                 140

Ala Thr Ala Asp Val Leu Phe Val Ser Val Leu Pro Phe Lys Ile Ser
145                 150                 155                 160

Tyr Tyr Phe Ser Gly Ser Asp Trp Gln Phe Gly Ser Glu Leu Cys Arg
                165                 170                 175

Phe Val Thr Ala Ala Phe Tyr Cys Asn Met Tyr Ala Ser Ile Leu Leu
            180                 185                 190

Met Thr Val Ile Ser Ile Asp Arg Phe Leu Ala Val Val Tyr Pro Met
        195                 200                 205

Gln Ser Leu Ser Trp Arg Thr Leu Gly Arg Ala Ser Phe Thr Cys Leu
210                 215                 220

Ala Ile Trp Ala Leu Ala Ile Ala Gly Val Val Pro Leu Leu Leu Lys
225                 230                 235                 240

Glu Gln Thr Ile Gln Val Pro Gly Leu Asn Ile Thr Thr Cys His Asp
                245                 250                 255

Val Leu Asn Glu Thr Leu Leu Glu Gly Tyr Tyr Ala Tyr Tyr Phe Ser
            260                 265                 270

Ala Phe Ser Ala Val Phe Phe Val Pro Leu Ile Ile Ser Thr Val
        275                 280                 285

Cys Tyr Val Ser Ile Ile Arg Cys Leu Ser Ser Ser Ala Val Ala Asn
        290                 295                 300

```
Arg Ser Lys Lys Ser Arg Ala Leu Phe Leu Ser Ala Ala Val Phe Cys
305                 310                 315                 320

Ile Phe Ile Ile Cys Phe Gly Pro Thr Asn Val Leu Leu Ile Ala His
            325                 330                 335

Tyr Ser Phe Leu Ser His Thr Ser Thr Thr Glu Ala Ala Tyr Phe Ala
        340                 345                 350

Tyr Leu Leu Cys Val Cys Val Ser Ile Ser Cys Cys Ile Asp Pro
    355                 360                 365

Leu Ile Tyr Tyr Tyr Ala Ser Ser Glu Cys Gln Arg Tyr Val Tyr Ser
370                 375                 380

Ile Leu Cys Cys Lys Glu Ser Ser Asp Pro Ser Ser Tyr Asn Ser Ser
385                 390                 395                 400

Gly Gln Leu Met Ala Ser Lys Met Asp Thr Cys Ser Ser Asn Leu Asn
            405                 410                 415

Asn Ser Ile Tyr Lys Lys Leu Leu Thr
            420                 425

<210> SEQ ID NO 26
<211> LENGTH: 6
<212> TYPE: PRT
<213> ORGANISM: artificial sequence
<220> FEATURE:
<223> OTHER INFORMATION: PAR1 fragment mutant

<400> SEQUENCE: 26

Thr Phe Leu Leu Arg Asn
1               5

<210> SEQ ID NO 27
<211> LENGTH: 7
<212> TYPE: PRT
<213> ORGANISM: artificial sequence
<220> FEATURE:
<223> OTHER INFORMATION: PAR1 fragment mutant

<400> SEQUENCE: 27

Pro Ser Phe Leu Leu Arg Asn
1               5

<210> SEQ ID NO 28
<211> LENGTH: 16
<212> TYPE: PRT
<213> ORGANISM: homo sapiens

<400> SEQUENCE: 28

Ala Arg Arg Pro Glu Ser Lys Ala Thr Asn Ala Thr Leu Asp Pro Arg
1               5                   10                  15

<210> SEQ ID NO 29
<211> LENGTH: 19
<212> TYPE: PRT
<213> ORGANISM: Homo sapiens

<400> SEQUENCE: 29

Thr Glu Tyr Arg Leu Val Ser Ile Asn Lys Ser Ser Pro Leu Gln Lys
1               5                   10                  15

Gln Leu Cys

<210> SEQ ID NO 30
<211> LENGTH: 15
<212> TYPE: PRT
<213> ORGANISM: Artificial
```

-continued

```
<220> FEATURE:
<223> OTHER INFORMATION: derived from part of a human gene

<400> SEQUENCE: 30

Ser Phe Leu Leu Arg Asn Pro Asn Asp Lys Tyr Glu Pro Phe Cys
1               5                   10                  15

<210> SEQ ID NO 31
<211> LENGTH: 7
<212> TYPE: PRT
<213> ORGANISM: homo sapiens

<400> SEQUENCE: 31

Leu Asp Pro Arg Ser Phe Leu
1               5
```

PAR-1 ACTIVATION BY METALLOPROTEINASE-1 (MMP-1)

CROSS-REFERENCE TO RELATED APPLICATIONS

This application is a continuation application of, and claims priority to and benefit of, co-pending U.S. application Ser. No. 13/263,715, filed on Oct. 7, 2011 as a national phase application under 35 U.S.C. 371 of international application PCT/US2010/030783, filed Apr. 12, 2010 which, in turn, claims priority to and the benefit of co-pending U.S. provisional patent applications Ser. Nos. 61/168,353 and 61/168,360, both of the above title and both filed on Apr. 10 2009, which applications are incorporated herein by reference in entirety to the extent allowed by applicable laws.

STATEMENT REGARDING FEDERALLY FUNDED RESEARCH AND DEVELOPMENT

This invention was made with Government support under Grant Nos. R01 HL-57905, R01 HL-64701, and R01 CA-122992, awarded by the National Institutes of Health. The government has certain rights in this invention.

FIELD OF INVENTION

The present invention relates to the diagnosis and treatment of thrombotic conditions including those related to acute coronary syndrome and atherosclerosis. The invention also relates to means of preserving platelets for research or clinical uses.

BACKGROUND

Platelet activation and aggregation, while needed for normal physiological functions such as hemostasis, can lead to a myriad of oft-lethal and highly debilitating conditions and pathologies when their regulatory mechanisms malfunction. These pathological conditions can be acute or chronic, and include acute coronary syndrome, myocardial infarction, unstable angina, stroke, coronary thrombosis, venous thrombosis, atherothrombosis, restenosis and so on. In the United States, Europe, and other industrialized nations, myocardial infarction due to rupture of atherosclerotic plaques is a leading contributor to morbidity and mortality. Acute plaque rupture exposes subendothelial collagen which promotes platelet activation and formation of a potentially occlusive thrombus at the site of vascular damage (Glass and Witztum, 2001; Rugged, 2002). Following their initial tethering to subendothelial collagen and matrix proteins, activation of transiently adhered platelets by autocrine mediators is critical for the propagation of the formative platelet thrombus. Reinforcement of the transient adhesive contacts by activating G protein-dependent shape change, granule release, and integrins permits growth of a stable thrombus that is resistant to the high shear stress of arterial blood flow (Jackson et al., 2003; Moers et al., 2003). Drugs that target the secondary autocrine mediators of platelet thrombus formation such as aspirin and thienopyridines have proven to be beneficial, however, many patients taking these drugs still sustain thrombotic events, and, therefore, might benefit from new therapeutics that interfere with matrix-dependent platelet activation (Bhatt and Topol, 2003).

Two distinct pathways act in parallel to activate platelets during hemostasis (Furie and Furie, 2008). As the blood vessel wall gets breached, platelets circulating in blood first encounter collagen embedded in the subendothelial matrix. As a first line of defense, exposed collagen initiates the accumulation and activation of platelets and starts the formation of a thrombus. As blood flows out further, it encounters a second line of defense, the tissue factor located in the medial and adventitial layers of the vessel wall, and a second independent pathway is triggered that also activates platelets to adhere to each other and form part of the developing thrombus. The tissue factor-initiated pathway generates thrombin which in turn cleaves protease-activated receptor 1(PAR1) on the human platelet surface, causing them to release adenosine diphosphate (ADP), serotonin, and thromboxane $A_2$. In turn, these agonists recruit and activate other platelets, amplifying the signal in order to block off the breach in the vessel wall. The present invention, however, is based on discoveries that center around the other, collagen-initiated platelet activation pathway, i.e., the first line of defense in a thrombotic event.

Matrix metalloproteases (MMPs) have recently emerged as important mediators of platelet function and vascular biology. Initially described as extracellular matrix remodeling enzymes involved in tissue repair and cancer invasion (Egeblad and Werb, 2002), a renewed focus has centered on MMPs and the related metalloprotease disintegrins because of their prominence in vascular wall inflammation (Dollery and Libby. 2006) and thrombotic thrombocytopenic purpura (Levy et al., 2001). Endogenous platelet metalloproteases have been shown to damage platelet function by cleaving cell surface receptors and broad-spectrum metalloprotease inhibitors improve post-transfusion recovery of platelet concentrates (Bergmeier et al., 2003; Bergmeier et al., 2004; Stephens et al., 2004). Platelets express several metalloproteases including MMP-1, MMP-2, MMP-3, and MMP-14 on their surface (Chesney et al., 1974; Gait et al., 2002; Kazes at al., 2000; Sawicki et al., 1997). Notably, endogenous MMP-1 and MMP-2 can actually promote platelet aggregation but the cell surface target(s) and mechanism of activation have not been elucidated (Gait et al., 2002; Sawicki et al., 1997). A recent study that examined the effects of MMP-1 promoter polymorphisms in 2000 patients, found a significantly increased risk of myocardial infarction in patients with high promoter activity haplotypes and a significantly decreased risk in patients with low promoter activity haplotypes (Pearce et al., 2005).

It was recently shown that the G protein-coupled receptor, PAR1, is directly cleaved and activated on the surface of cancer cells by fibroblast-derived MMP-1 (Boire et al., 2005). PAR1 is the major thrombin receptor of human platelets (Coughlin, 2000; Leger et al., 2006b) and is an important mediator of platelet aggregation following tissue factor (TF)-dependent generation of thrombin (Mackman, 2004; Schwertz et al., 2006). However, under pathophysiologic conditions of acute plaque rupture, exposed collagen is the most efficient stimulus of the critical early events of platelet recruitment and propagation under arterial flow which could trigger metalloprotease activation on the platelet surface.

SUMMARY OF INVENTION

The present invention is based on a novel metalloprotease-dependent pathway of platelet thrombogenesis through PAR1. Exposure of platelets to collagen caused activation of MMP-1 which in turn directly cleaved PAR1 on the surface of platelets. Unexpectedly, MMP-1 cleaved the N-terminal extracellular domain of PAR1 at a distinct site from the thrombin cleavage site. This cleavage event generated a longer tethered peptide ligand which was an agonist of platelet activation and PAR1 signaling. Blocking the MMP1-

PAR1 pathway inhibited physiological events such as collagen-dependent thrombogenesis, arterial thrombosis and clot retraction. Accordingly, the present invention provides methods and therapeutics that target this metalloprotease-receptor system in treatment of patients diagnosed with or at risk of developing a thrombotic disease state such as acute coronary syndromes.

In one aspect, the invention provides for a method of treating a patient diagnosed with or at substantial risk of developing a thrombotic disease state by administering a therapeutically effective amount of an agent that substantially inhibits proteolytic cleavage between aspartic acid at position 39 (D39) and proline at position 40 (P40) of said patient's protease-activated receptor-1 (PAR-1). The proteolytic cleavage may require an enzymatic activity by matrix metalloprotease-1 (MMP-1).

The patient may be exhibiting or has exhibited one or more symptoms such as chest pain, shortness of breath, tightness around chest, tightness in left arm, tightness in left angle of jaw, excessive sweating, nausea, vomiting, palpitation, anxiety, or atypical sensation. The patient may have one or more ascertainable or diagnosable risk factors associated with a thrombotic disease state.

A thrombotic disease state may be any pathology that results from platelet aggregation, including but not limited to acute coronary syndrome, arterial thrombosis, venous thrombosis, peripheral arterial disease, unstable angina, atrial fibrillation, first myocardial infarction, recurrent myocardial infarction, ischemic sudden death, transient ischemic attack, stroke, atherosclerosis, deep vein thrombosis, thrombophlebitis, arterial embolism, coronary arterial thrombosis, cerebral arterial thrombosis, cerebral embolism, kidney embolism or pulmonary embolism.

In one embodiment, the method of the invention is used to treat a patient diagnosed with cancer.

In one feature, the administration of the agent substantially inhibits platelet activation in a patient. The agent may be a ligand-binding molecule that binds to PAR-1, substantially inhibits the cleavage of PAR-1 by binding over the cleavage site or substantially inhibits the cleavage of PAR-1 by inducing a conformational change in PAR-1. The agent may include a ligand-binding molecule that binds to MMP-1 or an antibody that is specific for MMP-1 or PAR-1. The agent may also include a small molecule that binds to MMP-1 or PAR-1.

In some embodiments, the agent substantially inhibits activation of matrix metalloprotease-1 (MMP-1) or MMP-1 enzymatic activity, cleavage of proMMP-1 by a protease, cleavage of proMMP-1 by matrix metalloprotease-2 (MMP-2) or collagen-initiated MMP-1 activation. The agent may be FN-439, tissue inhibitors of metalloprotease (TIMPs). MMP-200. Cipemastat (Trocade), Prinomastat, BAY 12-9566, Batimistat, BMS-275291. Marimastat. MMI270(B). Metastat, Ro 32-3555, RS-130,830, PD 166793, Ancorinosides B-D, a tetracycline compound or doxycycline.

The method of the present invention further provides for administering to the patient a second agent that substantially inhibits at least one of thromboxane- and ADP-signaling pathways in patient's platelets, at least some of PAR-1's enzymatic activity or thrombin-dependent activation of PAR1. The second agent complements the first agent, e.g., by inhibiting the tissue-factor-initiated hemostatic pathway.

The method further provides for the administration of a second anti-thrombotic agent including anti-platelet drugs, anti-coagulant drugs, or thrombolytic drugs. The second anti-thrombotic agent may be thienopyridines, prostaglandin analogs, COX inhibitors, vitamin K antagonists, glycoprotein IIB/IIIA inhibitors or thrombin inhibitors.

In another embodiment, the second agent may be aspirin, clopidogrel, ticlopidine, prasugrel, heparin, abciximab, eptifibatid, tirofiban and bivalirudin.

In another embodiment, the second agent may be a pepducin lipopeptide of a PAR family member or a PAR-1 pepducin lipopeptide such as P1i3pal-7, P1i3pal-12, P1i3pal-12S, P1i3pal-10S, P1i1pal-11, P1i2pal-7, P1i2pal-11, P1i2pal-16, P1i2pal-21, P1i4pal13 or P1i4pal13R.

The method further provides for administration of the agent by intravenous (I.V.) injection, subcutaneous injection, intramuscular injection, oral ingestion, nasal, topical, rectal, vaginal or parenteral intake. The agent may be formulated with a pharmaceutically acceptable excipient, carrier or diluent.

In a second aspect, the invention provides for a method of treating a thrombotic disease state in a patient by administering to a patient diagnosed with or at substantial risk of developing a thrombotic disease state a therapeutically effective amount of an agent that substantially inhibits the patient's protease-activated receptor-1 (PAR-1) signaling activity that results from proteolytic cleavage of PAR-1 between aspartic acid at position 39 (D39) and proline at position 40 (P40). In one embodiment, the agent comprises SCH 530348.

In another embodiment, the agent comprises a pepducin lipopeptide of a PAR family member or a PAR-1 pepducin lipopeptide such as P1i3pal-7, P1i3pal-12, P1i3pal-12S, P1i3pal-10S, P1i1pal-11, P1i2pal-7, P1i2pal-11, P1i2pal-16, P1i2pal-21, P1i4pal13 or P1i4pal13R.

In a third aspect, the invention provides for a method of treating a patient diagnosed with or at substantial risk of developing a thrombotic disease state by administering a therapeutically effective amount of an agent that substantially inhibits activation of matrix metalloprotease-1 (MMP-1) or MMP-1 enzymatic activity.

The agent substantially inhibits cleavage of proMMP-1 by a proteinase, cleavage of proMMP-1 by matrix metalloprotease-2 (MMP-2) or collagen-initiated MMP-1 activation. The agent may be FN-439, tissue inhibitors of metalloprotease (TIMPs). MMP-200, Cipemastat (Trocade), Prinomastat, BAY 12-9566, Batimistat, BMS-275291, Marimastat, MMI270(B), Metastat, Ro 32-3555, RS-130,830, PD 166793, Ancorinosides B-D, a tetracycline compound or doxycycline.

In a fourth aspect, the invention provides for a method of treating a patient diagnosed with or at substantial risk of developing atherosclerosis by administering a therapeutically effective amount of an agent that substantially inhibits proteolytic cleavage between aspartic acid at position 39 (039) and proline at position 40 (P40) of said patient's protease-activated receptor-1 (PAR-1).

The agent may be administered after an angioplasty procedure, a coronary bypass procedure, or an open-heart surgery has been performed on the patient but preferably for no more than two weeks.

In a fifth aspect, the invention provides a method of treating atherosclerosis by administering to a patient diagnosed with or at substantial risk of developing atherosclerosis a therapeutically effective amount of an agent that substantially inhibits the patient's protease-activated receptor-1 (PAR-1) signaling activity that results from proteolytic cleavage of PAR-1 between aspartic acid at position 39 (039) and proline at position 40 (P40).

In one aspect, the agent reduces the size of atherosclerotic plaque within the aorta of the patient.

In one embodiment, the agent comprises SCH 530348.

In another embodiment, the agent comprises a pepducin lipopeptide of a PAR family member or a PAR-1 pepducin lipopeptide such as P1i3pal-7, P1i3pal-12, P1i3pal-12S, P1i3pal-10S, P1i1pal-11, P1i2pal-7, P1i2pal-11, P1i2pal-16, P1i2pal-21, P1i4pal13 or P1i4pal13R.

In a sixth aspect, the invention provides for a method of treating a patient diagnosed with or at substantial risk of developing atherosclerosis by administering a therapeutically effective amount of an agent that substantially inhibits activation of matrix metalloprotease-1 (MMP-1) or MMP-1 enzymatic activity.

In another aspect, the invention also provides for a medium for platelet storage or transportation having an effective concentration of an agent that substantially inhibits proteolytic cleavage between aspartic acid at position 39 (D39) and proline at position 40 (P40) of protease-activated receptor-1 (PAR-1) on platelets contained therein. The medium may be an aqueous solution further containing glucose and the average half-life of a normal platelet contained therein is no less than about 5 days or 1 month or 6 months. The medium may have an effective concentration of an agent that inhibits activation of matrix metalloprotease-1 (MMP-1) or MMP-1 enzymatic activity. The medium may have include a pepducin lipopeptide of a PAR family member or a PAR-1 pepducin lipopeptide such as P1i3pal-7, P1i3pal-12, P1i3pal-12S, P1i3pal-10S, P1i1pal-11, P1i2pal-7, P1i2pal-11, P1i2pal-16, P1i2pal-21, P1i4pal13 or P1i4pal13R.

In another aspect, the invention provides for a medium for platelet storage or transportation, said medium having an effective concentration of an agent that substantially inhibits protease-activated receptor-1 (PAR-1) signaling activity that results from proteolytic cleavage of PAR-1 between aspartic acid at position 39 (D39) and proline at position 40 (P40).

In one embodiment, the agent comprises SCH 530348.

In yet another aspect, the invention provides a method of diagnosing a risk for suffering a hemorrhagic event in a patient by determining whether the patient has a genetic defect that substantially inhibits activation of matrix metalloprotease-1 (MMP-1) or MMP-1 activity inside the patient.

In a further aspect, the invention provides a method of diagnosing a hemophilic or coagulopathic condition or a risk thereof in a patient by determining whether the patient has a genetic defect that over-stimulates activation of matrix metalloprotease-1 (MMP-1) or MMP-1 enzymatic activity inside the patient.

The invention further provides an isolated polypeptide having a sequence comprising no less than 5 contiguous amino acid residues of one of the two fragments that result from a proteolytic deavage between aspartic add at position 39 (D39) and proline at position 40 (P40) of human protease-activated receptor-1 (PAR-1) polypeptide that terminates at one end with a cleavage site that would have resulted from the proteolytic cleavage. The polypeptide of the invention can have a proline at its N terminus and, e.g., have the polypeptide sequence of PRSFLLRN (SEQ ID NO. 1). Alternately, the polypeptide of the invention can have an aspartic acid at its C terminus and have at least another four amino acid residues as shown to the left of D39 in FIG. 9B, which provides the full polypeptide sequence of human PAR-1 and in which the D39 and P40 straddling the cleavage site are bolded and underlined.

The invention also provides for a method of diagnosing a thrombotic disease state in a patient by measuring the amount of the polypeptide of the invention in platelets taken from a patient.

In yet another aspect, a method of identifying a PAR-1 antagonist is disclosed having the steps of providing an isolated polypeptide of the invention having a sequence comprising no less than 5 contiguous amino acid residues of one of the two fragments that result from a proteolytic cleavage between aspartic add at position 39 (D39) and proline at position 40 (P40) of human protease-activated receptor-1 (PAR-1) polypeptide that terminates at one end with a cleavage site that would have resulted from the proteolytic cleavage, providing a candidate agent, contacting platelets with the isolated polypeptide in the presence of said candidate agent, measuring PAR-1 signaling activity, and comparing the PAR-1 signaling activity in the presence of the candidate agent to the PAR-1 signaling activity in the absence of the candidate agent, wherein a decrease of at least 10% in PAR-1 signaling activity in the presence of the candidate agent as compared to PAR-1 signaling activity in the absence of the candidate agent identifies the candidate agent as a PAR-1 antagonist.

The PAR-1 signaling activity may include Rho-GTP or MAPK pathway signaling.

In a further aspect, a method of identifying a PAR-1 antagonist is disclosed having the steps of providing activated MMP-1, providing a candidate agent, contacting platelets with the activated MMP-1 in the presence of the candidate agent under conditions where MMP-1 cleaves PAR-1, measuring PAR-1 signaling activity, and comparing the PAR-1 signaling activity in the presence of the candidate agent to the PAR-1 signaling activity in the absence of the candidate agent, wherein a decrease of at least 10% in PAR-1 signaling activity in the presence of the candidate agent as compared to PAR-1 signaling activity in the absence of the candidate agent identifies the candidate agent as a PAR-1 antagonist.

The PAR-1 signaling activity may include Rho-GTP or MAPK pathway signaling.

In one aspect, the invention discloses a medical device coated with a matrix layer comprising an agent that substantially inhibits proteolytic cleavage between aspartic acid at position 39 (D39) and proline at position 40 (P40) of said patient's protease-activated receptor-1 (PAR-1).

In another aspect, the invention discloses a medical device coated with a matrix layer comprising an agent that substantially inhibits protease-activated receptor-1 (PAR-1) signaling activity that results from proteolytic cleavage of PAR-1 between aspartic acid at position 39 (D39) and praline at position 40 (P40). In one embodiment, the agent comprises SCH 530348.

In another embodiment, the agent comprises a pepducin lipopeptide of a PAR family member or a PAR-1 pepducin lipopeptide such as P1i3pal-7, P1i3pal-12, P1i3pal-12S, P1i3pal-10S, P1i1pal-11, P1i2pal-7, P1i2pal-11, P1i2pal-16, P1i2pal-21, P1i4pal13 or P1i4pal13R.

The matrix layer may be a biocompatible peptide matrix. The medical device may be implantable. The matrix may further include a pepducin lipopeptide of a PAR family member or a PAR-1 pepducin lipopeptide, such as P1i3pal-7, P1i3pal-12, P1i3pal-12S, P1i3pal-10S, P1i1pal-11, P1i2pal-7. P1i2pal-11. P1i2pal-16, P1i2pal-21, P1i4pal 13 or P1i4pal13R.

The previously described embodiments have many advantages, including methods for the discovery and administration of agents that inhibit the MMP-1 mediated PAR-1 signaling pathway. The methods, compositions and kits disclosed herein are therefore particularly useful for treatment of patients diagnosed with or at risk of acquiring a thrombotic disease state.

It should be understood that this application is not limited to the embodiments disclosed in this Summary, and it is intended to cover modifications and variations that are within the scope of those of sufficient skill in the field, and as defined by the claims.

BRIEF DESCRIPTION OF THE FIGURES

FIGS. 8A-8F show that pharmacologic inhibition of Matrix Metalloprotease-2 (MMP-2) attenuates collagen-dependent platelet aggregation to a similar extent as blockade of MMP-1.

FIG. 9A depicts a proposed model of MMP-1 mediated PAR-1 activation by PAR-1's tethered ligand.

FIG. 9B shows the human PAR-1 polypeptide sequence (Genbank Accession No. NP_001983).

DETAILED DESCRIPTION

Figures 1A, 1B, 1C:
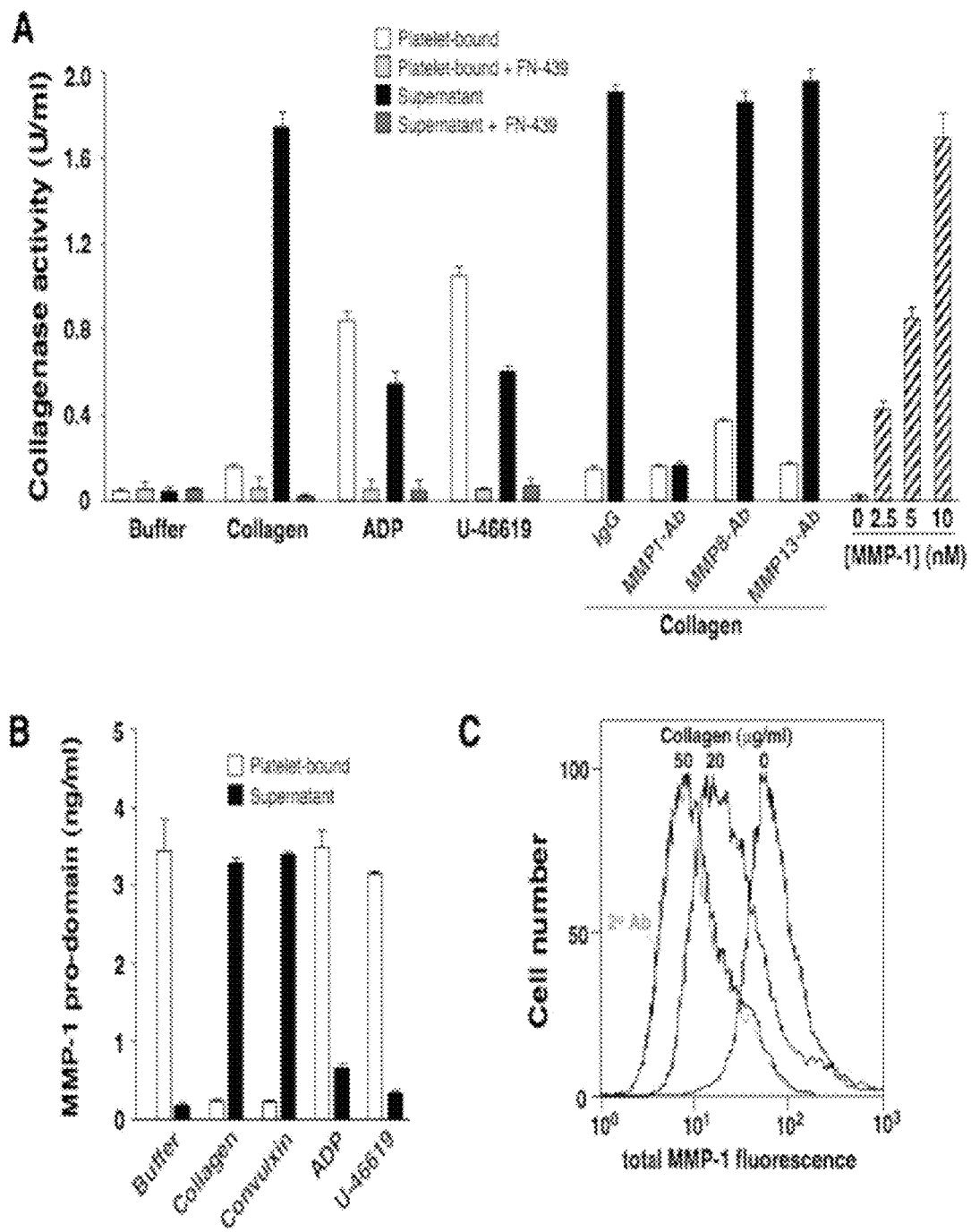
FIG. 1A shows the MMP activity in human platelets after treatment with either ADP, U-46619, or type-I collagen.
FIG. 1B shows ELISA measurements of released and platelet-associated MMP-1 pro-domains in the pellets and supernatants collected from the platelets of FIG. 1.
FIG. 1C shows the expression of MMP-1 on the surface of platelets as determined by flow cytometry.

Unless defined otherwise, all technical and scientific terms used herein have the same meaning as is commonly understood by one of skill in the art. The following definitions are provided to help interpret the disclosure and claims of this application. In the event a definition in this section is not consistent with definitions elsewhere, the definition set forth in this section will control.

As used herein, the term "about" or "approximately" when used in conjunction with a number refers to any number within 5, 10 or 15% of the referenced number.

As used herein the terms "administration," "administering," or the like, when used in the context of providing a pharmaceutical or nutraceutical composition to a subject generally refers to providing to the subject one or more pharmaceutical compositions comprising the agent, e.g., an agonist or antagonist of the MMP-1 mediated PAR-1 signaling pathway, in combination with an appropriate delivery vehicle by any means such that the administered compound achieves one or more of the intended biological effects for which the compound was administered. By way of non-limiting example, a composition may be administered parenteral, subcutaneous, intravenous, intracoronary, rectal, intramuscular, intra-peritoneal, transdermal, or buccal routes of delivery.

In one embodiment, "administration" of the agent, e.g., an agonist or antagonist of the MMP-1 mediated PAR-1 signaling pathway, to the patient may require controlled release, i.e., the release of the active ingredient from the formulation in a sustained and regulated manner over a longer period of time than an immediate release formulation containing the same amount of the active ingredient would release during the same time period. The dosage administered will be dependent upon the age, health, weight, and/or thrombotic disease state of the recipient and/or other associated risk factors, the kind of concurrent treatment, if any, the frequency of treatment, and/or the nature of the effect desired.

As used herein, an "agonist" refers to any natural or synthetic molecule or combination of molecules that increases a biological activity by at least or at least about 2 fold, about 3 fold, about 4 fold, about 5 fold, about 7 fold, about 10 fold, about 20 fold, about 50 fold or about 100 fold or more in a standard bioassay or in vivo or when used in a therapeutically effective dose. In one embodiment, an "agonist" "refers to any natural or synthetic molecule or combination of molecules that activates MMP-1 mediated PAR-1 signaling.

An "antagonist" or "inhibitor" may be used interchangeably herein and refers to any natural or synthetic molecule or combination of molecules that interferes with a biological activity by at least or at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or about 100% in a standard bioassay or in vive or when used in a therapeutically effective dose. In one embodiment, an "antagonist" or "inhibitor" refers to any natural or synthetic molecule or combination of molecules that interferes with MMP-1 mediated PAR-1 activity. In another embodiment, an "antagonist" or "inhibitor" refers to any natural or synthetic molecule or combination of molecules that inhibits MMP-1 mediated PAR-1 activation.

In another embodiment, an "antagonist" or 'inhibitor' refers to a compound that inhibits cleavage between aspartic acid at position 39 (D39) and proline at position 40 (P40) of the protease-activated receptor-1 (PAR-1) by at least or at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or about 100%.

In one embodiment, an "antagonist" of the MMP1-mediated PAR-1 signaling pathway may be identified by its ability to fully or partially inhibit PAR-I mediated signaling activity, as measured, for example, by PAR1-dependent Rho and p38 MAPK signaling. Inhibition occurs when PAR-I intracellular signaling from a PAR-I receptor exposed to an 'agent' of the invention is by at least or at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or about 100% in comparison to intracellular signaling from a control PAR-I not exposed to the "antagonist."

An "agonist" or "antagonist" compound as used herein, may comprise one or more protecting groups that prevent undesirable reactions (such as proteolysis) involving unprotected functional groups. In one embodiment, the present invention contemplates that the protecting group is an acyl or an amide. In one embodiment, the acyl is acetate. In another embodiment, the protecting group is a benzyl group. In another embodiment, the protecting group is a benzoyl group. The present invention also contemplates combinations of such protecting groups.

As used herein, "anti-coagulant" drugs refer to drugs that prevent coagulation; i.e. that stop blood from clotting. Non-limiting examples of anti-coagulants that may be used in this invention include, for example, coumarines (vitamin K antagonists, Warfarin (Coumadin, Acenocoumarol, Phenprocoumon) and synthetic pentasaccharide inhibitors of factor Xa (Fondaparinux or Idraparinux).

As used herein. "anti-platelet drugs" refer to members of a class of pharmaceuticals that decreases platelet aggregation. Non-limiting examples of anti-platelet drugs include, for example, cyclooxygenase inhibitors (Aspirin), adenosine diphosphate (ADP) receptor inhibitors (Clopidogrel (Plavix), Ticlopidine (Ticlid)), phosphodiesterase inhibitors (Cilostazol (Pletal), glycoprotein IIB/IIIA inhibitors and adenosine reuptake inhibitors (Dipyridamole (Persantine)). In one embodiment, an antiplatelet drug comprises SCH 530348.

As used herein, "glycoprotein IIB/IIIA inhibitors" include, but are not limited to, (Abciximab (ReoPro), Eptifibatide (Integrilin) and Tirofiban (Aggrastat), Defibrotide. Abciximab (previously known as c7E3 Fab), manufactured by Centocor and distributed by Eli Lilly under the trade name ReoPro, is a platelet aggregation inhibitor mainly used during and after coronary artery procedures like angioplasty to prevent platelets from sticking together and causing thrombus (blood clot) formation within the coronary artery. Eptifibatide (Integrilin, Millennium Pharmaceuticals, also co-promoted by Schering-Plough/Essex), is an antiplatelet drug that selectively blocks the platelet glycoprotein IIb/IIIa receptor. Eptifibatide is a cyclic heptapeptide derived from a protein found in the venom of the southeastern pygmy rattlesnake (*Sistrurus miliarius barbouri*). It belongs to the class of the so called arginin-glycin-aspartat-mimetics and reversibly binds to platelets. Eptifibatide has a short half-life. The drug is the third inhibitor of GPIIb/IIIa that has found broad acceptance after the specific antibody abciximab and the non-peptide tirofibanentered the global market. Tirofiban is a synthetic, non-peptide inhibitor acting at glycoprotein (GP) IIb/IIIa receptors in human platelets. It therefore constitutes an anticoagulant, specifically an inhibitor of platelet aggregation. The drug is marketed under the brand name AGGRASTAT in the US by Medicure Pharma and the rest of the world by Iroko Pharmaceuticals.

The term "attached" as used herein, refers to any interaction between a medium (or carrier) and an agent, e.g. an agonist or antagonist of the MMP-1 mediated PAR-1 signaling pathway. Attachment may be reversible or irreversible. Such attachment includes, but is not limited to, covalent bonding, and non-covalent bonding including, but not limited to, ionic bonding, Van der Waals forces or friction, and the like. An agent is attached to a medium (or carrier) if it is impregnated, incorporated, coated, in suspension with, in solution with, mixed with, etc.

As used herein, a medical device is "coated" when a medium comprising an agent, e.g., an agonist or antagonist of the MMP-1 mediated PAR-1 signaling pathway, becomes attached to the surface of a medical device. This attachment may be permanent or temporary. When temporary, the attachment may result in a controlled release of the agent. Medical devices may be coated with a thin polymer film loaded with the agent that inhibits platelet activation. The coating is applied to the medical device prior to insertion into a blood vessel using methods well known in the art, such as a solvent evaporation technique. The solvent evaporation technique entails mixing a polymer and agent in a solvent. The solution comprising polymer, agent, and solvent can then be applied to the surface of the medical device by either dipping or spraying. The medical device is then subjected to a drying process, during which the solvent is evaporated, and the polymeric material, with the agent dispersed therein, forms a thin film layer on the medical device. U.S. Pat. No. 5,837,313 to Ding et al. describes a method of preparing a heparin containing coating composition. U.S. Pat. No. 5,525,348 Whitbourne discloses a method of complexing pharmaceutical agents (including heparin) with quarternary ammonium components or other ionic surfactants and bound with water insoluble polymers as an anti-thrombotic coating composition. A general approach to the coating of medical devices as disclosed in US 2005/0191333 A1. US 2006/0204533 A1, and WO 2006/099514 A2, all by Hsu, Li-Chien, et al., uses a low molecular weight complex of heparin and a counter ion (stearylkonium heparin), or a high molecular weight polyelectrolyte complex, such as dextran, pectin to form a complex.

The term "collagen-induced platelet aggregation", as used herein, refers to platelet aggregation in response to the presence of the protein, collagen.

A "homologue" of a MMP-1 polypeptide refers to a polypeptide having at least about 80%, preferably at least about 85%, more preferably at least about 90%, most preferably at least about 95% amino acid sequence identity with human MMP-1 of amino acid sequence UniProtKB/Swiss-Prot P03956 (MMP1_HUMAN), which is incorporated herein by reference. In one embodiment, for example, a MMP-1 homologue includes those variants that are capable of cleaving PAR-1 between aspartic acid at position 39 (D39) and proline at position 40 (P40).

A "homologue" of a PAR-1 polypeptide refers to a polypeptide having at least about 80%, preferably at least about 85%, more preferably at least about 90%, most preferably at least about 95% amino add sequence identity with the human PAR-1 polypeptide sequence with Genbank Accession No. NP_001983. In one embodiment, for example, a PAR-1 homologue includes those PAR-1 variants that can be cleaved between aspartic acid at position 39 (D39) and proline at position 40 (P40).

The term, "inhibiting platelet activation", as used herein, refers to decreasing or slowing platelet aggregation, as well as completely eliminating and/or preventing platelet aggreagtion.

The term "ligand-binding", as used herein, refers to a member of a binding pair, i.e., two different molecules wherein one of the molecules specifically binds to the second molecule through chemical or physical means. In addition to antigen and antibody binding pair members, other binding pairs include, as examples without limitation, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), and the like. Furthermore, binding pairs can include members that are analogs of the original binding member, for example, an analyte-analog or a binding member made by recombinant techniques or molecular engineering. If the binding member is an immunoreactant it can be, for example, a monoclonal or polyclonal antibody, a recombinant protein or recombinant antibody, a chimeric antibody, a mixture(s) or fragment(s) of the foregoing, as well as a preparation of such antibodies, peptides and nucleotides for which suitability for use as binding members is well known to those skilled in the art. A ligand-binding member may be a polypeptide affinity ligand (see, for example, U.S. Pat. No. 6,326,155, the contents of which are hereby incorporated by reference herein in its entirety). In one embodiment, the ligand-binding member is labeled. The label may be selected from a fluorescent label, a chemiluminescent label or a bioluminescent label, an enzyme-antibody construct or other similar suitable labels known in the art.

In some embodiments, a ligand-binding molecule refers to an "antibody" including both polyclonal and monoclonal antibodies; and may be an intact molecule, a fragment thereof (such as Fv, Fd, Fab, Fab' and F(ab)'2 fragments, or multimers or aggregates of intact molecules and/or fragments; and may occur in nature or be produced. e.g., by immunization, synthesis or genetic engineering. An antibody may be humanized according to methods that are well known in the art.

In another embodiment, a "ligand-binding molecule" may refer to an "aptamer," i.e. oligonucleotides that are able to bind a target of interest other than by base pair hybridization.

As used herein, a "matrix layer" refers to the substance, such as a polymer, that is suitable for attaching the herein described "agonist" or "antagonist" and can be applied to the surface of a medical device. Methods of coating a medical device are described in U.S. Patent Publication No. 2009/0018646, the contents of which are hereby incorporated herein in their entirety.

The term "medical device", as used herein, refers broadly to any apparatus used in relation to a medical procedure. Specifically, any apparatus that comes in contact with a patient's blood during a medical procedure or therapy is contemplated herein as a medical device. Similarly, any apparatus that administers a drug or compound to a patient during a medical procedure or therapy is contemplated herein as a medical device. "Direct medical implants" include, but are not limited to, urinary and intravascular catheters, dialysis catheters, wound drain tubes, skin sutures, vascular grafts and implantable meshes, intraocular devices, implantable drug delivery systems and heart valves, and the like. "Wound care devices" include, but are not limited to, general wound dressings, non-adherent dressings, burn dressings, biological graft materials, tape closures and dressings, surgical drapes, sponges and absorbable hemostats. "Surgical devices" include, but are not limited to, surgical instruments, endoscope systems (i.e., catheters, vascular catheters, surgical tools such as scalpels, retractors, and the like) and temporary drug delivery devices such as drug ports, injection needles etc. to administer the medium.

Matrix metalloproteinase-1 (MMP-1, aliases: CLG, CLGN, EC 3.4.24.7) is also known as fibroblast collagenase, interstitial collagenase, matrix metallopeptidase-1 or matrix metalloprotease-1 (HGNC: 71551; Entrez Gene: 43122; UniProtKB: P039563; Ensembl: ENSG000001966117; GenBank Accession Number: NM_002421). The MMP-1 gene encodes a secreted enzyme that can break down interstitial collagens, types I, II, and III. The gene is part of a duster of MMP genes, which localize to human chromosome 11q22.3.

Matrix metalloprotease-2 (MMP-2; aliases: CLG4, CLG4A, EC 3.4.24.24, MMP-II, MONA, TBE-1) is also known as 72 kDa gelatinase, gelatinase A, matrix metalloproteinase-2, collagenase type IV-A, matrix metallopeptidase 2, 72 kDa type IV collagenase or neutrophil gelatinase (HGNC: 71661; Entrez Gene: 43132; UniProtKB: P082533; Ensembl: ENSG000000872457).

As used herein, "metalloprotease" or "MMP" refers to a family of calcium- and zinc-dependent endopeptidases that share amino-acid sequences, structural domains, and overlapping substrates. These enzymes are secreted as zymogens and removal of an activation peptide is required for their proteolytic activity. MMPs are involved in the breakdown of components of the extracellular matrix (ECM) and basement membrane such as aggrecan, collagen, elastin, fibronectin, gelatin, and laminin. The ability of MMPs to degrade components of the ECM is essential to cell growth, cell division, bone growth, wound healing, embryogenesis, and angiogenesis. The MMPs are divided into several different classes. They are referred to numerically as MMP-1, MMP-2. etc. as well as by a common name. The MMPs share several structural and functional properties but differ in their substrate specificities. There are at least 25 members of the MMP family, categorized based on their domain structures and their preferences for macromolecular substrates (Nelson, A. et al., (2000) J. Clin. Onool. 18, 1135-1149, Woessner, J. F., and Nagase, H. (2000) Matrix Metalloproteinases and TIMPs, Oxford University Press, Oxford). Most MMPs contain a propeptide domain, a catalytic domain, and a hemopexin/vitronectin-like domain (Woessner, J. F., and Nagase, H., supra). The MMP family includes MMP-1 (interstitial cotlagenase, collagenase 1), MMP-2 (gelatinase A), MMP-3 (stromelysin 1), MMP-7 (pump 1, matrilysin), MMP-8 (neutrophil collagenase, collagenase 2), MMP-9 (gelatinase B), MMP-10 (stromelysin 2), MMP-11 (stromelysin 3), MMP-12 (metalloelastase, macrophage elastase). MMP-13 (collagenase 3), five membrane-type MMPs (MT-MMPs) (MMP-14, MMP-15, MMP-16, MMP-17, MMP-21), MMP-18 (*Xenopus* collagenase 4), MMP-19, MMP-20 (enamelysin), MMP-22 (chicken CMMP), MMP-23, MMP-24, MMP-25, MMP-26 (endometase). MMP-27, and MMP-28 (epilysin). Some redundancy of MMP family member numbering exists: telopeptidase, later designated MMP-4, and 3/4-collagenase (MMP-5) are MMP-3 and MMP-2, respectively; MMP-6 (acid metalloproteinase) was shown to be MMP-3.

In this disclosure, reference to metalloproteases in general or to any individual member of the MMP family, such as MMP-1 or MMP-2, will be understood to refer to all splice variants, mutants (including, but not limited to, deletions, insertions or polymorphisms or amino acid substitutions), isoforms and homologues thereof.

As used herein, to "modulate" means to act as an antagonist, i. e. partially or fully inhibit, reduce, alleviate, block or prevent; or to increase or stimulate, i. e. to act as an agonist. The modulation may be direct or indirect.

Non-encoded amino acids include, but are not limited to, alpha-amino acids, beta-amino acids, gamma-amino acids, delta-amino acids, and omega-amino acids, and may have R or S chirality at any chiral atom. Non-encoded amino acids include isomers of the encoded amino acids such as, e.g., stereoisomers (including, e.g., D-amino acids and allo-amino acids such as, e.g., allo-threonine and allo-isoleucine) and structural isomers (including, e.g., beta-alanine) of the encoded amino acids. Non-encoded amino acids also include N-methylated amino acids. In general, where no specific configuration is indicated for an alpha-amino acid, one skilled in the art would understand that amino acid to be an L-amino acid. However, in particular embodiments, non-encoded amino adds may also be in the form of racemic, non-racemic, and diastereomeric mixtures. Non-encoded amino acids are well known in the peptide art and include, but not limited to, N-acetytserine, alpha//o-isoleucine, alpha//o-threonine, beta-alanine (3-aminopropionic acid), alpha-aminoadipic acid, 2-aminobutanoic acid, 4-aminobutanoic acid, 3-amino-1-carboxymethylvalerolactam, 1-aminocyclopentanecarboxylic acid, 6-aminohexanoic acid, 2-aminoheptanedioic acid, 7-aminoheptanoic acid, 2-aminoisobutyric acid, aminomethylpyrrole carboxylic acid, 8-amino-3,6-dioxa-octanoic acid, aminopiperidinecarboxylic acid, aminoserine, aminotetrahydropyran-4-carboxylic acid, azetidine carboxylic acid, benzothiazolylalanine, butylglycine, carnitine, 4-chlorophenylalanine, citrulline, cyclohexylalanine, cyclohexylstatine, 2,4-diaminobutanoic acid, 2,3-diaminopropionic acid, dihydroxyphenylalanine, dimethylthiazolidine carboxylic acid, 4-guanyl-phenylalanine, homoarginine, homocitrulline, homocysteine, homophenylalanine, homoproline, homoserine, 4-hydrazinobenzoic acid, 4-hydroxyproline, isonipecotic acid, methanoproline, norleucine, norvaline, ornithine, p-aminobenzoic acid, penicillamine, phenylglycine, (9-phosphoserine, piperidinylalanine, piperidinylglycine, pyrrolidinylalanine, sarcosine, statine, tetrahydropyranglycine, thienylalanine, [epsiv]-N,N,N-trimethyllysine.

The Human PAR family includes PAR-1 (Genbank Accession Number AF019616); PAR2 (Genbank Accession Number XM-003671); PAR3 (Genbank Accession Number NM-0041101); and PAR4 (Genbank Accession Number NM-003950.1), the sequences of which are hereby incorporated by reference.

PAR-1 or protease activated receptor 1 (other aliases: CF2R, HTR 2, PAR1 or TR) is also known in the art as thrombin receptor or coagulation factor II (thrombin) receptor (HGNC: 35371; Entrez Gene: 21492; UniProtKB: P251163; Ensembl: ENSG000001811047). The human PAR-1 polypeptide sequence has Genbank Accession No. NP_001983, which is also incorporated herein by reference and also reproduced in FIG. 9B.

In this disclosure, reference to PAR family members in general or to any individual member of the PAR family member, such as PAR-1, will be understood to refer to all splice variants, mutants (including, but not limited to, deletions, insertions or polymorphisms or amino acid substitutions), isoforms and homologues thereof.

The term, "patient," as used herein, refers to any individual organism. For example, the organism may be a mammal such as a primate (i.e., for example, a human). Further, the organism may be a domesticated animal (i.e., for example, cats, dogs, etc.), livestock (i.e., for example, cattle, horses, pigs, sheep, goats, etc.), or a laboratory animal (i.e., for example, mouse, rabbit, rat, guinea pig, etc.).

As used herein, "platelet activation" refers to the series of changes in platelet function that ultimately leads to platelet aggregation and the formation of a stable haemostatic plug or "thrombus." Platelet activation can be triggered by vascular injury caused, for example, by the rupture of atherosclerotic plaque. The subsequent exposure of circulating platelets to the sub-endothelial tissue and various platelet activation molecules, such as collagen, thromboxane or ADP, initiates a chain of events that results in changes to platelet metabolic biochemistry, shape, surface receptors, and membrane phospholipid orientation and thrombus formation.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pepducin lipopeptides" are cell-penetrating peptides that act as intracellular inhibitors of signal transference from receptors to G proteins. Pepducin lipopeptides utilize lipidated fragments of intracellular G protein-coupled receptor loops to modulate GPCR action in targeted cell-signaling pathways. A pepducin lipopeptide molecule comprises a short peptide derived from a GPCR intracellular loop tethered to a hydrophobic moiety. This structure allows pepducin lipopeptides to anchor in the cell membrane lipid bilayer and target the GPCR/G protein interface via a unique intracellular allosteric mechanism. Examples of pepducin lipopeptides are described in U.S. Patent Publication US2007/0179090, the contents of which are hereby incorporated herein by reference in its entirety.

As used herein, the term "peptide" or "polypeptide" is intended to encompass a single "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. A "peptide" or "polypeptide," as used herein, may be derived from a natural biological source or produced by recombinant technology, but is not necessarily translated from a designated nucleic acid sequence. It may be generated in any manner, including by chemical synthesis. In accordance with this definition, a "peptide" or "polypeptide" used in the present invention may be of a size of about 3 or more, about 5 or more, about 10 or more, about 20 or more, about 25 or more, about 50 or more, about 75 or more, about 100 or more, about 200 or more, about 500 or more, about 1,000 or more, or about 2,000 or more amino acids. One or more of the amino acids in an inventive polypeptide may be modified, for example, by the addition of a chemical entity such as a carbohydrate group, a phosphate group, a farnesyl group, an isofarnesyl group, a fatty acid group, an acyl group (e.g., acetyl group), a linker for conjugation, functionalization, or other known protecting/blocking groups. In a preferred embodiment, the modifications of the peptide lead to a more stable peptide (e.g., greater half-life in vivo).

A "peptide" or "polypeptide," as used herein, may be fragments, derivatives, analogs, or variants of the foregoing polypeptides, and any combination thereof. Fragments of polypeptides, as that term or phrase is used herein, include proteolytic fragments, as well as deletion fragments. Variants of polypeptides, useful in accordance with the present invention, include fragments and polypeptides with altered amino acid sequences due to amino acid substitutions, deletions, or insertions. Variants may occur naturally or be non-naturally occurring. Non-naturally occurring variants may be produced using art-known mutagenesis techniques. Examples include fusion proteins, polypeptides having one or more residues chemically derivatized by reaction of a functional side group, and peptides that contain one or more naturally occurring amino acid derivatives of the twenty standard amino acids. These modifications may also include cyclization of the peptide, the incorporation of D-amino acids, or other non-encoded amino-acids. None of the modifications should substantially interfere with the desired biological activity of the peptide.

As used herein, a "reduction in the size of atherosclerotic plaque" refers to the reduction in size of atherosclerotic plaque as a result of treatment with an antagonist of the MMP-1 mediated PAR-1 signaling pathway as compared to the size of atherosclerotic plaque before the onset of treatment. The artherosclerotic plaque is reduced in size if the reduction is at least or at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, about 100%, about 200%, about 500% or more as compared to the size of atherosclerotic plaque before the onset of treatment.

As used herein, "risk factors" for venous thromboembolism include, but are not limited to, cancer, prior VTE (DVT/PE), hypercoagulability (genetic predisposition for blood dots), surgery, advanced age (>70 years of age), obesity (BMI>29), bed rest, or prolonged immobility and oral contraceptives or hormone replacement therapy.

As used herein, "risk factors" for myocardial infarction, stroke or PAD (Peripheral Arterial Disease) include, but are not limited to, high blood pressure, diabetes, high cholesterol (including genetic predisposition to hypercholesteremia), age (risk doubles for each decade over 55 years of age), family history of stroke, smoking, oral contraceptives, atrial fibrillation, heart failure, excess alcohol, prior stroke or heart attack, race (for example, African Americans have almost twice the risk of first-ever stroke compared with Caucasians) and gender (each year, in the U.S. about 46,000 more women than men have a stroke).

In other embodiments, "risk factors" for thrombosis also refer to those risks created by the implantation of a prosthesis inside the body, including, but not limited to, artificial hearts, lungs as well as stents or other medical devices.

As used herein, the term "small molecule" and analogous terms include, but are not limited to, peptides, peptidomimetics, amino acids, amino acid analogs, polynucleotides, polynucleotide analogs, nucleotides, nucleotide analogs, other organic and inorganic compounds (i.e., including heteroorganic and organometallic compounds) having a molecular weight less than about 10,000 grams per mole. In some embodiments, the term refers to organic or inorganic compounds having a molecular weight less than about 5,000 grams per mole, less than about 1,000 grams per mole, less than about 500 grams per mole, less than about 100 grams per mole. Salts, esters, and other pharmaceutically acceptable forms of such compounds are also encompassed.

As used herein, "thrombolytic drugs" refer to drugs that are used in medicine to dissolve blood dots in a procedure termed thrombolysis. Non limiting examples of thrombolytic drugs include # tissue plasminogen activator—t-PA—alteplase (Activase), reteplase (Retavase), tenecteplase (TNKase), anistreplase (Eminase), streptokinase (Kabikinase, Streptase) and urokinase (Abbokinase).

As used herein, a "thrombotic disease state" refers to any medical condition in a patient that can lead to thrombosis i.e. the formation of a blood dot or "thrombus" inside a blood vessel, obstructing blood flow through the circulatory system. There are two distinct forms of thrombosis: venous and arterial thrombosis. Venous thromboembolism (VTE), which is comprised of deep vein thrombosis (DVT) and pulmonary embolism (PE), and thoracic outlet syndrome are examples of venous thrombosis. Stroke, heart attack, and peripheral arterial disease are examples of arterial thrombosis. Further examples of a thromboembolic disorder include, but are not limited to, unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease (PAD), venous thrombosis, deep vein thrombosis, thrombophlebitis, arterial embolism, coronary arterial thrombosis, cerebral arterial thrombosis, cerebral embolism, kidney embolism, pulmonary embolism, thrombotic re-occlusion subsequent to a coronary intervention procedure, heart surgery or vascular surgery and thrombosis resulting from medical implants, devices, or procedures in which blood is exposed to an artificial surface that promotes thrombosis. The "thrombotic disease state" also refers to cardio-vascular disease resulting from systemic diseases including, but not limited to, diabetes mellitus, syndrome X (metabolic syndrome) or cancer.

The term "therapeutically effective amount" as used herein means that amount of active compound or pharmaceutical "agent" that elicits the biological or medicinal response in a tissue, system, animal or human that is being sought by a researcher, veterinarian, medical doctor or other clinician.

As used herein, "thrombin-dependant activation of PAR-1" refers to the activation of PAR-1 signaling by a serine protease (such as thrombin or plasmin or APC) that cleaves the N terminus of PAR-1 between the arginine residue at position 41, and the serine residue at position 42.

As used herein, "treating" or "treatment" cover the treatment of a thrombotic disease-state in a mammal, particularly in a human, and include, but not limited to: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The term, "treating a thrombotic disease state," as used herein, refers to modulating platelet aggregation including, but not limited to, decreasing the amount of platelet aggregation and/or slowing platelet aggregation, as well as completely eliminating and/or preventing platelet aggregation. Diseases and/or conditions treatable by modulating platelet aggregation include, but are not limited to, embolus formation, thrombolytic complications, thrombosis, coronary heart disease, thromboembolic complications, myocardial infarction, restenosis, atrial thrombosis induction of atrial fibrillation, chronic unstable angina, transient ischemic attacks and strokes, peripheral vascular disease, arterial thrombosis, preeclampsia, embolism, restenosis and/or thrombosis following angioplasty, carotid endarterectomy, anastomosis of vascular grafts, and chronic exposure to cardiovascular devices. Such conditions may also result from thromboembolism and re-occlusion during and after thrombolytic therapy, after angioplasty, and after coronary artery bypass.

I. The MMP-1-PAR-1 Signalling Pathway
I-(A) Collagen Generates Active MMP-1 on Platelets which Cleaves the Par-1

Human platelets contain significant amounts of collagenase activity, which could be released upon exposure to various agonists. The major platelet collagenase $\beta_3$ may be able to prime the aggregatory response to other agonists and cause redistribution of the N3 integrins to the cell periphery. To determine if the pro-aggregatory effects of platelet MMP-1 are mediated by the PAR1 receptor, the amount of in situ activation of endogenous proMMP-1 on the platelet surface was measured following stimulation with the primary agonist collagen versus the secondary mediators, ADP and thromboxane.

Platelet pellets and their supernatants were prepared as follows. The IRB of Tufts Medical Center performed phlebotomy on 20 healthy volunteer donors following established informed consent procedures. 27 ml of blood was drawn using an 18 gauge needle attached to a 30 cc syringe containing 3 ml of 3.2% sodium citrate solution (0.32% v/v final). Platelets from platelet-rich plasma (PRP) were isolated by gel filtration using a Sepharose 2B (Pharmacia) in modified PIPES buffer (25 mM PIPES, 137 mM NaCl, 4 mM KC, 0.1% Glucose, pH 6.6) in the presence of 1 mM EDTA and 0.1 U/ml of apyrase. Alternatively, whole blood was obtained from Hartley Sprague guinea pigs (drawn from the vena cava) into 3% citrate plus 10 U/ml heparin. Washed platelets from the guinea pigs were prepared in PIPES buffer. Platelet aggregation was measured with a Chronolog 560VS/490-2D aggregometer using modified PIPES buffer as a blank. Samples were incubated for 5 min in the presence of inhibitors and 1.8 mM $CaCl_2$ prior to addition of agonist. All reactions were in final volumes of 250 µl at 37° C. while stirring at 900 rpm.

The enzymatic activity of active MMP-1 in supernatants and platelet lysates was then determined. Human or guinea pig platelets from PRP were concentrated four-fold by centrifugation at 700 g for 25 min at room temperature, and then resuspended in 0.25 volume of PIPES containing 1 mM EDTA (final platelet count was $10^9$/mL). Platelets were treated with PBS (buffer), 20 µM ADP, 20 µM U-46619, or 20 µg/ml collagen in the presence of 2.5 mM $CaCl_2$. The platelets were incubated for 15 min at 37° C. with occasional gentle mixing. Platelets were collected by centrifugation at 10,000 g for 5 min at 4° C. and resuspended in lysis buffer (50 mM Tris HCl, 100 mM NaCl, 1 mM NaF, 5 mM EDTA, 0.1% (v/v) Triton X-100, 100 µM PMSF, pH 7.4) and then sheared with a 27 gauge needle.

The enzymatic activity of active MMP-1 in supernatants and platelet lysates was measured using DQ collagen I (Molecular Probes) as fluorogenic substrate and reporter of collagenase activity substrate (Boire et al., 2005) in the presence or absence of 3 µM FN-439, or 20 µg/ml each of control IgG, MMP-1 blocking Ab, MMP-8 blocking Ab or MMP-13 blocking Ab (preincubated for 2 h at 37° C.), as indicated with APMA-activated MMP-1 serving as control (FIG. 1A, striped bars). A standard curve generated with APMA-activated MMP-1 (Boire et al., 2005) and collagenase activity was reported in units per milliliter, where one unit is the amount of MMP-1 degrading 1 µg of collagen per minute.

Stimulation of platelets with collagen leads to the release of the platelet collagenase activity into the supernatant (FIG. 1A). The MMP-1 inhibitor, FN-439 completely blocked cleavage of the fluorogenic collagen substrate. Blocking antibodies against MMP-1 also completely inhibited the platelet collagenase activity released by collagen, whereas blocking antibodies against the two other collagenases, MMP-8 and MMP-13 or an IgG control had no effect. Stimulation of gel-filtered platelets with ADP or the thromboxane mimetic. U-46619, however, resulted in a majority of the MMP-1 collagenase activity remaining bound to the platelet.

Pellets and supernatants were collected from platelets (250,000/µL) stimulated with the agonists as described above and in FIG. 1A or with convulxin (1 µg/ml) by centrifuging the lysate at 12,000 g for 2 min. The concentration of the released and platelet-associated MMP-1 pro-domains was then measured by ELISA using antibodies that recognized the pro domain of MMP-1 (FIG. 1B). Treatment of washed platelets with collagen but not ADP or U-46619 led to efficient release of the proMMP-1 domain (and/or proMMP-1).

Surface expression of total platelet MMP-1 was then determined by flow cytometry (FIG. 1C; dashed grey: secondary antibody alone; solid lines: FACS profiles of platelets treated with the indicated concentrations of collagen for 15 min at 37° C. and then stained with primary (AB806) plus secondary antibodies). FACS analysis confirmed that MMP-1 is expressed on the surface of resting platelets, which could be released by exposure to collagen The lectin, convulxin, which ligands specifically with the GPVI/FcγR collagen receptor, also caused full release of the proMMP-1 domain from the platelet surface (FIG. 1B). Thus, collagen fibrils per se are not necessary for the release of pro-MMP-1 from the platelet surface. Other strong platelet agonists may also trigger the release mechanism.

One candidate binding site(s) for the platelet-associated proMMP-1 is the $\alpha_2\beta_1$ collagen receptor. To determine if proMMP-1 associates with integrins in resting human platelets, lysates from gel-filtered platelets were incubated with 4-5 μg/ml anti-$\alpha_2$ (Gi9 or AK7), $\beta_1$ (MAB1987), $\beta_3$ (MAB1957), GPVI (SC20149), GPIBα (MM2/174) or mouse IgG control for 2-4 h at 4° C. Protein G sepharose was added and incubated for an additional 1 h. Beads were collected and washed 4× in lysis buffer supplemented with 200 mM NaCl. Platelet proteins from the lysates were separated by 12% SDS-PAGE and Western analyses were conducted using a polyclonal Ab against the C-terminus of MMP-1 (AB8105) or the hinge region (AB806) which gave similar results. These co-immunoprecipitation experiments indicate that proMMP-1 forms a stable complex with the $\alpha_2\beta_1$ integrin on platelets (see FIG. 1D). MMP-1 (predominantly in the pro form) was also found to associate with the $\alpha_{IIb}\beta_3$ integrin, as suggested by previously described co-focal microscopy studies. Conversely, proMMP-1 did not associate with GPIbα or GPVI. Therefore, proMMP-1 is likely to be pre-associated with both collagen and fibrinogen receptors in resting platelets.

Figures 1D, 1E, 1F, 1G, 1H, 1I:
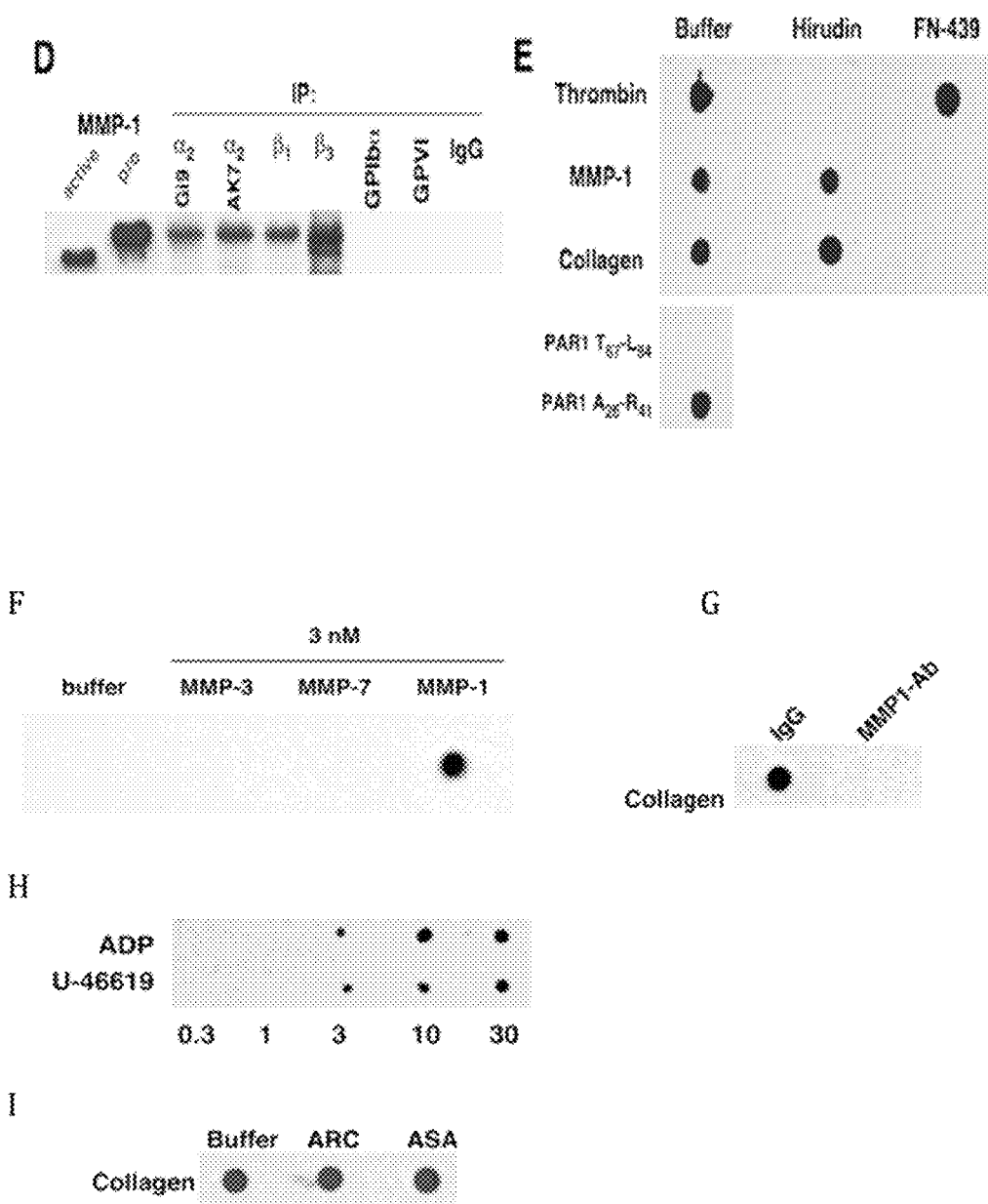
FIG. 1D shows proMMP-1 associates with integrins in resting human platelets.
FIG. 1E shows MMP-1 and collagen cause the release of an N-terminal thrombin-deavage fragment from the extracellular domain of PAR1.
FIG. 1F depicts a dot blot analysis that shows MMP-3 and MMP-7 are unable to release a N-terminal PAR-1 peptide from resting platelets.
FIG. 1G depicts a dot blot analysis that shows a MMP-1 specific antibody can block the collagen-induced release of the N-terminal PAR-1 peptide from resting platelets.
FIG. 1H depicts a dot blot analysis that shows ADP and U-46619 can promote the release of the N-terminal PAR-1 peptide from resting platelets.
FIG. 1I depicts a dot blot analysis that shows blocking either the P2Y12 ADP. receptor with AR-C69931MX (ARC) or thromboxane with aspirin (ASA) had no effect on the collagen-dependent release of the PAR1 N-terminal peptide.

To further understand how collagen is able to activate significant amounts of endogenous MMP-1 collagenase activity on the surface of platelets, experiments were devised to determine if PAR-1 is cleaved in either an autocrine or paracrine manner following exposure to collagen. Using a monoclonal antibody raised against the amino-terminal thrombin-cleavage peptide region of PAR1, residues 32-46 (Loew et al., 2000), the relative abilities of thrombin, MMP-1 and collagen to cause cleavage of platelet PAR1 was assessed. Gel filtered platelets were treated for 10 min with thrombin (3 nM), MMP-1 (3 nM), collagen (5 μg/ml), in the presence or absence (PBS buffer) of 0.00013 U hirudin or 5 μM FN-439 at 37° C. Supernatants were concentrated 20-fold and applied to nitrocellulose membranes, then probed with the IIaR-A monoclonal antibody. The PAR1 N-terminal thrombin deavage peptide ($A_{26}$-$R_{41}$) and PAR1 flexible linker peptide (N-acetyl-$T_{67}$-$L_{84}$ -C) (Kuliopulos et al., 1999) served as positive and negative controls (100 ng), respectively. As shown in FIG. 1E, incubation of platelets with thrombin or MMP-1 was able to cause release of the N-terminal cleavage peptide of PAR1 into the supernatant, which was blocked by hirudin or FN-439, respectively.

To determine if MMP-3 and MMP-7 could cause the release of the PAR1 N-terminal peptide, gel filtered human platelets were treated for 10 min with APMA-dialysate buffer or APMA activated MMP-3 (Chemicon, 3 nM), MMP-7 (Chemicon, 3 nM) or MMP-1 (Biomol, 3 nM). Platelet pellet and supernatant were separated as described above. Supernatants were concentrated 20-fold and applied to nitrocellulose membranes, then probed with the IIaR-A monoclonal antibody to detect cleaved PAR-1 peptide. As shown in FIG. 1F, MMP-3 and MMP-7 were not able to cause release of the PAR1 N-terminal peptide from the treated platelets (FIG. 1F).

To demonstrate the role of MMP-1, gel filtered platelets were pre-incubated with IgG (20 μg/ml) or MMP-1 blocking antibody (20 μg/ml) for 2 hrs at 37° C. These platelets were then stimulated with collagen (5 μg/ml) for 10 min. at 37° C. Supernatants were concentrated 20-fold and applied to nitrocellulose membranes, then probed with the IIaR-A monoclonal antibody. As shown in FIG. 1G, treatment of the resting platelets with collagen led to the release of the N-terminal peptide. This release was specifically blocked by incubation with the MMP-1 inhibitor. FN-439, or an MMP1-blocking antibody (20 μg/ml) but not by thrombin inhibitor, hirudin (see FIG. 1E, FIG. 1G).

Treatment of the gel filtered platelets for 10 min at 37° C. with different concentrations of ADP (0.3-30 nM), U46619 (0.3-30 nM) followed by incubation with collagen (5 μg/ml) for 10 min. at 37° C. showed that ADP and U-46619 were also able to cause the release of the N-terminal peptide of PAR1 albeit at lower efficiency (see FIG. 1H).

On the contrary, treatment of the gel filtered platelets for 10 min with collagen (5 μg/ml), in the presence or absence (PBS buffer) of ARC (0.5 μM) or aspirin (ASA, 1 mM, 30 min pro-incubation) at 37° C. failed to release the PAR1 N-terminal peptide (see FIG. 1I). Hence, blocking either the P2Y12 ADP receptor with AR-C69931MX (ARC) or thromboxane with aspirin (ASA) had no effect on the collagen-dependent release of the PAR1 N-terminal peptide (see FIG. 1I).

Together, these data provide direct evidence that the endogenously-generated MMP-1 collagenase activity is able to cleave PAR1 on the surface of human platelets independently of thrombin.

I-(B) Identification of the MMP-1 Cleavage Site on PAR1

Figures 2A, 2B:
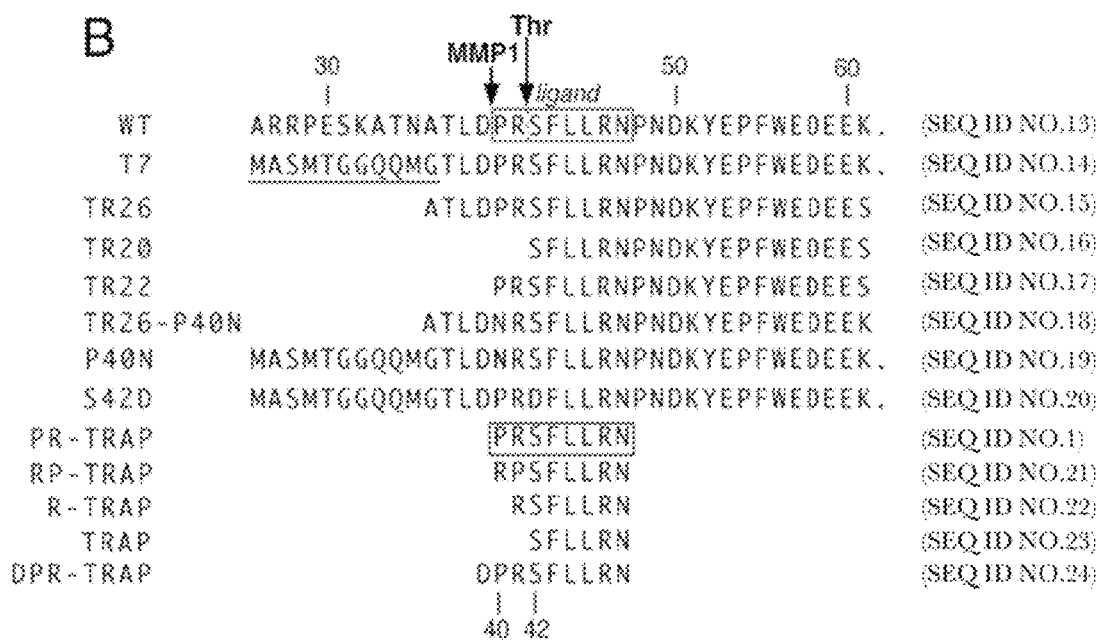
FIG. 2A shows the identification of the MMP-1 cleavage site on the TR26 N-terminal peptide region of PAR1.
FIG. 2B shows the location of the cleavage of PAR1 N-terminal extracellular mutants by thrombin and MMP-1.

Several studies have demonstrated that serine proteases such as thrombin, plasmin and APC directly hydrolyze PAR1 at $LDPR_{41}\downarrow S_{42}$ FL (P4P3P2P1↓P1'P2'P3') to generate the $S_{42}$FLLRN-tethered ligand (TRAP), which activates PAR1 in an intramolecular mode (Kuliopulos et al., 1999; Loew et al., 2000; Parry et al., 1996: Seeley et al., 2003; Vu et al., 1991). However, matrix metalloproteases such as MMP-1 generally prefer a hydrophobic amino acid at the P1' site, a basic or hydrophobic amino acid at P2', and a small residue (alanine, glycine or serine) at P3' (Netzel-Arnett et al., 1991; Turk et al., 2001). Therefore, MMP-1 may not efficiently cleave at the $R_{41}\downarrow S_{42}$FL thrombin site. To determine the MMP-1 cleavage site, a 26 amino acid peptide (TR26, PAR1 residues 36-61) was synthesized corresponding to the N-terminal domain of PAR1 (FIGS. 2A-B). The synthetic 26mer peptides encompassing the thrombin deavage site region and flanking region, TR26 ($A_{36}$-$S_{81}$) or TR26-P40N ($A_{36}$-$K_{81}$), were incubated with 10 nM thrombin, 10 nM MMP-1 (APMA activated, purified from human fibroblasts) or PBS buffer for 10 min at 37° C. Peptide cleavage mixtures were separated by RP-HPLC and cleavage products identified by MALDI-mass spectroscopy as described (Kuliopulos 1999). Incubation of the TR26 peptide with thrombin yielded the expected cleavage peptide, TR20 (residues 42-61), as determined by mass spectrometry. In contrast, incubation of the TR26 peptide with MMP-1 yielded TR22, which corresponds to PAR1 residues 40-61 (FIG. 2A-B). This indicates that MMP-1 cleaves the PAR1 exodomain at $LD_{39}\downarrow P_{40}$RSFL, a site which is located 2-amino acid residues to the N-terminal side of the thrombin cleavage site at $R_{41}$-$S_{42}$.

To verify the location of this putative MMP-1 cleavage site in the full-length receptor, the critical P1' residues of both the MMP-1 and thrombin cleavage sites were mutated.

To inhibit cleavage by MMP-1, the putative P1' proline was replaced with asparagine (P40N PAR1), a substitution which had previously been shown to reduce cleavage of α1 collagen peptides to less than 10% (Berman et al., 1992). To inhibit proteolysis by thrombin, the P1' serine of the thrombin cleavage site was mutated to aspartate (S42D PAR1), a mutation which was anticipated to suppress cleavage by thrombin (Chang, 1985). Human PAR1 was cloned into pcDEF3 as described previously (Kuliopulos et al., 1999) and was used for generating all mutants. The PAR1 mutants P40N and S42D were generated using the Quick Change Site-Directed Mutagenesis kit (Stratagene) and sequenced to verify the fidelity of the mutagenesis. The effects of these mutations on cleavage rates of a T7-tagged receptor were then measured.

Figures 2C, 2D, 2E, 2F:
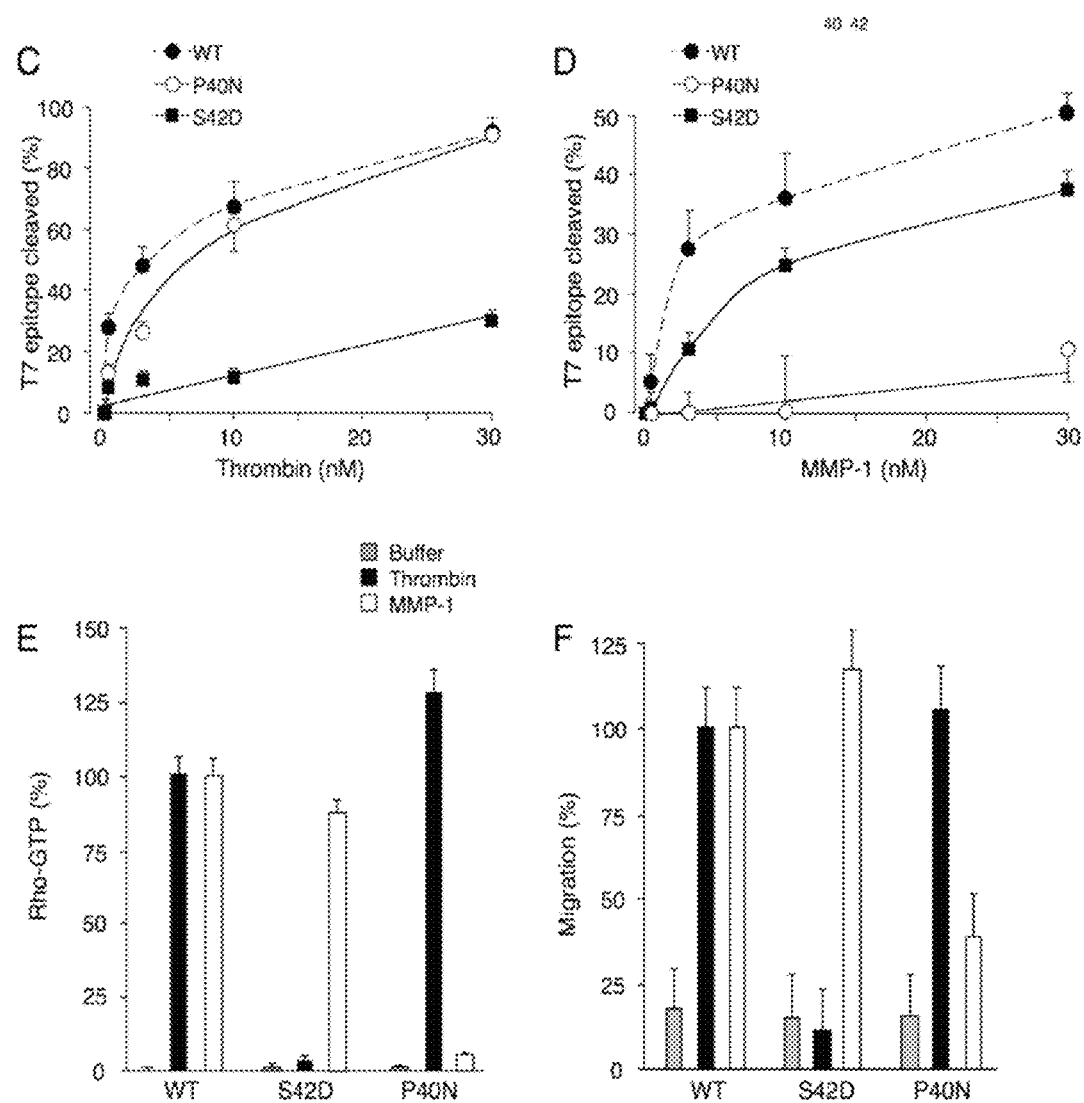
FIG. 2C shows the cleavage of PAR1 N-terminal extracellular mutants by thrombin.
FIG. 2D shows the cleavage of PAR1 N-terminal extracellular mutants by MMP-1.
FIG. 2E shows RhoA signaling by the different PAR-1 mutants in the presence of thrombin or MMP-1
FIG. 2F depicts the chemotactic migration of MCF-7 cells expressing thrombin and MMP1-cleavage site mutants.

In FIG. 2D, COS7 cells transiently transfected with T7-tagged WT, P40N or S42D PAR1, were incubated for 30 min at 37° C. in PBS with 0.3-30 nM Thrombin (FIG. 2C) or APMA-activated MMP-1.

Figures 2G, 2H, 2I, 2J:
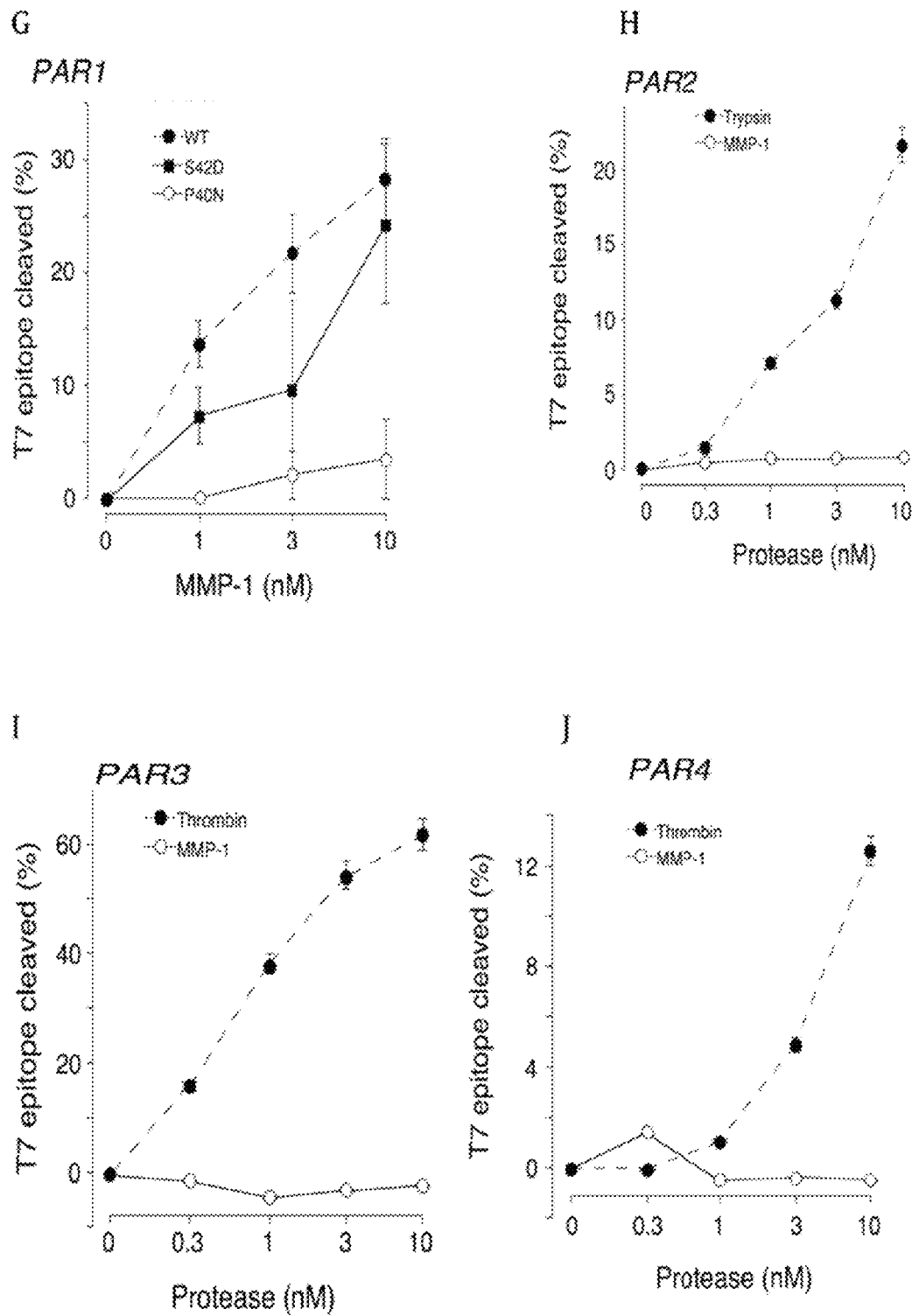
FIG. 2G shows the cleavage of PAR1 N-terminal extracellular domain mutants expressed on COS7 Cells using MMP-1 purified from another source.
FIG. 2H shows the cleavage of wild-type PAR-2 expressed on COS7 Cells by MMP-1 or trypsin.
FIG. 2I shows the cleavage of wild-type PAR-3 expressed on COS7 Cells by MMP-1 or thrombin.
FIG. 2J shows the cleavage of wild-type PAR-4 expressed on COS7 Cells by MMP-1 or thrombin.

In FIG. 2G, COS7 cells transiently transfected with T7-tagged WT, P40N or S42D PAR1 were incubated for 30 min at 37° C. in PBS with 0.3-10 nM APMA-activated MMP-1 (Biomol, Cat No. SE 361).

In FIGS. 2H-2J, COS7 cells transiently transfected with T7-tagged PAR-2, PAR-3 and PAR-4 were incubated for 60 min at 37° C. in PBS with 0.3-10 nM thrombin (for PAR3 or PAR4) or 0.3-10 nM trypsin (for PAR2), or APMA-activated MMP-1. Loss of T7 epitope was analyzed by flow cytometry as described previously (Boire et al., 2005: Kuliopulos et al., 1999).

The results show P40N PAR1 mutant was fully cleaved by thrombin but was poorly cleaved by MMP-1 using two independent sources of MMP-1 (FIG. 2C-D, FIG. 2G). Conversely, the S42D PAR1 mutant was substantially cleaved by MMP-1 but was poorly cleaved by thrombin. Identical results were seen for cleavage of a mutant TR26-P40N peptide, which was cleaved at the $_{R41}$-$_{S42}$ bond by thrombin but was not cleaved by MMP-1 (FIG. 2A). Functional studies validated the relative cleavage specificities of the P40N and S42D mutants for thrombin and MMP-1.

The level of RhoA signaling of the different PAR-1 mutants was then measured in the presence of thrombin or MMP-1 (see FIG. 2E). MCF-7 cells transiently transfected with T7-tagged WT, S42D or P40N PAR1 for 48 h were stimulated with 10 nM thrombin, 10 nM MMP-1 or PBS buffer for 15 min at 37'C. Rho-GTP present in platelet lysates (mean+/−SD, n=3) was precipitated with glutathione S-transferase (GST)-rhotekin-reduced glutathione-agarose beads as described (Kaneider et al., 2007) and Rho-GTP was determined by probing the Western blots with anti-RhoA (26C4 Ab) monoclonal antibody. Platelet lysates were also run on a separate gel and immunoblotted with anti-RhoA to assess total RhoA.

As shown in FIG. 2F, chemotactic migration of MCF-7 cells expressing thrombin and MMP1-cleavage site mutants was also assessed. MCF-7 cells transfected with the PAR1 cleavage mutants were allowed to migrate overnight toward DMEM/0.1% BSA (buffer) plus 3 nM thrombin or 3 nM MMP-1 in a Transwell apparatus (8-μm pore). Cells which migrated toward the bottom side of the membrane were counted and expressed as % relative to WT PAR1 and thrombin.

Thrombin is able to fully activate Rho signaling and chemotactic migration in MCF-7 cells expressing the P40N mutant, but had essentially no activity toward the S42D mutant (FIGS. 2E-F). Conversely, MMP-1 was able to induce Rho signaling and chemotaxis in MCF-7 cells expressing the S42D mutant, but had little activity towards the P40N mutant. By comparison, 0.3-10 nM MMP-1 was not able to detectably cleave T7-tagged PAR2, PAR3, nor PAR4 expressed on COS7 cells (FIGS. 2H-2J). Together, these cleavage and signaling data indicate that MMP-1 specifically activates PAR1 by cleaving at $L_{0.39}\downarrow_{P40}$RSFL rather than at the $LDP_{R41}\downarrow_{S42}FL$ thrombin cleavage site and does not cleave the other PARs.

I-(C) Activation of PAR1 Signaling with the MMP1-Generated Tethered Ligand

MMP-1 cleavage of PAR1 at $LD\downarrow P_{40}RS$ will generate a longer tethered ligand, $P_{40}$RSFLLRN-, than that produced by thrombin. To provide further evidence that MMP1-generated tethered ligand could activate PAR1, the ability of the synthetic peptide, PR-SFLLRN (PR-TRAP) to stimulate PAR1 signaling was tested.

Figures 3A, 3B, 3C:
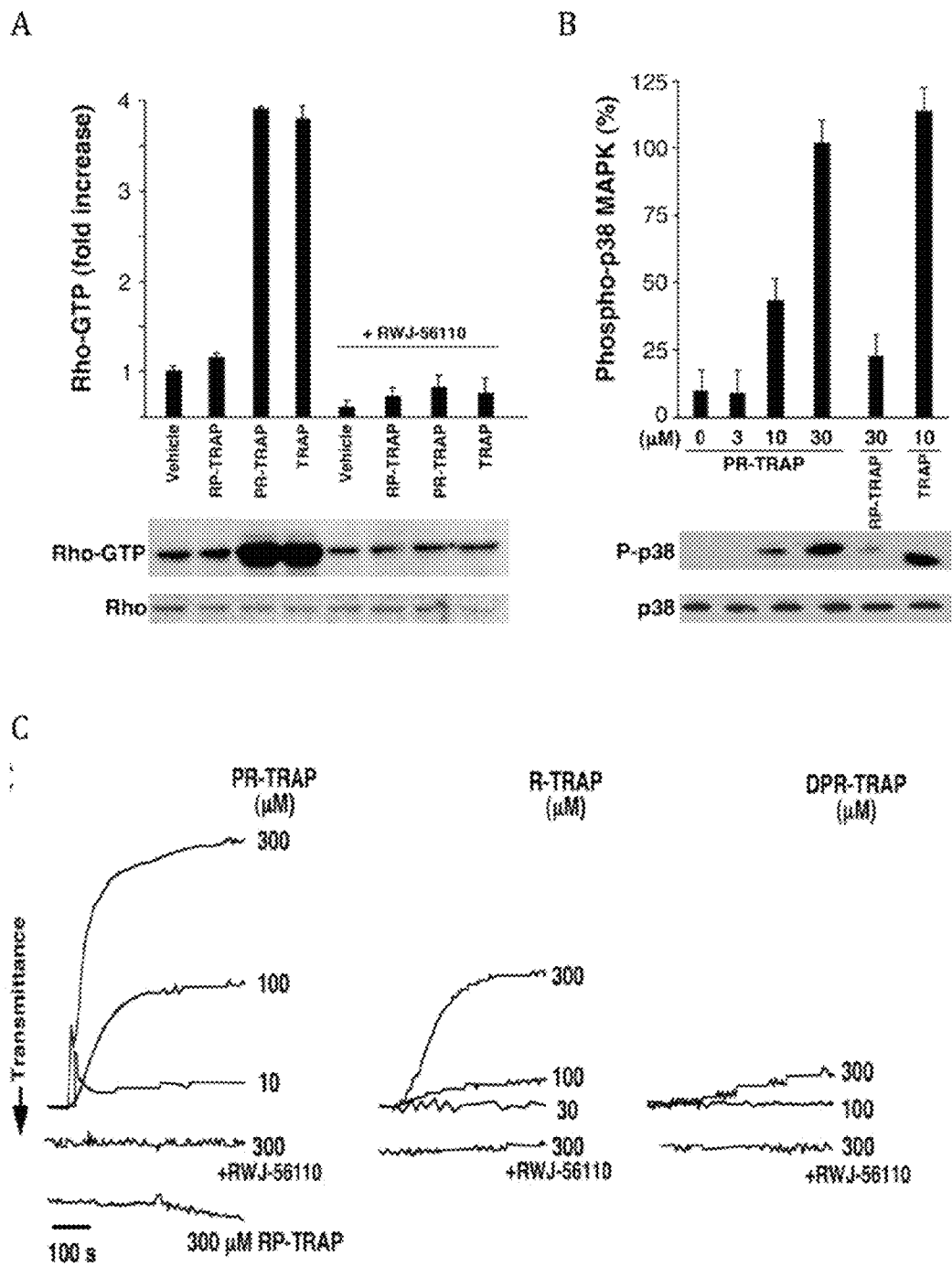
FIG. 3A shows the PRSFLLRN peptide (PR-TRAP) induces PAR1-dependent RhoA activation in platelets.
FIG. 3B shows the PRSFLLRN peptide (PR-TRAP) activates p38 MAPK in platelets.
FIG. 3C shows changes in platelet shape induced by the PRSFLLRN peptide (PR-TRAP).

As shown in FIG. 3A, the effect of the PRSFLLRN peptide (PR-TRAP) on PAR1-dependent RhoA activation in platelets was measured. Gel-filtered human platelets, supplemented with 0.3 mg/mL fibrinogen, were treated with 0.2% DMSO vehicle, or 30 μM SFLLRN (TRAP), PR-TRAP or reversed peptide (RP-TRAP), for 5 min at 37° C. in presence or absence of 1 μM RWJ-56110 as indicated. Platelets were lysed and Rho-GTP and total Rho was determined by Western analysis as described in the Experimental Procedures. Western bands were quantified by densitometry and results expressed relative to fold-increase from basal.

In FIG. 3B, the effect of the PRSFLLRN peptide (PR-TRAP) on p38 MAPK in platelets was measured. Platelets were stimulated with different concentrations of PR-TRAP, RP-TRAP or TRAP as indicated for 5 min at 37° C. Platelets were lysed with Laemmli sample buffer and proteins assessed by Western blot of p38 MAPK activity with phospho-specific p38 MAPK antibody or total p38MAPK antibody.

In FIG. 3C, the ability of the PRSFLLRN peptide (PR-TRAP) to induce a change in platelet shape was determined. Washed human platelets were pretreated with 2 mM EGTA and then treated with the indicated agonists in the presence or absence of 1 μM RWJ-56110 while stirring at 1100 rpm. The decrease in light transmittance is an indication of the platelet shape change reaction.

The results show PR-TRAP is a full agonist of PAR1-dependent Rho and p38 MAPK signaling in platelets (FIG. 3A-B). Addition of the PAR1 antagonist, RWJ-56110, completely blocked signaling induced by PR-TRAP. PR-TRAP ligand also activated changes in platelet shape (see FIG. 3C), a critical early event in platelet activation which is mediated by $G_{12/13}$-Rho signaling (Huang et al., 2007; Offermanns et al., 1994). Again, PR-TRAP-induced platelet shape change was completely blocked by the PAR1 antagonist, RWJ-56110 (FIG. 3C).

Two other peptides were tested for agonist activity which would be generated by putative cleavage at the flanking peptide bonds: the R-TRAP peptide corresponding to cleavage at $LDP_{40}\downarrow R_{41}$SFLLRN and the DPR-TRAP peptide corresponding to cleavage at $L_{38}\downarrow D_{39}$PRSFLLRN (FIG. 2B). The R-TRAP peptide retained partial agonist activity for PAR1-dependent platelet shape change, whereas the DPR-TRAP peptide had nearly no activity (FIG. 3C). Likewise, the control peptide, RP-TRAP, in which the first two amino acid residues were reversed, did not stimulate Rho or p38 MAPK, nor platelet shape change (FIGS. 3A-C).

The ability of exogenously-added MMP-1 to activate PAR1-dependent signaling in platelets was also confirmed.

Figures 4A, 4B, 4C, 4D, 4E, 4F:
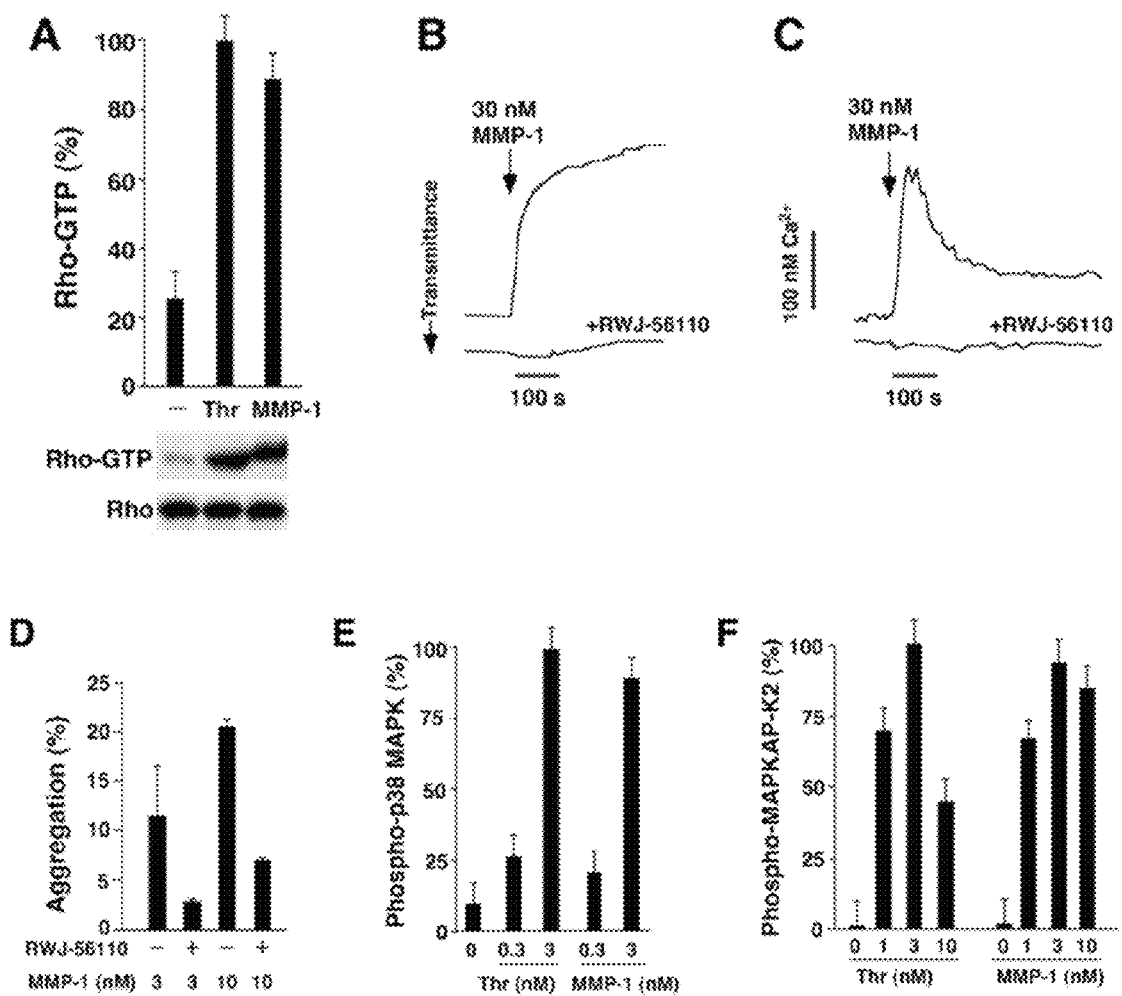
FIG. 4A shows that MMP-1 activates Rho-GTP in platelets.
FIG. 4B shows MMP-1 can induce changes in platelet shape.
FIG. 4C shows MMP-1 induces PAR1-dependent calcium fluxes in platelets.
FIG. 4D shows MMP-1 induces platelet aggregation.
FIG. 4E shows MMP-1 activates p38MAPK in platelets.
FIG. 4F shows MMP-1 activates the downstream MAP-KAP-K2 in platelets.

In FIG. 4A, the effect of MMP-1 on Rho-GTP in platelets was measured. Gel filtered human platelets were exposed to 3 nM thrombin or 3 nM APMA-activated MMP-1 as indicated for 5 min at 37° C. and Rho-GTP and total Rho was determined as described above.

In FIG. 4B, the ability of MMP-1 to induce platelet shape change was determined. Washed human platelets were pre-treated with 2 mM EGTA and then challenged with MMP-1 in the presence or absence of 1 μM RWJ-56110 while stirring at 1100 rpm. Shape change was measured as described above.

In FIG. 4C, the induction of PAR1-dependent calcium fluxes by MMP-1 was measured. Calcium flux measurements of gel filtered platelets following challenge with MMP-1 in the presence or absence of RWJ-56110 were performed at 25° C. with emission recorded at 510 nm and dual excitation at 340 and 380 nm as described (Kuliopulos. 1999).

In FIG. 4D, the induction of platelet aggregation by MMP-1 was determined. Gel-filtered platelets were challenged with MMP-1 in the presence or absence (0.2% DMSO vehicle) of the PAR1 inhibitor 1 μM RWJ-56110.

Finally, in FIGS. 4E-4F, platelet PAR1-dependent MAPK signaling induced by MMP-1 was also measured. Gel filtered platelets were challenged with the indicated concentrations of thrombin (Thr) or MMP-1 for 5 min as in FIG. 4A and p38MAPK (FIG. 4E) or downstream MAPKAP-K2 (FIG. 4F) activation was quantified by densitometry of Western blots using a phospho-p38MAPK or phospho-MAPKAP-K2 antibody, respectively. Blots were re-probed by p38MAPK or MAPKAP-K2 to confirm equal loading in each lane (data not shown).

The results show MMP-1 (3 nM) was able to stimulate Rho-GTP activity to the same extent as equimolar thrombin (FIG. 4A). MMP-1 was also able to elicit platelet shape change, calcium mobilization, and aggregation which was inhibited by the PAR1 antagonist, RWJ-56110 (FIGS. 4B-D). Exogenously added MMP-1 also activated phospho-p38 MAPK and its substrate, MAPKAP-K2, in an activity profile similar to thrombin (FIGS. 4E-F). MAPKAP-K2 phosphorylates the small heat shock protein HSP27 involved in cytoskeletal reorganization (Sundaresan and Farndale, 2002), further suggesting that MMP-1 may play a role in the initial events leading to platelet shape change and help prime platelets for aggregation.

I-(D) Colagen Triggers P38 MAPK Signaung, Rho Activation and Platelet Aggregation Through MMP1-PAR1

The effect of pharmacologic blockage of metalloproteases or PAR1 on collagen-dependent platelet aggregation was then tested (see FIG. 5). Gel-filtered platelets from healthy individuals (supplemented with 0.3 mg/ml fibrinogen) were challenged with 5 μg/ml collagen in the presence or absence (0.2% DMSO vehicle) of the indicated inhibitors and allowed to stir at 900 rpm in an aggregometer cuvette (250 μL) at 37° C. Platelets were pre-incubated for 5 min with the thrombin inhibitors PPACK (200 μM) or hirudin (1 U/ml), the Zn-chelator 1,10-phenanthroline (1,10-PA; 100 μM), the broad spectrum metalloprotease inhibitor MMP-200 (200 nM), the MMP-1 inhibitor FN-439 (3 μM), the PAR1 ligand binding site inhibitor RWJ-56110 (1 μM), the PAR1 blocking antibody (75 μg/ml), the PAR1 pepducin lipopeptides P1pal-12 (3 μM) or P1pal-7 (3 μM), the PAR4 pepducin lipopeptide P4pal-10 (3 μM), MMP-8 inhibitor (25 nM) or MMP9/13 inhibitor (10 nM).

Figures 5A, 5B, 5C, 5D:
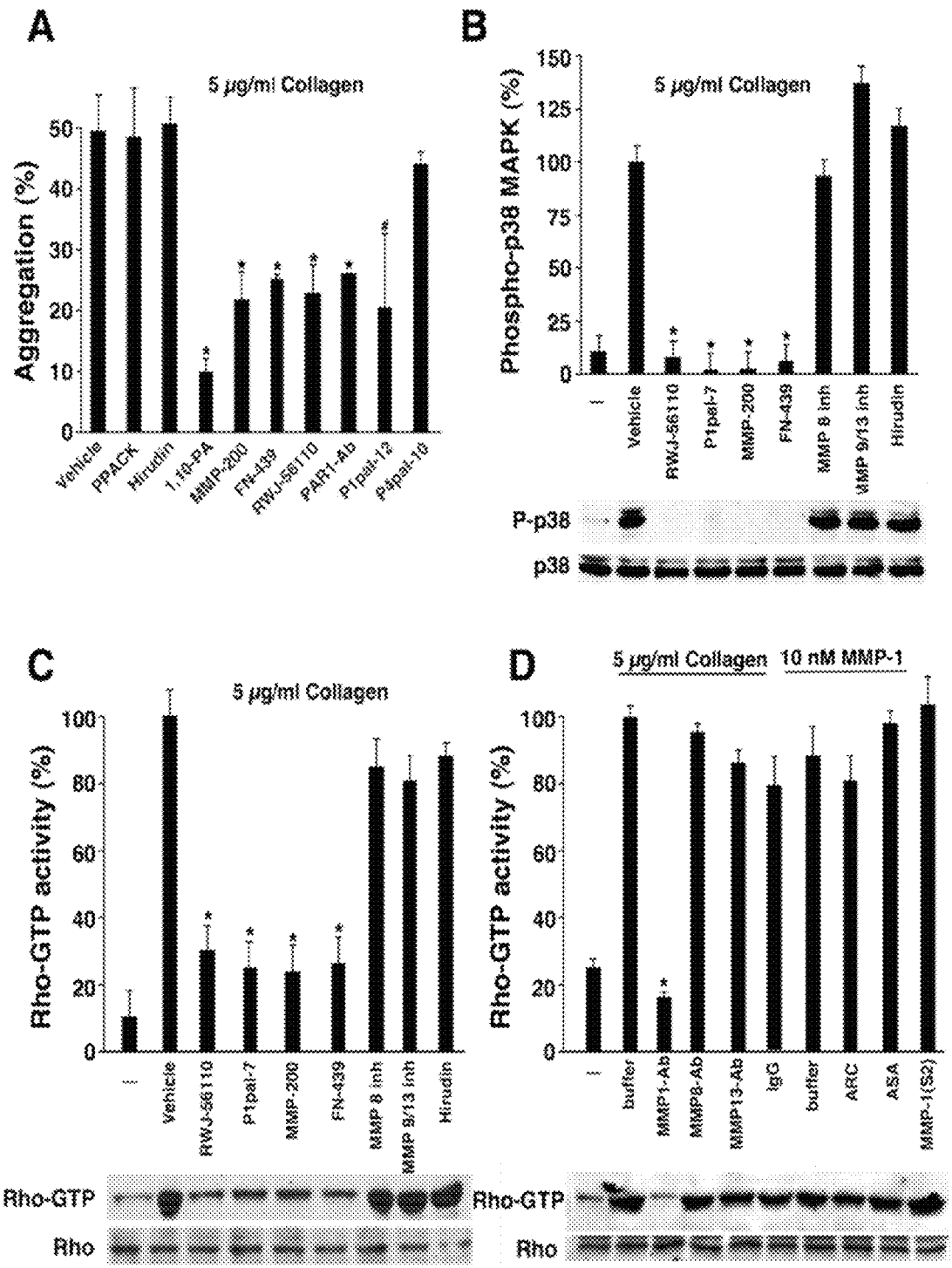
FIG. 5A shows the effect of pharmacologic blockage of metalloproteases or PAR1 on platelet aggregation in the presence of 5 mg/ml collagen.
FIG. 5B shows the effect of pharmacologic blockage of metalloproteases or PAR1 on platelet p38 MAPK activity in the presence of 5 mg/ml collagen.
FIG. 5C shows the effect of pharmacologic blockage of metalloproteases or PAR1 on platelet Rho-GTP activity in the presence of 5 mg/ml collagen.
FIG. 5D shows the effect of various blocking Abs (anti-MMP-1, anti-MMP-8 and anti-MMP-13) and various inhibitors (ARC (P2Y12 antagonist AR-C69931MX), ASA (aspirin)) on platelet Rho-GTP activity in the presence of 5 mg/ml collagen alone or together with MMP-1 (Calbiochem or S2, BioMol).

In FIG. 5A, platelet aggregation was monitored by light transmittance.

In FIG. 5B, platelets were treated as in FIG. 5A and then lysed with Laemmli sample buffer 5 min after addition of collagen, p38 MAPK activity was then assessed by western blot with a p38 MAPK phospho-Ab and total p38 loading was determined using a p38 MAPK antibody.

In FIG. 5C, platelets were treated as in FIG. 5B and then Rho GTP activity was assessed by western blot.

In FIG. 5D, platelets were pre-treated with various blocking Abs for 2 h or inhibitors (ARC, 0.5 μM P2Y12 antagonist AR-C69931MX; ASA, 1 mM aspirin for 30 min) and stimulated with one of 5 μg/ml collagen, 10 nM MMP-1 (Calbiochem), or 10 nM MMP-1 from a second source (S2, BioMol) as indicated and Rho-GTP activity assessed as in FIG. 5C. Representative blots are shown at the bottom of FIGS. 5B-D. Data are the mean±s.d. of three experiments. P*<0.01, #<0.05.

Figure 5E:
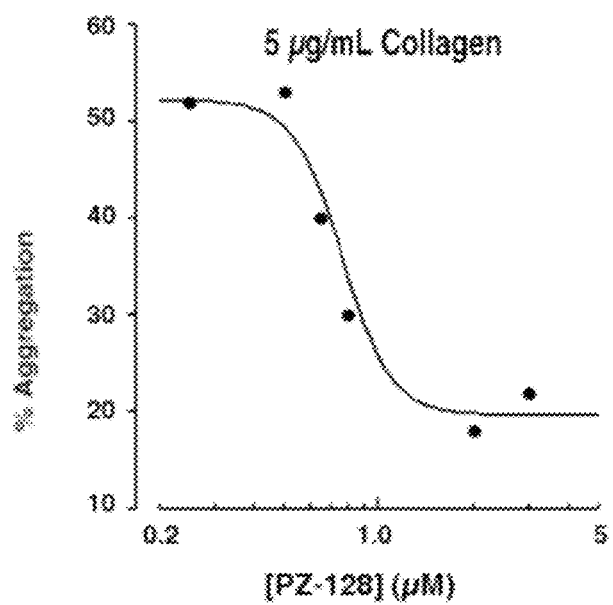
FIG. 5E shows effect of a particular pepducin (P1pal-7 denoted as "PZ-128") on platelet aggregation in the presence of 5 mg/ml collagen.

In FIG. 5E, platelets were pretreated with various concentrations of P1pal-7 (denoted as "PZ-128" in the figure, and also known as P1i3pal-7) in 0.2% DMSO vehicle and activated with SFLLRN, collagen. ADP and ristocetin as indicated. Percent aggregation was defined at the maximal point 7-15 min following addition of agonist.

The results show soluble type I fibrillar collagen stimulates platelet aggregation with an ECso of 5 μg/ml. Inhibition of metalloproteases with the zinc-chelating agent 1,10-phenanthroline, resulted in 80% loss of aggregation to 5 μg/ml collagen (FIG. 5A). Likewise, the broad spectrum metaiioprotease hydroxamate inhibitor, MMP-200 ($IC_{50}$=7 nM for MMP-1, 2.3 nM for MMP-2, 135 nM for MMP-3, 10-100 nM for MMP-7, 1-10 nM for MMP-13) caused a significant 50-60% inhibition of collagen-initiated aggregation. Treatment with the MMP-1 inhibitor. FN-439, inhibited collagen-induced aggregation to the same extent as MMP-200. Conversely, inhibitors against MMP-8, MMP-9 and MMP-13 had no effect on collagen-induced aggregation (data not shown). The specific thrombin inhibitor hirudin or the broad-spectrum serine protease inhibitor, PPACK, had no effect on collagen aggregation (FIG. 5A). PAR1 was inhibited by three orthogonal approaches to evaluate its contribution to collagen-dependent aggregation. The small-molecule inhibitor RWJ-56110 or a PAR1-blocking antibody, attenuated 50% of collagen (5 μg/ml)-induced aggregation, the same extent as the MMP-1 inhibitor. Likewise, the cell-penetrating PAR1 pepducin lipopeptides, P1pal-12 and P1pal-7 (also known as P1i3pal-7), which inhibit PAR1 signaling to intracellular G proteins (Boire et al., 2005; Covic et al., 2002a; Kaneider et al., 2007), gave identical levels of inhibition as blocking MMP-1 (FIGS. 5A and 5E). Inhibition of the PAR4 thrombin receptor with the P4pal-10 pepducin lipopeptide (3 μM) had only a slight (~10%) effect on collagen-induced aggregation (FIG. 5A).

Collagen is known to induce p38 stress-activated protein kinase (MAPK) pathways in human platelets though the mechanism remains unclear (Kuliopulos et al., 2004; Sundaresan and Farndale, 2002). As shown in FIG. 5B, addition of collagen causes robust phosphorylation of p38 MAPK. The collagen (5 μg/ml)-induced phospho-p38 MAPK signal was effectively blocked by the PAR1 and MMP-1 inhibitors, but not with inhibitors against MMP-8, MMP-9/13, or thrombin. Collagen-dependent activation of the p38 MAPK substrate, MAPKAP-K2 is also dependent on both PAR1 and MMP-1. The PAR1 antagonists, RWJ-56110, P1pal-7 and FN-439 but not by MMP8 inhibitor blocked collagen-activation of phospho-MAPKAP-K2 (data not shown).

The ability of collagen to stimulate Rho-GTP activity through the MMP1-PAR1 pathway was also tested. Collagen caused robust activation of Rho-GTP, which was attenuated by 75% with antagonists against PAR1 and MMP-1, but not by inhibitors or blocking antibodies against MMP-8, MMP-9/13, or thrombin (FIGS. 5C-D).

However, at saturating levels of collagen (20 µg/ml) sufficient to elicit full aggregation of platelets, none of the PAR1 nor MMP-1 inhibitors had a major effect (525%) on collagen-dependent aggregation, the phospho-p38 MAPK signal, or Rho-GTP activity (data not shown), indicating that the MMP1-PAR1 pathway can be bypassed at super-EC5 levels of collagen.

To address whether the observed MMP-1 effects were due to secondary secretion of ADP or thromboxane after collagen stimulation, the P2Y12 ADP and thromboxane pathways were inhibited with ARC and aspirin (ASA) respectively (FIG. 5D). Treatment of platelets with either ARC or aspirin had no effect on the ability of 5 or 20 µg/ml collagen or 10 nM MMP-1 to activate Rho-GTP (FIGS. 5D, 5E and 5H) or phospho-p38 MAPK, but the inhibitors could still suppress aggregation to collagen (FIGS. 5E, 5G and 5H). In contrast, blockade of the MMP1-PAR1 pathway nearly completely inhibited activation of p38 and Rho-GTP to 5 µg/ml collagen (FIGS. 5B-D). This would indicate that at EC50 collagen exposure, MMP1-PAR1 is essential for activation of p38 and Rho-GTP, and important for aggregation, whereas the secondary ADP and thromboxane pathways do not activate p38 and Rho-GTP at any range of collagen concentration. At saturating collagen, the ADP and thromboxane contributions appear to compensate for the MMP1-PAR1 pathway in platelet aggregation via mechanisms that do not involve p38 or Rho-GTP signaling.

I-(E) Early Platelet Thrombus Formation on Collagen Surfaces is Promoted By MMP-1 and PAR1

Activation of platelets in ruptured atherosclerotic plaques occurs under high shear-stress conditions on subendothelial surfaces enriched in collagen fibrils. The role of MMP-1 and PAR-1 in the initial formation and propagation of platelet-platelet thrombi on collagen surfaces was investigated by specifically inhibiting MMP-1 or PAR1 (see FIGS. 6A-6B).

Whole human blood was anti-coagulated with heparin (10 U/mL), or with corn trypsin inhibitor (CTI, 30 µg/ml final) before being pretreated for 10 min with vehicle (0.2% DMSO), MMP-200 (200 nM), MMP-1 inhibitor FN-439 (3 µM), PAR1 ligand binding site inhibitor RWJ-56110 (1 µM), PAR1 pepducin lipopeptides P1pal-12 or P1pal-7 (3 µM), or for 30 min with 1 mM aspirin prior to the assay as indicated. Following incubation with inhibitors, the blood was perfused over a glass slide coated with fibrillar collagen type I.

A flow chamber (Glycotech) with Type-I fibrillar collagen-coated glass slides was mounted on the stage of an IMT-2 inverted microscope (Olympus) equipped with Retiga 1300 digital camera (QImaging) and 40× objective. One of the flow chamber inlets was connected to a syringe pump (Harvard Apparatus) calibrated to create a shear rate of $1,000^{s-1}$. The whole blood pretreated with the various pharmacologic inhibitors was then perfused over the collagen-coated glass slide. After 2-15 min of perfusion, blood was removed from the flow chamber by gentle displacement with PIPES buffer and images of 8-10 fields were acquired using OpenLab software (Improvision). Acquired images were further analyzed using NIH Image 1.63 software. Images were first sharpened and the edges of separate platelets and platelet aggregates were determined. Following the adjustment of threshold, images were converted into the binary format, and the particle analysis function was activated to highlight the regions covered by platelets with the sensitivity set to one single adherent thrombocyte. For the conversion of pixels into square micrometers, a calibration curve was built using 2.5, 6, 20, 25, and 45 µm polystyrene beads (Polyscience) using acquisition conditions identical to the experimental. The mean area of formed thrombus was determined at 7 min. Area measurements in FIG. 6B represent the mean±s.e. of three separate experiments from five different blood donors.

Treatment with either MMP-1 or PAR1 inhibitors did not affect the primary adhesion of platelets to the immobilized collagen fibrils. However, the growth rate and size of platelet aggregate "strings" was significantly attenuated by ~75% with the MMP-1 inhibitor, FN-439, or the PAR1 blocking agents P1pal-12, P1pal-7 or RWJ-56110 (FIGS. 6A-B). By comparison, aspirin pre-treatment had little or no effect on the growth of the platelet thrombi. This result is consistent with thromboxane playing a relatively minor role in thrombogenesis under arterial shear stress conditions (Jackson et al., 2003) as compared to the MMP1-PAR1 pathway.

Collagen-activated platelets also provide a pro-coagulant surface and produce tissue factor, which aids in the production of thrombin (Giesen at al., 1999; Mackman, 2004; Schwertz et al., 2006). To evaluate whether MMP1-PAR1 activation of early platelet thrombi formation is also relevant under conditions in which thrombin activity is not inhibited, arterial flow experiments were performed in the presence of corn trypsin inhibitor (CTI) which blocks factor XIIa and the contact pathway of coagulation but does not inhibit thrombin generation in whole blood (Mann et al., 2007; Rand et al., 1996).

Figures 6A, 6B, 6C, 6D, 6E, 6F:
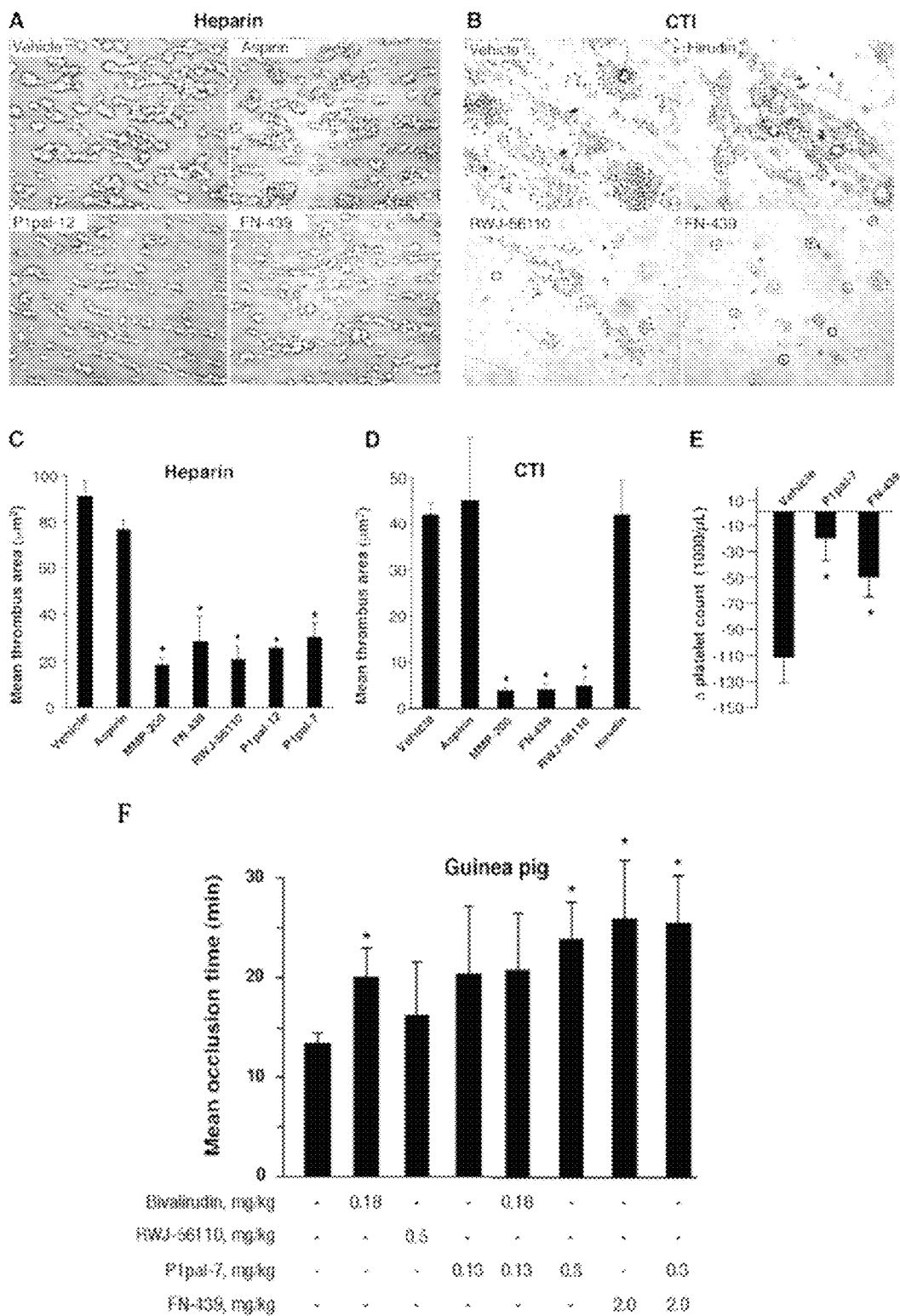
FIGS. 6A-6B show that inhibition of MMP-1 or PAR1 prevents early micro-thrombus formation on collagen surfaces in the presence of heparin.
FIGS. 6C-6D show that inhibition of MMP-1 or PAR1 prevents early platelet micro-thrombus formation on collagen surfaces independently of thrombin.
FIG. 6E shows that P1pal-7 and FN-439 protects against collagen-induced systemic platelet activation in guinea pigs.
FIGS. 6F and 6G show that inhibition of PAR1 and/or MMP-1 prevents occlusion of carotid arteries in guinea pigs.

Whole blood was anti-coagulated with CTI (30 µg/mL) to block the contact pathway, otherwise the experiments were conducted identically as in FIG. 6A. Hirudin was used as indicated at 0.0013 UImL.

The results using the CTI anti-coagulant were very similar to those conducted with heparin. As shown in FIGS. 6C and 6D, inhibition of MMP-1 or PAR-1 significantly attenuated the size of the platelet micro-thrombi on the collagen surfaces, whereas addition of the thrombin inhibitor, hirudin, had no effect. Likewise, aspirin pre-treatment of the whole blood did not affect the extent of platelet-thrombi formation on the collagen surfaces. Thus, under conditions of arterial shear stress, MMP1-PAR1 significantly promotes early thrombogenesis on collagen surfaces.

Clot retraction assays were then performed to examine the potential role of MMP-1 on the structure of large platelet-rich clots over time. Platelet receptors trigger clot retraction by activating myosin-dependent contraction of the cytoskeleton, which is in turn connected to the extracellular matrix (fibrinogen) via focal adhesions (see FIG. 6I).

Platelet rich plasma (PRP) was isolated from human whole blood anti-coagulated with 4% sodium citrate. Clot retraction assays were done in 1 ml volumes containing 800 µl PBS and 200 µl PRP plus 10 µl red blood cells to enhance contrast. Samples were pretreated with FN-439 (5 µM), MMP9/13 Inh (10 nM) or RWJ-56110 (1 µM) for 15 min and clot formation was initiated with 1-20 µg/ml type I fibrillar collagen. Samples were incubated at 37° C. for 90 or 240 min and then photographed with a digital camera. Each photograph in FIG. 6I is representative of three independent experiments.

Figure 6G:
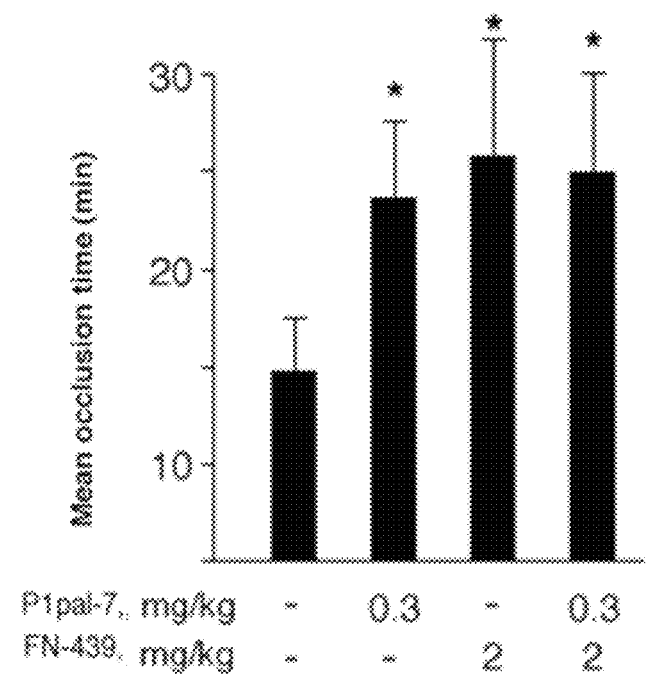
Figure 6H:
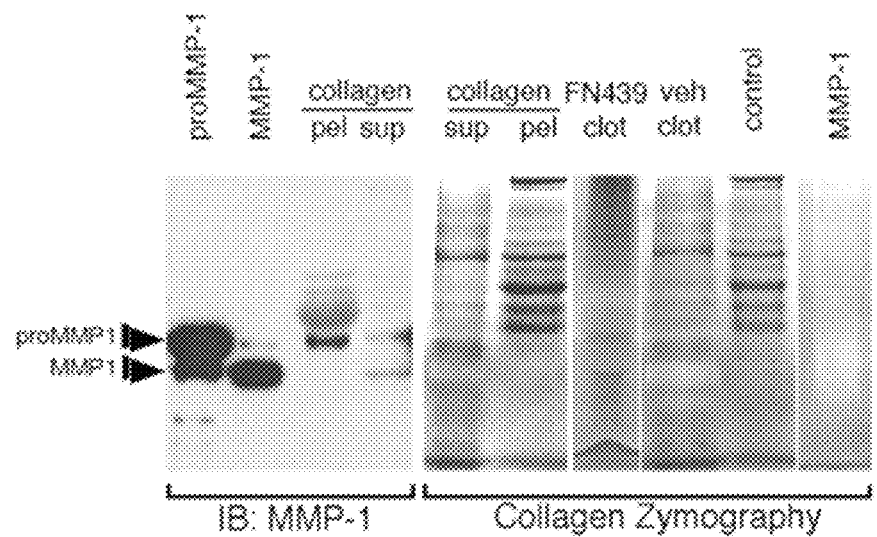
FIG. 6H shows the detection of MMP-1 activity in guinea pig platelet supernatant and arterial dot induced by collagen.
Figure 6I:
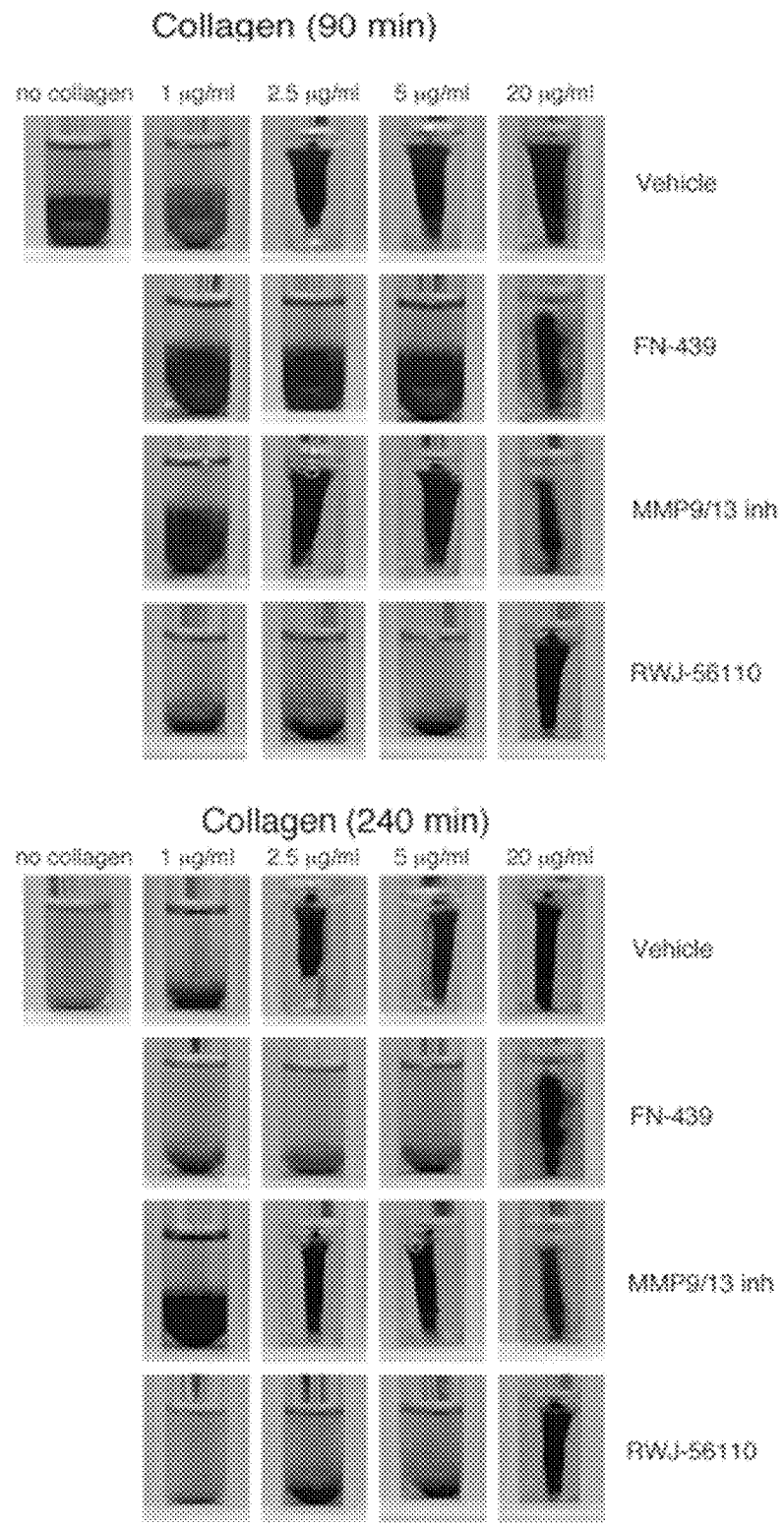
FIG. 6I are photographic depiction of dot retraction assays with various agents added to platelet-rich human plasma. The top block were photographs taken after 90 minutes of incubation and the bottom block after 240 minutes.

As shown in FIG. 6I, the MMP-1 inhibitor, FN-439, completely inhibited clot formation and retraction induced by 2.5-5 µg/ml collagen. Blockade of PAR1 with RWJ-56110 gave a nearly identical pattern of inhibition, whereas the negative control MMP9113 inhibitor had negligible effects over the whole collagen titration. Therefore, MMP-1 and PAR1 play a significant role in the formation and retraction of large platelet-rich thrombi initiated by collagen.

I-(F) Pharmacologic Inhibition of Matrix Metalloprotease-2 (MMP-2) Attenuates Collagen-Dependent Platelet Aggregation to a Similar Extent as Blockade of MMP-1.

To further demonstrate that inhibition of MMP-1 abrogates collagen-induced platelet activation, a series of experiments were performed to test the ability of platelets to aggregate in the presence of the MMP-2 inhibitors, which are known to inhibit pro-MMP-1 cleavage and activation.

Figures 8A, 8B, 8C, 8D:
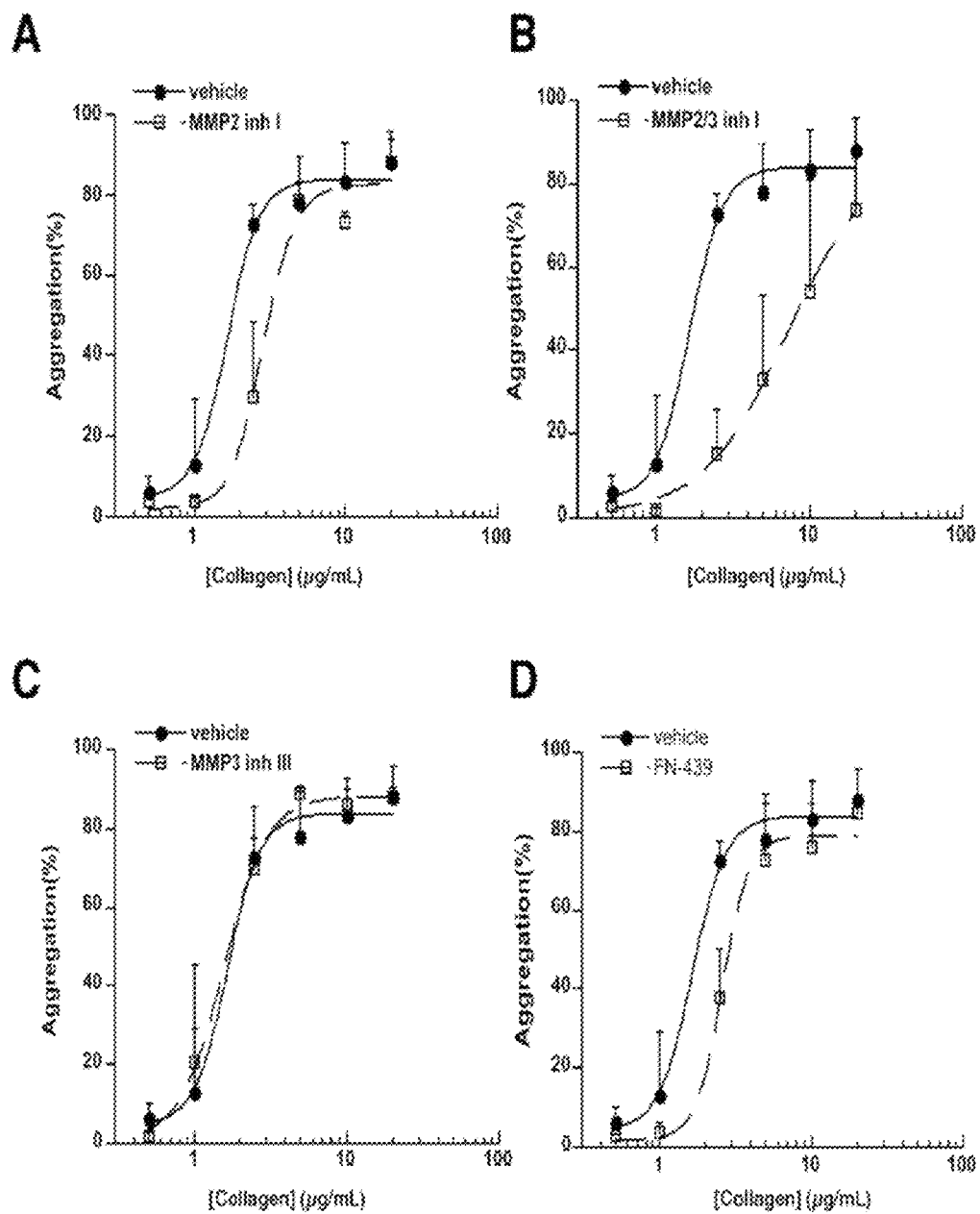

Human platelets were isolated by gel filtration chromatography of platelet-rich plasma with the use of a Sepharose 2B column in modified PIPES buffer. After addition of 2.0 mM $CaCl_2$ and 300 µg/ml fibrinogen, the platelets were pre-incubated for 2 minutes with vehicle (0.2% DMSO), 5 µmol/L MMP2 inhibitor I (FIG. 8A), 51 µmol/L MMP2/3 inhibitor I (FIG. 88), 15 µmol/L MMP3 inhibitor III (FIG. 8C), 5 µmol/L FN-439 (FIG. 8D), 200 nM MMP-200 and then stimulated by various concentrations of collagen. Aggregation was measured for 15 minutes with the use of a Chronolog 560VS/490-2D aggregometer. The aggregation assay was repeated with 3-6 healthy blood donors.

In FIG. 8E, platelets were pre-incubated for 5 min with the thrombin inhibitor hirudin (1 U/ml), the metalloprotease inhibitors 1,10-phenanthroline (1,10-P; 100 µM) or MMP-200 (200 nM), the MMP-1 inhibitor FN-439 (3 µM), the PAR1 ligand binding site inhibitor RWJ-56110 (1 µM), the PAR1 blocking antibody (75 µg/ml), the PAR1 pepducin lipopeptides P1pal-12 (3 µM) or P1pal-7 (3 mM), or the PAR4 pepducin lipopeptide P4pal-10 (3 µM). Data are the mean±s.d. of three experiments. P*<0.01, #<0.05.

Inhibition of MMP-2, but not MMP-3, inhibits collagen-induced platelet aggregation.

I-(G) Systemic Platelet Activation and Arterial Thrombosis by MMP-1 and PAR1 in Guinea Pig A series of experiments were then performed to determine if blocking the MMP1-PAR1 pathway would protect against collagen-mediated systemic platelet activation in vivo. Guinea pigs serve as an relevant model to test platelet function because like humans they also express PAR1 on their platelets (Leger et al., 2006a) and guinea pig MMP-1 shares 90% identity with human MMP-1 (Huebner et al., 1998).

Animal experiments were performed in accordance with the National Institutes of Health guidelines and approved by the Tufts Medical Center Institutional Animal Care and Use Committee. 2-4 week old Hartley guinea pigs (170-260 g) were anesthetized by an i.p. injection of xylazine (10 mg/kg) plus ketamine (50 mg/kg) and then catheterized via the left jugular vein and injected (200 µL) with either vehicle (20% DMSO/80% water), P1pal-7 or FN-439. For determination of collagen-dependent systemic platelet activation, 10 min after administration of inhibitors, 200 µg collagen in 200 µL of PBS was delivered via the jugular vein. Ten min after collagen injection, blood was collected into sodium citrate (1% v/v final) from the contralateral jugular vein and platelet counts were measured with a Hemavet850. The enzymatic activity of active MMP-1 in supernatants and platelet lysates was determined using DQ collagen I as fluorogenic substrate in the presence or absence of 3 µM FN-439, or 20 µg/ml of control IgG or a MMP-1 blocking Ab (preincubated for 2 h at 37° C.), as indicated.

Figures 7A, 7B, 7C, 7D:
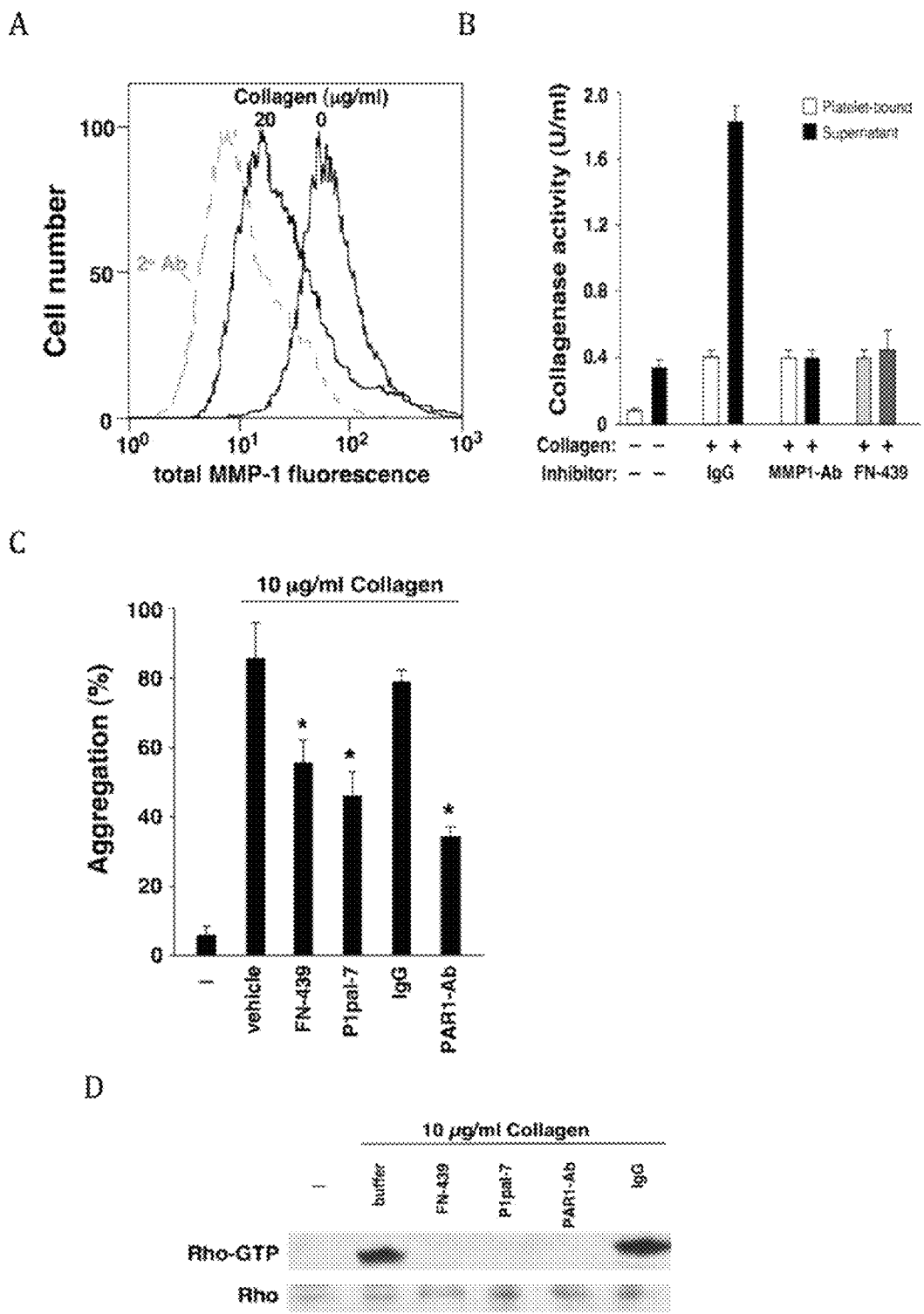
FIG. 7A shows the surface expression of MMP-1 on guinea pig platelets as determined by flow cytometry.
FIG. 7B shows the enzymatic activity of active MMP-1 in guinea pig platelet lysates and supernatants in the presence or absence of FN-439, control IgG or a MMP-1 blocking antibody.
FIG. 7C shows the effect of pharmacologic blockage of metalloproteases or PAR1 on guinea pig platelet aggregation in the presence of 10 mg/ml collagen.
FIG. 7D shows Rho GTP activity in the platelets used in FIG. 7C.

FIG. 7A shows the surface expression of MMP-1 on guinea pig platelets as determined by flow cytometry. Dashed grey line: secondary antibody alone; Solid lines: FACS profiles of platelets treated with the indicated concentrations of collagen for 15 min at 37° C. and then stained with primary MMP-1 (AB806) plus secondary antibodies. FIG. 7B shows the activation of guinea pig platelets treated for 15 min with 20 µg/ml type-I collagen in the presence of various inhibitors As described above.

As shown in FIGS. 7A and 7B, FACS analysis on guinea pig platelets showed proMMP-1 is expressed on their surface and addition of collagen causes release of collagenase activity which is completely blocked by either FN-439 or a MMP1-neutralizing Ab. Likewise, inhibition of MMP-1 or PAR1 gave 35-50% suppression of aggregation and complete inhibition of Rho-GTP activity in response to 10 µg/ml collagen in guinea pig platelets (FIGS. 7C-D), which was consistent with the previous results using human platelets.

Intravascular platelet activation was then induced by an intravenous injection of collagen into the guinea pigs. Vehicle, P1pal-7 (3 mg/kg) or FN-439 (10 mg/kg) were delivered i.v. to the internal jugular vein of guinea pigs (n=6) and allowed to circulate for 10 min. Blood was drawn before and 10 min after collagen (200 µg) induction of systemic activation of platelets. The infused collagen caused a severe drop in mean systemic platelet counts from a baseline level of 309,000±50,000/mL to 194,000±20,000/mL. Strikingly, pre-administration of the PAR1 pepducin lipopeptide, P1pal-7, almost completely protected against collagen-induced thrombocytopenia in the guinea pigs (FIG. 6E). The MMP-1 inhibitor, FN-439, also afforded significant protection against intravascular platelet activation.

To assess the efficacy on arterial thrombosis by blockade of thrombin, MMP-1, or PAR1, a standard carotid artery $FeCl_3$ injury model was used in guinea pigs. $FeCl_3$ causes denudation of the artery and exposure of type I collagen and other subendothelial matrix proteins. The effects of blocking thrombin with bivalirudin, MMP-1 with FN-439, and PAR1 with either the small molecule antagonist RWJ-56110 or the P1pal-7 pepducin on arterial thrombosis were then compared using a dopier probe.

For these arterial thrombosis experiments, 10 min after i.v. administration of vehicle (–), bivalirudin, RWJ-56110, P1 pal-7 or FN-439 (n=4-5) through the jugular vein at the indicated concentrations, the right carotid arteries were injured for 20 min using a 24 $mm^2$ piece of Bio-Rad Trans-Blot paper soaked in 20% $FeCl_3$. Arterial flow 5 mm distal to the site of injury was measured with a 0.5 V Doppler probe (Transonic Systems). An arterial occlusion was defined as a flow rate of <0.01 V for ≥5 min. Doppler measurements were terminated at the 30 min time point following injury (* designates p<0.05).

Bivalirudin alone (0.18 mg/kg) prolonged the mean arterial occlusion time from 13 min to 20 min (FIG. 6F). The small molecule PAR1 antagonist, 0.5 mg/kg RWJ-56110, did not appreciably affect the mean occlusion time, however, equimolar amounts of P1pal-7 (0.13 mg/kg, 75% lipopeptide, 25% salt) gave a similar trend of protection as bivalirudin (p=0.10) (FIG. 6F). Supplementation of 0.13 mg/kg P1pal-7 with 0.18 mglkg bivalirudin gave no additional prolongation of the arterial occlusion time, but a slightly higher dose of P1pal-7 alone (0.3 mg/kg), gave a significant (p<0.05) 80% prolongation of the mean occlusion time (FIG. 6F). Further, the ammonium acetate salt of P1pal-7 in 100% water gives similar IC50 values and retains specificity for PAR1. Administration of the MMP-1 antagonist FN-439 alone (at 2.0 mg/kg), gave a similar prolongation (90%, FIG. 6F) of the mean arterial occlusion time. Co-administration of the PAR1 and MMP-1 inhibitors did not lead to further prolongation of the mean occlusion time, consistent with MMP-1 acting in the same pathway as PAR1. Similar results were also reported in FIG. 6G. These examples provide the validation for one of the present inventive principles that inhibition of MMP1-PAR1 can be used to provide substantial protection against collagen-dependent platelet activation and acute arterial thrombosis independently of blocking thrombin.

MMP-1 activity with the dots was determined by collagent zymography (see FIG. 6H). Platelets were isolated from guinea pigs and stimulated with 20 µg/ml collagen for 15 min and platelet supernatants and pellets, or whole resting platelets (control), prepared as described Above. Samples were resolved on a 8% type I collagen/acrylamide zymography gel and collagenase zymogram was developed as described by (Gogly et al., 1998) or immunoblotted with MMP1-Ab, AB806. Arterial dots were also removed from the Fe—Cl irnjured carotid arteries from animals (n=5) treated with FN-439 (FN439 clot) or vehicle (veh dot) as in 6F and 6G and dots were dissolved in lysis buffer and passed 5× through a 21-gauge needle. The lysates were centrifuged and supernatents resolved on the zymography gel. The two lanes on the left side of the western blot have 20 ng of proMMP-1 or 20 ng APMA-activated MMP-1, and the right hand lane in the zymogram has 0.5 µg of APMA-activated human MMP-1.

Collagen zymography revealed that the platelet-rich dot isolated from injured carotid arteries of vehicle-treated animals (veh clot) had significant MMP-1 activity, which co-migrated with APMA-activated MMP-1 and with the MMP-1 activity from the supernatants of collagen-activated platelets (FIG. 6H). Conversely, resting platelets (control) from whole blood or arterial thrombi from animals treated with the MMP1-inhibitor (FN439 dot) did not contain active MMP-1. These data, together with the previous results, indicate that inhibition of MMP1-PAR1 may provide substantial protection against collagen-dependent platelet activation and acute arterial thrombosis in animals.

Materials

Sodium citrate, EDTA, apyrase, 1,10-phenanthroline, A-23187, and U-46619 were obtained from Sigma. ADP and fibrillar Type I collagen were from Chronolog Corp. MMP-200 was obtained from Enzyme Systems Products.

ProMMP-1 (≥290% purity, from human synovial fibroblasts), proMMP-3, proMMP-7, FN-439 (MMP inh-1), MMP8 inh, MMP9/13 inh, hirudin, and PMA were from Calbiochem. RWJ-56110 was a kind gift from Claudia Derian and Particia Andrade-Gordon of Johnson & Johnson Pharmaceuticals Research and Development. AR-C69931MX was a gift from Astra Zeneca.

The pepducin lipopeptides, P1pal-12. P4pal-10 and P1pal-7 were synthesized with C-terminal amides and purified by RP-HPLC as before (Covic et al., 2002a).

SFLLRN (SEQ ID NO:23), TFLLRN (SEQ ID NO:26), PRSFLLRN (SEQ ID NO:1), RPSFLLRN (SEQ ID NO:21), PSFLLRN (SEQ ID NO:27), DPRSFLLRN (SEQ ID NO:24), PAR1 N-terminal thrombin cleavage peptide (A26-R41) (SEQ ID NO:28), PAR1 flexible linker peptide (N-acetyl-$T_{67}$-$L_{84}$-C)(SEQ ID NO:29), and TR26 ($A_{36}$-$E_{60}$-S) (SEQ ID NO:15) and TR26-P40N ($A_{36}$-$K_{61}$) (SEQ ID NO:18) were synthesized with C-terminal amides by the Tufts Peptide Core Facility and purified to ≥95% purity by RP-HPLC.

The IIaR-A monoclonal antibody, which reacts to the amino-terminal thrombin-cleavage peptide of PAR1, was from Biodesign (Kennebunk, Me.).

The PAR1 blocking antibody raised against residues $S_{42}$FLLRNPNDKYEPF$_{55}$C (SEQ ID NO:30), was generated from rabbits as previously described (Kuliopulos 1999). A solid phase proMMP-1 ELISA system from R&D Systems (Quantikine DMP100) utilizes 2 monoclonal antibodies that recognize the pro domain of MMP-1.

The ELISA assay detects proMMP-1 and soluble pro domain but does not detect active MMP-1. The MMP-1 blocking Ab (rabbit polyclonal antibody AB8105) raised against the conserved C-terminus recognizes both pro and active forms of MMP-1 but do not cross react with other MMP family members was from Chemicon, the MMP-8 (IM38L) and MMP-13 (IM44L) blocking Abs were from Oncogene, the anti-$\alpha_2$ (Gi9 or AK7), $\beta_1$ (MAB1987), $\beta_3$ (MAB1957) were from Chemicon, GPVI (SC20149) was from Santa Cruz, GPIBα (MM2/174) was from AbD Serotec and ELISA kits for Abs against the MMP-1 pro-domain (DMP100, R&D Systems) of MMP-1 were used according to the manufacturer's instructions.

Anti-phospho p38MAPK, p38MAPK, anti-phospho-MAPKAP-K2, and anti-MAPKAP-K2 were from Cell Signaling, anti-RhoA (done 26C4) was from Santa Cruz Biotechnology.

Corn trypsin inhibitor and thrombin were from Haematologic Technologies, the Quick Change Mutagenesis kit was from Stratagene.

II Inhibitors of the MMP-1-PAR-1 Signalling Pathway

II-(A) MMP1-PAR1 as a New Target for the Prevention of a Thrombotic Disease State Matrix metalloproteases are implicated in the chronic pro-inflammatory and tissue-remodeling events leading to cleavage of interstitial collagen and development of vulnerable atherosclerotic plaques (Sukhova et al., 1999). Although patho-anatomic studies of human atherosclerotic lesions suggest that large plaques can cause ischemic symptoms, the key contributing factor to the morbidity and mortality associated with atherosclerosis is excessive platelet thrombus formation on exposed collagen surfaces following acute plaque rupture (Glass and Witztum, 2001; Rugged, 2002).

This invention discloses a novel collagen-initiated pathway of thrombogenesis which is mediated by the autocrine action of platelet MMP-1 on the PAR1 receptor. Exposure of platelets to collagen caused robust activation of MMP-1 on the platelet surface, which in turn directly cleaved and activated PAR1 independently of thrombin. These studies provide a link between matrix-dependent activation of metalloproteases and platelet G protein signaling and identify MMP1-PAR1 as a potential new target for the prevention of arterial thrombosis.

Unexpectedly, MMP-1 cleaved PAR1 at a distinct site in its extracellular domain, which generated a longer tethered ligand than that produced by thrombin. The MMP1-cleaved receptor or soluble peptide analog strongly stimulated $G_{12/13}$-Rho-dependent pathways, chemotaxis and MAPK signaling in platelets and other cells. The MMP-1 cleavage site on PAR1 aligned with an optimized MMP-1 cleavage site motif determined from mixture-based oriented peptide libraries (Turk et al., 2001) and by substrate cleavage studies (Berman et al., 1992; Netzel-Amett at al., 1991). Mutation of respective P1' residues uncoupled MMP-1 from thrombin cleavage and generated PAR1 receptors that exhibited protease-specific activity.

Collagen signaling in human platelets through the $\alpha_2\beta_1$ and GPVI/FcγR collagen receptors is not well understood, but is dependent on G protein signaling through autocrine stimulation of ADP and thromboxane receptors (Jackson et al., 2003). Blockade of the P2Y12 $G_i$-coupled ADP receptor inhibits collagen-dependent thrombogenesis under arterial flow conditions, thus establishing an important role for downstream ADP-$G_i$ signaling. Thromboxane activates the $G_q$ and $G_{12/13}$-coupled $TXA_2$ receptor, however, aspirin fails to prevent thrombogenesis on collagen surfaces under arterial shear stress and does not prevent occlusive thrombus formation in patients with severe arterial stenosis (Veen et al., 1993). The current studies show that MMP-1 is a potent activator of PAR1-$G_{12/13}$ pathways involved in platelet shape change and Rho activation and thus would synergize with P2Y12-$G_i$ signaling.

Blockade of MMP-1 or PAR1 with pharmacologic inhibitors significantly attenuated thrombogenesis on collagen surfaces under arterial shear stress conditions and thrombosis in animals. As compared to MMP-1 inhibition, antagonism of thrombin had little effect on early thrombogenesis on the collagen surfaces under high arterial flow rates. Thrombin may be more important for later propagation and stability of platelet thrombi, and is not involved in initiating early thrombus growth at high arterial shear stress (Fressinaud et al., 1992; Gast et al., 1994; Inauen et al., 1990) unless tissue factor levels are extremely high (Okorie et al., 2008). Likewise, thrombin inhibitors such as heparin have incomplete effects on platelet thrombus formation at high arterial flow rates, but have a more prominent inhibitory effect on the growth and overall stability of platelet thrombi at low and intermediate shear rates (Inauen et al., 1990).

Unlike direct blockade of MMP-1 or thrombin, downstream inhibition of PAR1 may hold the potential to prevent both the initial MMP1-dependent events of platelet thrombi propagation on blood vessel collagen, along with later thrombin-dependent propagation and stabilization and could prove beneficial in preventing arterial thrombosis in acute settings. To that end, the present invention provides that various agents. e.g., the cell-penetrating PAR1 pepducin, can provide efficient blockade of both thrombin-mediated and collagen-MMP1-mediated activation of PAR1 which could benefit large patient populations being treated for atherothrombotic heart disease and ischemic stroke.

II-(B) Screening for Novel MMP1-PAR1 Inhibitors

Discovery of agents acting on the MMP-1/PAR-1 signaling pathway may be accomplished using methods that are well known in the art. In a first step, agents that bind to a target molecule within the MMP-1-PAR-1 signaling pathway are identified. The efficacy of a selected agent may then be evaluated using in vitro PAR-1 signaling or cleavage assays, as described herein, and then in vivo using animal models of thrombotic disease states. MMP-1/PAR-1 specific agents may act as an agonist or antagonist of the MMP-1-PAR-1 signaling pathway.

In a preferred embodiment, an agent acts as a direct or indirect antagonist of the MMP-1-PAR-1 signaling pathway. Direct antagonists are compounds that bind directly to their target molecule, such as MMP-1 or PAR-1, and inhibit the biological activity of that target molecule.

For example, a MMP-1 antagonist may be a compound that binds to and inhibits MMP-1 enzymatic activity, i.e. proteolytic cleavage between aspartic acid at position 39 (D39) and proline at position 40 (P40) of the protease-activated receptor-1 (PAR-1). In one embodiment, the MMP-1 antagonist may bind directly to the MMP-1 active site to inhibit MMP-1 enzymatic activity. In another embodiment, the MMP-1 antagonist may bind to a site other than the active site and inhibit MMP-1 activity by inducing a conformational change in MMP-1 or modifying the post-translational state of the protein, such as phosphorylation, de-phosphorylation, glycosylation, acylation, alkylation, or lipoylation.

In other examples, a PAR-1 antagonist may be a compound that binds to PAR-1 and prevents proteolytic cleavage between aspartic acid at position 39 (D39) and proline at position 40 (P40) of the protease-activated receptor-1(PAR-1). In one embodiment, a PAR-1 antagonist may be a compound, such as an antibody, that binds directly over the $LD_{39} \downarrow P_{40} RSFL$ (SEQ ID NO:31) MMP-1cleavage site at the N terminal domain of PAR-1 and prevents proteolytic cleavage at that site. In other embodiments, a PAR-1 antagonist may inhibit proteolytic cleavage of PAR-1 by inducing a conformational change in PAR-1 or altering the post-translational modification of PAR-1, such as phosphorylation, de-phosphorylation, glycosylation, acylation, alkylation, or lipoylation in such a way that proteolytic cleavage at the $LD_{39} \downarrow P_{40} RSFL$ (SEQ ID NO:31) MMP-1cleavage site is prevented.

In still other embodiments, a PAR-1 antagonist may interfere with the MMP-1-generated tethered ligand's ability to interact with other domains within PAR-1 and thereby inhibit activation of MMP-1 mediated PAR-1 signaling. In still other embodiments, a PAR-1 antagonist may prevent PAR-1 signaling by interfering with the assembly of protein complexes comprising PAR-1 or MMP-1 or the dimerization of PAR-1 with other PAR family members.

In one embodiment, the agent is a PAR-1 pepduan lipopeptide. In another embodiment, the agent is SCH 530348, a PAR-1 antagonist developed by Schering-Plough, or derivative thereof.

In another embodiment, a inhibitor may interfere with complex formation between PAR-1 and various nucleotides including, but not limited to GTP, GDP or GMP.

In yet another embodiment, a MMP-1 or PAR-1 agent may modulate the gene expression of other factors that are required for MMP-1 mediated PAR-1 activation. In this aspect, an "agent" may include modulators of the gene transcription or translation of factors required for MMP-1 mediated PAR-1 activation.

Indirect antagonists are compounds that bind to ancillary target molecules that are required for MMP-1 mediated activation of PAR-1 signaling activity. For example, a MMP-1 antagonist may inhibit MMP-1 activity by inhibiting the proteolytic cleavage of pro-MMP-1 to active MMP-1. For example, a MMP-1 antagonist may bind to the pro-MMP-1's proteolytic cleavage site and prevent cleavage.

In other embodiments, a PAR-1 antagonist may inhibit PAR-1 signaling activity by preventing the formation of protein complexes between MMP-1 and associated factors or between PAR-1 and associated factors. In still other embodiments, a PAR-1 antagonist may interfere with the biological activity of downstream PAR-1 effector molecules that are required for MMP-1 mediated PAR-1 signaling activity.

Direct inhibitors may be identified by screening for compounds using in vitro screening assays that require a purified target molecule whose activity is required for MMP-1 mediated PAR-1 signaling. In a preferred embodiment, the target protein is native PAR-1 protein or a PAR-1 deletion mutant in which the N terminal residues 1 and 39 are deleted. However, the experimental approach disclosed herein may be applied to any target protein that is required for PAR-1 function. For example, the target molecule may be MMP-1 or factors required for MMP-1 activation. In yet other examples, the target molecule may be a factor, such as a kinase or phosphatase, that modulates PAR-1 activity by altering the post-translational modification of PAR-1 or MMP-1.

II-(C) Prokaryotic Expression of Recombinant PAR-1 Polypeptide

In one embodiment, the invention requires purification of a target protein or a fragment thereof, e.g. PAR-1.

PAR-1 may be purified directly from a biological source, such as human platelets. Alternatively, DNA encoding PAR-1, or fragment thereof, may be operably linked to genetic constructs, e.g., vectors and plasmids for expression in a prokaryotic host. In some cases a nucleic acid is operably linked to a transcription and/or translation sequence in an expression vector to enable expression of a PAR-1 polypeptide. By "operably linked," it is meant that a selected nucleic acid, e.g., a coding sequence, is positioned such that it has an effect on, e.g., is located adjacent to, one or more sequence elements, e.g., a promoter andfor ribosome binding site (Shine-Dalgarno sequence), which directs transcription and/ or translation of the sequence. Some sequence elements can be controlled such that transcription and/or translation of the selected nucleic acid can be selectively induced. Exemplary sequence elements include inducible promoters such as tac, T7, P(BAD) (araBAD), and beta-D-glucuronidase (uidA) promoter-based vectors. Control of inducible promoters in *E. coli* can be enhanced by operably linking the promoter to a repressor element such as the lac operon repressor (lac(R)). In the specific case of a repressor element, "operably linked" means that a selected promoter sequence is positioned near enough to the repressor element that the repressor inhibits transcription from the promoter (under repressive conditions). Typically, expression plasmids and vectors include a selectable marker (e.g., antibiotic resistance gene such as Tet(R) or Amp(R)). Selectable markers are useful for selecting host cell transformants that contain a vector or plasmid. Selectable markers can also be used to maintain (e.g., at a high copy number) a vector or plasmid in a host cell. Alternatively, the recombinant expression vector can be transcribed and translated in vitro, for example using T7 promoter regulatory sequences and T7 polymerase.

In some embodiments, the polypeptide sequence of interest may be expressed as part of a fusion protein using recombinant DNA technology. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa or enterokinase. Typical fusion expression vectors include pGEX (Pharmacia Biotech Inc; Smith, D. B. and Johnson, K. S. (1988) Gene 67: 31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

The PAR-1 polypeptide may also be engineered to have an affinity tag fused to its N or C terminal end. For example, the target protein may be fused to a short tag peptides, such as the Hexa-His peptide or the HA Epitope Tag (Influenza Hemaglutinin) synthetic peptide YPYDVPDYA. These tag proteins or peptides also facilitate subsequent protein purification by affinity chromatography.

Other commonly used bacterial host plasmids include pUC series of plasmids and commercially available vectors, e.g., pAT153, pBR, PBLUESCRIPT, pBS, pGEM, pCAT, pEX, pT7, pMSG, pXT, pEMBL. Another exemplary plasmid is pREV2.1. Plasmids that include a nucleic acid described herein can be transfected or transformed into bacterial host cells for expression of PAR-1 polypeptides. Techniques for transformation are known in the art, including calcium chloride or electroporation. In other embodiments, the recombinant DNA sequence is cloned into a bacteriophage vector. In certain embodiments, transformed host cells include non-pathogenic prokaryotes capable of highly expressing recombinant proteins. Exemplary prokaryotic host cells include laboratory and/or industrial strains of *E. coli* cells, such as BL21 or K12-derived strains (e.g., C600, DHlalpha, DHSalpha, HBIOI, INVI, JM109, TBI, TGI, and X-IBlue). Such strains are available from the ATCC or from commercial vendors such as BD Biosciences Clontech (Palo Alto. CA) and Stratagene (La Jolla, Calif.). For detailed descriptions of nucleic acid manipulation techniques, see Ausubel et al., eds., Current Protocols in Molecular Biology, Wiley Interscience, 2006, and Sambrook and Russell, Molecular Cloning: A Laboratory Manual, Cold Spring Harbor Press, NY, 2001.

II-(D) Eukaryotic Expression of Recombinant Par-1 Polypeptide

In other embodiments, PAR-1 protein or fragments thereof may be expressed in eukaryotic cells. Using standard recombinant DNA techniques, a PAR-1 nucleic add is cloned into a vector in a form suitable for expression of the nucleic acid in a host cell. Preferably the recombinant expression vector includes one or more regulatory sequences operatively linked to the nucleic acid sequence that facilitates expression within the eukaryotic cell. The term "regulatory sequence" includes promoters, enhancers and other expression control elements (e.g., polyadenylation signals). Regulatory sequences include those, which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., PAR-1 proteins, mutant forms of PAR-1 proteins, fusion proteins, and the like). For example, PAR-1 polypeptides can be expressed in insect cells (e.g., using baculovirus expression vectors), yeast cells or mammalian cells. Suitable host cells are discussed further in Goeddel, (1990) Gene Expression Technology: Methods in Enzymology 185, Academic Press, San Diego, Calif.

In mammalian cells, the expression vector's control functions can be provided by viral regulatory elements. For example, commonly used promoters are derived from polyoma, Adenovirus 2, cytomegalovirus and Simian Virus 40. In some embodiments, the promoter may be an inducible promoter, e.g., a promoter regulated by a steroid hormone, by a polypeptide hormone (e.g., by means of a signal transduction pathway), or by a heterologous polypeptide (e.g., the tetracycline-inducible systems, "Tet-On" and "Tet-Off"; see, e.g., Clontech Inc., CA, Gossen and Bujard (1992) Proc. Natl. Acad. Sci. USA 89: 5547, and Paillard (1989) Human Gene Therapy 9: 983). In some embodiments, the PAR-1 polypeptide sequence comprises a signal peptide sequence which promotes the secretion of the PAR-1 polypeptide.

Mammalian cell lines suitable for protein expression include, but is not limited to, Chinese hamster ovary cells (CHO) or COS cells (African green monkey kidney cells CV-1 origin SV40 cells; Gluzman (1981) Cell 123: 175-182)). Other suitable host cells are known to those skilled in the art.

Vector DNA can be introduced into host cells via conventional transfection techniques. As used herein, the terms "transformation" and "transfection" are intended to refer to a variety of art-recognized techniques for introducing foreign nucleic acid (e.g., DNA) into a host cell, including calcium phosphate co-precipitation, DEAE-dextran-mediated transfection, lipofection, or electroporation.

II-(E) Screening Assays—Identification of PAR-1/MMP-1 Ligand-Binding Molecules

The invention provides methods (also referred to herein as "screening assays") for identifying modulators, i.e., candidate or test compounds or agents (e.g., proteins, peptides, peptidomimetics, peptoids, small molecules or other drugs), which bind to PAR-1 or MMP-1 proteins, have an inhibitory effect on, for example, PAR-1 or MMP-1 expression or PAR-1 or MMP-1 activity. Compounds thus identified can be used to modulate the activity of target gene products (e.g., PAR-1 or MMP-1 genes) in a therapeutic protocol, to elaborate the biological function of the target gene product, or to identify compounds that disrupt normal target gene interactions.

In one embodiment, the invention provides assays for screening candidate or test compounds that bind to or modulate an activity of a PAR-1 or MMP-1 protein or polypeptide or a biologically active portion thereof.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see. e.g., Zuckermann. R. N. et al. (1994) J. Med. Chem. 37: 2678-85); spatially addressable parallel solid phase or solution phase libraries; synthetic library methods requiring deconvolution; the "one-bead one-compound" library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) Anticancer Drug Des. 12: 145).

In one embodiment, the test compounds may be peptidominetic compounds of the PR-TRAP peptide, PRSFLLNRN or variant thereof.

In other embodiments, a test compound refers to a "recombinant antibody" that is generated using recombinant DNA technology, such as, for example, an antibody expressed by a bacteriophage. The term should also be construed to mean an antibody which has been generated by the synthesis of a DNA molecule encoding the antibody or parts thereof and which DNA molecule expresses an antibody protein or parts thereof, or an amino acid sequence specifying the antibody, wherein the DNA or amino acid sequence has been obtained using synthetic DNA or amino acid sequence technology which is available and well known in the art. Recombinant antibodies may be selected for increased or improved affinity via the screening of a combinatory antibody library under stringent binding conditions. For example, nucleic acids encoding a chimeric or humanized chain can be expressed to produce a contiguous protein. See, e.g., Cabilly et al., U.S. Pat. No. 4,816,567; Cabilly et al., European Patent No. 0 125 023 B1; Boss et al., U.S. Pat. No. 4,816,397; Boss et al., European Patent No. 0 120 694 B1; Neuberger et al., International Publication No. WO86/01533: Neuberger et al., European Patent No. 0 194 276 B1; issued to Winter et al., U.S. Pat. No. 5,225,539; issued to Winter et al., European Patent No. 0 239 400 B1; Queen et al., European Patent No. 0 451 216 B1; and Padlan et al., EP 0 519 596 A1. See also. Newman et al., BioTechnology, 10: 1455-1460 (1992), regarding primatized antibody, and Ladner et al., U.S. Pat. No. 4,946,778 and Bird et al., Science, 242:423-426 (1988)) regarding single chain antibodies. The contents of these patent documents and references are hereby incorporated herein in their entirety.

In other embodiments, test compounds refer to aptamers. Aptamers typically comprise DNA, RNA, PNA, nucleotide analogs, modified nucleotides or mixtures of any of the above. Aptamers may be naturally occurring or made by synthetic or recombinant means. Aptamer sequences are typically discovered by SELEX (Systematic Evolution of Ligands by EXponential Enrichment). This method provides for the in vitro selection of nucleic acid molecules that are able to bind with high specificity to target molecules and is further described in U.S. Pat. No. 5,475,096 entitled "Nucleic Acid Ligands," U.S. Pat. No. 5,270,163 (see also WO 91/19813) entitled "Nucleic Acid Ugands," and more recently "Method for generating aptamers with improved off-rates," U.S. Patent Application no. 2009/0004667, each of which is specifically incorporated by reference herein. Nucleic acid aptamers may also be selected by screening libraries of structurally defined RNA or DNA motifs, as described in "Methods for identifying ligands that target nucleic acid molecules and nucleic acid structural motifs," U.S. Patent Application No. 2008/0188377, the contents of which are hereby incorporated herein in their entirety.

A test compound may be a nucleic acid molecule such as a short oligonucleotide, that is capable of mediating sequence specific RNAi (RNA interference), for example short (or small) interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), translational silencing and others.

Examples of methods for the synthesis of molecular libraries can be found in the art, for example in: DeWitt at al. (1993) Proc. Nat. Acad. Sci. U.S.A. 90: 6909; Erb et al. (1994) Proc. Natl. Acad. Sci. USA 91: 11422; Zuckermann et al. (1994). J. Med. Chem. 37: 2678; Cho at al. (1993) Science 261: 1303; Carrell et al. (1994) Angew. Chem. Int. Ed. Engl. 33: 2059; Carell et al. (1994) Angew. Chem. Int. Ed. Engl. 33: 2061; and Gallop et al. (1994) J. Med. Chem. 37: 1233.

Libraries of compounds may be presented in solution (e.g., Houghten (1992) Biotechniques 13: 412-421), or on beads (Lam (1991) Nature 354: 82-84), chips (Fodor (1993) Nature 364: 555-556), bacteria (Ladner, U.S. Pat. No. 5,223,409), spores (Ladner U.S. Pat. No. 5,223,409), plasmids (Cull et al. (1992) Proc Natl Acad Sci USA 89: 1865-1869) or on phage (Scott and Smith (1990) Science 249: 386-390; Devlin (1990) Science 249: 404-406; Cwirla at al. (1990) Proc. Natl. Acad. Sci. 87: 6378-6382; Felici (1991) J. Mol. Biol. 222: 301-310; Ladner supra.).

In one embodiment, an assay is a cell-based assay in which a cell which expresses a PAR-1 and/or MMP-1 protein or biologically active portion thereof is contacted with a test compound, and the ability of the test compound to modulate PAR-1 and/or MMP-1 activity is determined. Determining the ability of the test compound to modulate PAR-1 activity can be accomplished by monitoring, for example, Rho or MAPK signaling activity as described above. In other embodiments, MMP-1 activity may be monitored by determining the level of cleavage at the $LD_{39}\downarrow P_{40}RSFL$ (SEQ ID NO:31) MMP-1 cleavage site. The cell, for example, can be of mammalian origin, e.g., human. In a preferred embodiment, the cell is a human platelet. In vivo binding of the test compound to PAR-1 or MMP-1 can also be evaluated. This can be accomplished, for example, by coupling the compound with a radioisotope or enzymatic label such that binding of the compound to PAR-1 and/or MMP-1 can be determined by detecting the labeled compound in a complex. Alternatively, PAR-1 or MMP-1 could be coupled with a radioisotope or enzymatic label to monitor the ability of a test compound to modulate MMP-1 cleavage of PAR-1. For example, compounds can be labeled with 1251, 35S, 14C, or 3H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a test compound to interact with PAR-1 or MMP-1 with or without the labeling of any of the interactants can be evaluated. For example, a microphysiometer can be used to detect the interaction of a compound with PAR-1 or MMP-1 without the labeling of either the compound or the PAR-1 or MMP-1. McConnell, H. M. et al. (1992) Science 257: 1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and PAR-1 or MMP-1.

In yet another embodiment, a cell-free assay is provided in which a PAR-1 or MMP-1 protein or biologically active portion thereof is contacted with a test compound and the ability of the test compound to bind to the PAR-1 or MMP-1 protein or biologically active portion thereof is evaluated. Preferred biologically active portions of the PAR-1 or MMP-1 proteins to be used in assays of the present invention include fragments which participate in interactions between PAR-1 or MMP-1 molecules.

Cell-free assays involve preparing a reaction mixture of the target gene protein and the test compound under conditions and for a time sufficient to allow the two components to interact and bind, thus forming a complex that can be removed and/or detected. The interaction between two molecules can also be detected, e.g., using fluorescence energy transfer (FRET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FRET binding event can be conveniently measured through standard fluorometric detection means well known in the art (e.g., using a fluorimeter).

In another embodiment, determining the ability of PAR-1 or MMP-1 protein to bind to a test compound can be accomplished using real-time Biomolecular Interaction Analysis (BIA) (see, e.g., Sjolander, S, and Urbaniczky, C. (1991) Anal. Chem. 63: 2338-2345 and Szabo et al. (1995) Curr. Opin. Struct. Biol. 5: 699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test compound is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either PAR-1 or MMP-1, an PAR-1 or MMP-1 antibody or its target compound to facilitate separation of complexed from uncomplexed forms of one or both of the proteins, as well as to accommodate automation of the assay. Binding of a test compound to a PAR-1 or MMP-1 protein, or interaction of a PAR-1 or MMP-1 protein with a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/PAR-1 or MMP-1 fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or PAR-1 or MMP-1 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of PAR-1 or MMP-1 binding or activity determined using standard techniques.

Other techniques for immobilizing either a PAR-1 or MMP-1 protein or test compounds can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with PAR-1 or MMP-1 protein but which do not interfere with binding of the PAR-1 or MMP-1 protein to its test compound. Such antibodies can be derivatized to the wells of the plate, and unbound target or PAR-1 or MMP-1 protein trapped in the wells by antibody conjugation. Methods for detecting such complexes, in addition to those described above for the GST-immobilized complexes, include immunodetection of complexes using antibodies reactive with the PAR-1 or MMP-1 protein, as well as enzyme-linked assays which rely on detecting an enzymatic activity associated with the PAR-1 or MMP-1 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., (1993) Trends Biochem Sci 18: 284-7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. (1999) Current Protocols in Molecular Biology, J. Wiley: New York). Such resins and chromatographic techniques are known to one skilled in the art (see, e.g., Heegaard, N. H., (1998) J Mol Recognit 11: 141-8; Hage, D. S., and Tweed, S. A. (1997) J Chromatogr B Biomed Sci Appl. 699: 499-525). Further, fluorescence energy transfer may also be conveniently utilized, as described herein, to detect binding without further purification of the complex from solution.

In a preferred embodiment, the assay includes contacting the PAR-1 protein or biologically active portion thereof with MMP-1 to form an assay mixture, contacting the assay mixture with a test compound, and determining the ability of the test compound preferentially bind to PAR-1 or biologically active portion thereof, or to modulate the activity of a PAR-1.

The target gene products of the invention can interact in vivo with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the PAR-1 or MMP-1 genes herein identified. In an alternative embodiment, the invention provides methods for determining the ability of the test compound to modulate the activity of a PAR-1 or MMP-1 protein through modulation of the activity of an upstream effector of a PAR-1 or MMP-1 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

In yet another aspect, the PAR-1 or MMP-1 proteins can be used as "bait proteins" in a two-hybrid assay or three-hybrid assay (see, e.g., U.S. Pat. No. 5,283,317; Zervos et al. (1993) Cell 72: 223-232; Madura et al. (1993) J. Bid. Chem. 268: 12046-12054; Bartel et al. (1993) Biotechniques. 14: 920-924; Iwabuchi et al. (1993) Oncogene 8: 1693-1696; and Brent WO94/10300), to identify other proteins or peptides, which bind to or interact with PAR-1 or MMP-1 and interfere with PAR-1/MMP-1 function.

The two-hybrid system is based on the modular nature of most transcription factors, which consist of separable DNA-binding and activation domains. Briefly, the assay utilizes two different DNA constructs. In one construct, the gene that codes for a PAR-1 or MMP-1 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: PAR-1 or MMP-1 protein can be the fused to the activator domain.) If the "bait" and the "prey" proteins are able to interact, in vivo, forming a PAR-1-dependent complex, the DNA-binding and activation domains of the transcription factor are brought into close proximity. This proximity allows transcription of a reporter gene (e.g., lacZ), which is operably linked to a transcriptional regulatory site responsive to the transcription factor. Expression of the reporter gene can be detected and cell colonies containing the functional transcription factor can be isolated and used to obtain the cloned gene, which encodes the protein/peptide which interacts with the PAR-1 protein.

In another embodiment, modulators of PAR-1 expression are identified. For example, a cell or cell free mixture is contacted with a candidate compound and the expression of PAR-1 mRNA or protein evaluated relative to the level of expression of PAR-1 mRNA or protein in the absence of the candidate compound. When expression of PAR-1 or MMP-1 mRNA or protein is less (statistically significantly less) in the presence of the candidate compound than in its absence, the candidate compound is identified as an inhibitor of PAR-1/MMP-1 mRNA or protein expression. The level of PAR-1/MMP-1 mRNA or protein expression can be determined by methods known in the art. In one embodiment, a test compound may be RNAi or microRNAs that inhibits PAR-1 or MMP-1 gene expression.

In yet another embodiment, the assays described herein may be used to identify the binding site of the MMP-1 generated tethered ligand (see FIG. 9A). Cell-based or cell-free assays could be devised to test if PR-TRAP peptide interacts with one or more extracellular loops of PAR-1. The identity of the target polypeptide sequence could then be verified by site directed mutagenesis of the target sequence using well-established methods known in the art. Libraries of agents can then be screened compounds that specifically disrupt the interact of the tethered ligand with this target sequence by using in vivo binding assays such two hybrid assays in the presence of test compounds. Alternatively, candidate compounds may be screened for their ability to abrogate platelet PAR-1 signaling in the presence of activated MMP-1 or the PR-TRAP peptide ligand as described above. For example, candidate test compounds can be screened for their ability to inhibit Rho-GTP or phospho-p38 MAPK signaling activity in human platelets as described in detail above. In other embodiments, the ability of candidate test compounds to inhibit platelet aggregation may also be assayed as described above. A reporter molecule such as GFP or the like that is responsive to PAR-1 signaling activity would facilitate screening for relevant compounds.

In another aspect, the invention pertains to a combination of two or more of the assays described herein. For example, a modulating agent can be identified using a cell-based or a cell free assay, and the ability of the agent to modulate the activity of a PAR-1 protein can be confirmed in vivo, e.g., in an animal model for a thrombotic disease state. In addition to the guinea pig thrombosis model described above, the efficacy of test compounds on thrombosis in vivo can be assessed using a wide variety of known animal models of thrombosis, for example, as described in U.S. Patent Application Nos. 200510025705 and 2005/0120392, the contents of which are hereby incorporated by reference herein in their entirety.

This invention further pertains to novel agents identified by the above-described screening assays. Accordingly, it is within the scope of this invention to further use an agent identified as described herein (e.g., a PAR-1 or MMP-1 modulating agent, an antisense PAR-1 or MMP-1 nucleic acid molecule, a PAR-1-specific or MMP-1-specific antibody, or a PAR-1 or MMP-1-binding partner) in an appropriate animal model to determine the efficacy, toxicity, side effects, or mechanism of action, of treatment with such an agent. Furthermore, novel agents identified by the above-described screening assays can be used for treatments as described herein.

II-(F) Effects of Blockade of MMP1-PAR1 in the Development of Atherosclerotic Lesions and Neovascularization of the Vaso Vasorum Apolipoprotein E (Apoe) Deficient Mice The role of MMP-1 and PAR1 in the development of atherosclerotic lesions can be studied in an animal model of atherosclerosis, such as apolipoprotein E (apoE) deficient mice.

Twenty five (25) 86.129P2-Apoe$^{fm1Unc}$/J mice, 7 weeks old, were separated into 3 groups and fed ad libitum with high-fat/high-cholesterol diet (21% fat, 0.21% cholesterol) (0120798, Research Diets) for 15 weeks. Group I included 8 mice (n=8) was used as a control group and received Vehicle (20% DMSO in 1×PBS). Group II included 8 mice (n=8) that were treated with MMP Inhibitor I FN-439 (Calbiochem) at a dose of 5 mg/kg. Lastly, group III included 9 mice (n=9) treated with 10 mg/kg of the P1pal-7 pepducin lipopeptide. MMP Inhibitor I (FN-439) is an inhibitor of MMP-1 and MMP-8 ($IC_{50}$=1 µM) and can also inhibit MMP-9 and MMP-3, though at much higher concentrations (IC50=30 µM and 150 µM, respectively). P1pal-7 is a cell-penetrating pepducin lipopeptide based on the third intracellular loop (i3) of human PAR1 and acts as an antagonist of PAR1 signaling. All mice were injected subcutaneously with 100 µl of the corresponding treatment for 6 days a week. At the end of the treatment, and after a 4 hours fasting, the mice were anesthetized with ketamine/xylazine and pressure-fixed with 10% formalin. The heart and the aorta of each mouse were isolated, removed and fixed for 2 days in 10% formalin and adventitial fat was removed. The abdominal area of the aorta was cut and used for whole mount immunohistochemistry. The "aortic arch/thoracic" area and the rest of the "abdominal/iliac" area of the aorta were cut open and pinned on dissecting black wax and used for "en face" staining with Oil-Red-O.

Figures 10A, 10B:
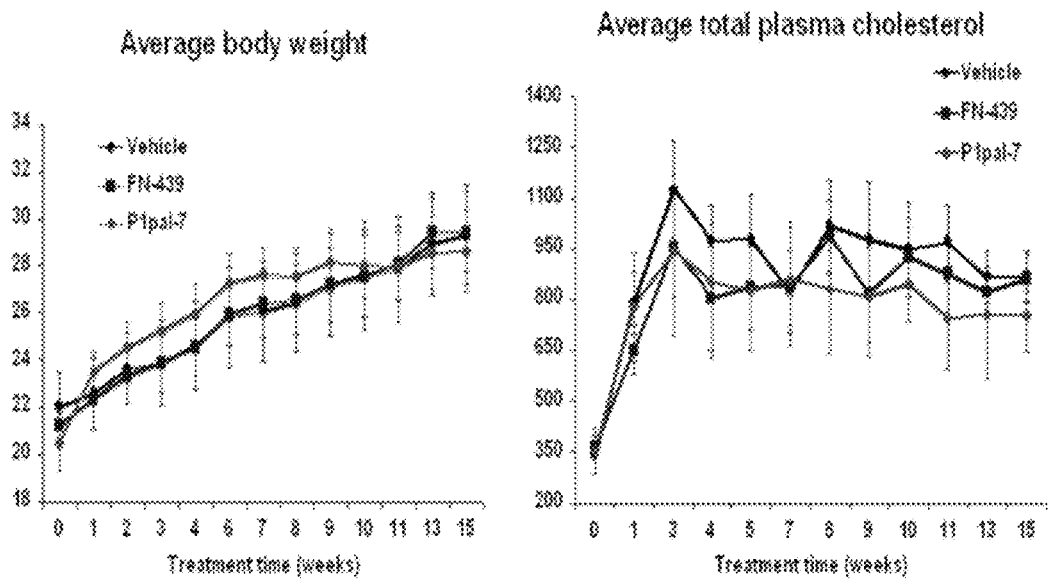
FIG. 10A shows the average weight of ApoE-defident mice after being fed a western diet for 15 weeks.
FIG. 10B shows the total plasma cholesterol of ApoE-deficient mice after being fed a western diet for 15 weeks.

During the 15-week period, the weight of each mouse was measured weekly, after a 4-h fast. There was no significant difference in the mouse weight between the 3 different treatment groups (FIG. 10A), indicating that the treatments did not appear to affect the food intake or health of the mice. The development of atherosclerotic lesions in the apoE-deficient mouse is induced by the accumulation of cholesterol in the blood stream. Therefore, it is of great importance to track the lipid profile of the mice under different treatments. As shown in FIG. 10B, the total plasma cholesterol of the mice increased in the first week of treatment from 350 mg/dl to approximately 600-800 mg/dl and stayed close to 900 mg/dl for the rest of the treatment. Plasma samples were obtained after a 4 h fasting period in the morning of the same day, weekly, in order to exclude possible fluctuations due to food intake. No significant differences were observed between the different treatment groups, indicating that the inhibition of MMPs or PAR1 did not affect the lipid metabolism of the mice.

To study the extent of artherosderotic plaque formation, pinned aortas were first fixed in 10% formalin and kept in 1×PBS. The aorta of the mice were then subjected to "en face" staining with Oil-Red-O, which stains lipids red. Briefly, the PBS was drained from the samples and the stain solution was added for 45 min. The stain was drained and the samples were washed first with 70% Ethanol and then with water, in order to remove the background. Digital pictures of the stained aortas were taken and the the MetaXpress software (Molecular Devices) was used to define and quantify the total aortic area as well as the lesion areas. The ratio of lesion area to the total aortic area was calculated for the "aortic arch/thoracic" and the "abdominal/iliac" area. The aorta of each mouse was isolated and separated into three sections. The abdominal section (before and after the renal arteries) was separated and used for whole mount immunohistochemistry. The remaining sections were the one from the aortic arch to the mesenteric artery (aortic) and the other from after the renal arteries to the iliac arteries (abdominal). These sections of the aorta were used for the "en face" staining and the estimation of the atherosclerotic lesion area.

Figures 11A, 11B:
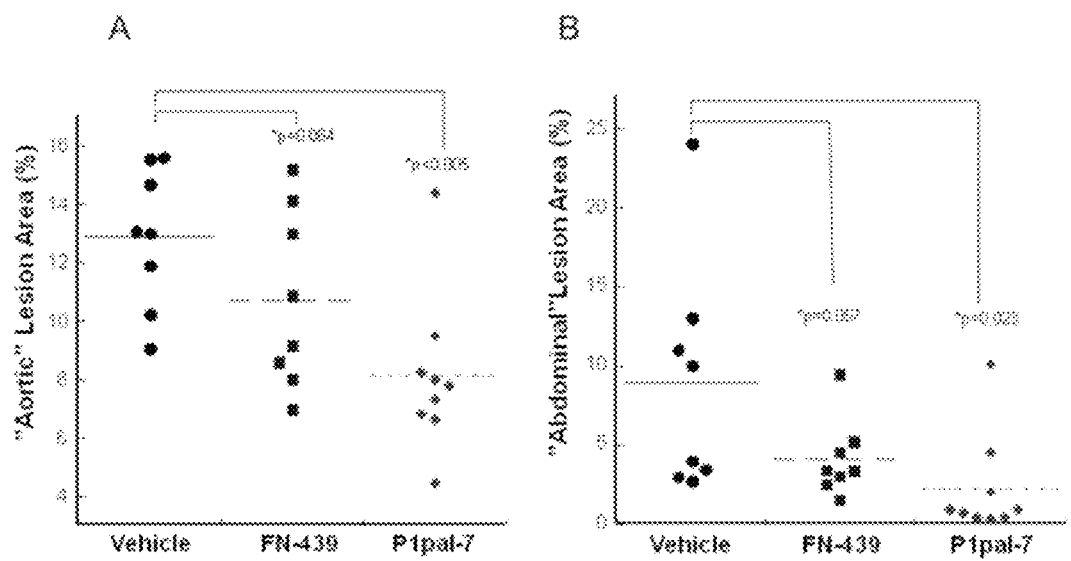
FIG. 11A depicts the atherosclerotic lesion area in ApoE-deficient mice treated with Vehicle, MMP Inh-I (FN-439), or P1pal-7 pepducin lipopeptide.
FIG. 11B depicts atherosclerotic lesion area in the abdominal/iliac aorta.

The lesion area in the aortic and the abdominal sections of the aorta, expressed as a percentage of the total area of the sections, is shown in FIG. 11. In the aortic section, the mean lesion area in the control (vehicle) group is 12.9%, in the FN-439 group is 10.7% and in the P1pal-7 group is 8.1% of the total area. The lesion area in the P1pal-7 group is significantly smaller (p<0.005), compared to the control group.

In the abdominal section of the aorta, the mean lesion area in the control group is 8.9%, in the FN-439 group is 4.1% and in the P1pal-7 group is 2.3%. The lesion area in the P1pal-7 group is significantly smaller (p<0.05), compared to the control group. In both sections, the FN-439 group tends to have a smaller lesion area as compared to the control group, though no significance was reached with the present sample size.

Overall, the inhibition of PAR1 signaling, using the P1pal-7 pepducin lipopeptide, leads to significantly reduced atherosclerotic burden in apoE-deficient mice, while inhibition of the activity of MMPs shows a tendency for smaller atherosclerotic lesions. These findings strongly suggest that PAR1 plays an important role in the progression of atherosclerosis in the aortic vessel. The fact that, unlike humans platelets, mouse platelets do not express PAR1, leads to the conclusion that the above observations are not due to anti-thrombotic action of the pepducin lipopeptide but due to the inactivation of certain pathways in the vascular tissue.

II-(G) Neovascularization

Angiogenesis may promote the progression of atherosclerosis and contribute to plaque instability and rupture. Hence, MMP-PAR1 signaling may be contributing to atherosclerosis formation by stimulating angiogenesis. Angiogenesis was therefore evaluated in the adventitia of aortas from apoE−/− mice fed a high fat diet for 15 weeks and treated with either the MMP-1 collagenase inhibitor, MMP Inh-1 (FN-439) or the PAR1 antagonist, P1pal-7. The mice were then anesthetized with Ketamine/Xylazine and pressure fixed with 10% formalin. The abdominal aorta was isolated, removed and fixed for 1 hour with 10% formalin and adventitial fat was removed. The abdominal aorta were then whole mount immunostained for CD31, a marker for endothelial cells and 3D projection images were constructed from multiple confocal sections using the following procedure. Briefly, the tissue was blocked for 1 hour with 5% goat serum in Tris buffered saline containing 0.3% Triton-X 100 (TBST) and incubated overnight at 4° C. with primary antibody diluted 1:1000 in TBST. After several washes with TBST, the tissue was incubated with fluorescently tagged secondary antibody diluted in TBST for 4 hours. The tissue was washed and post-fixed with 4% paraformaldehyde for 10 minutes. The aorta was then cut lengthwise and splayed open onto a microscope slide with the adventitial side up. The tissue was whole mounted with Vectashield mounting media and imaged using a Leica TCS SP2 confocal microscope (Zeiss). Confocal images were constructed into 3D projections of Z-stacks. Quantification of images was performed using NIH ImageJ. Antibodies used were: hamster anti-mouse PECAM-1 (Chemicon) and Cy3-anti-hamster (Jackson Immunolabs).

Figures 12A, 12B, 12C:
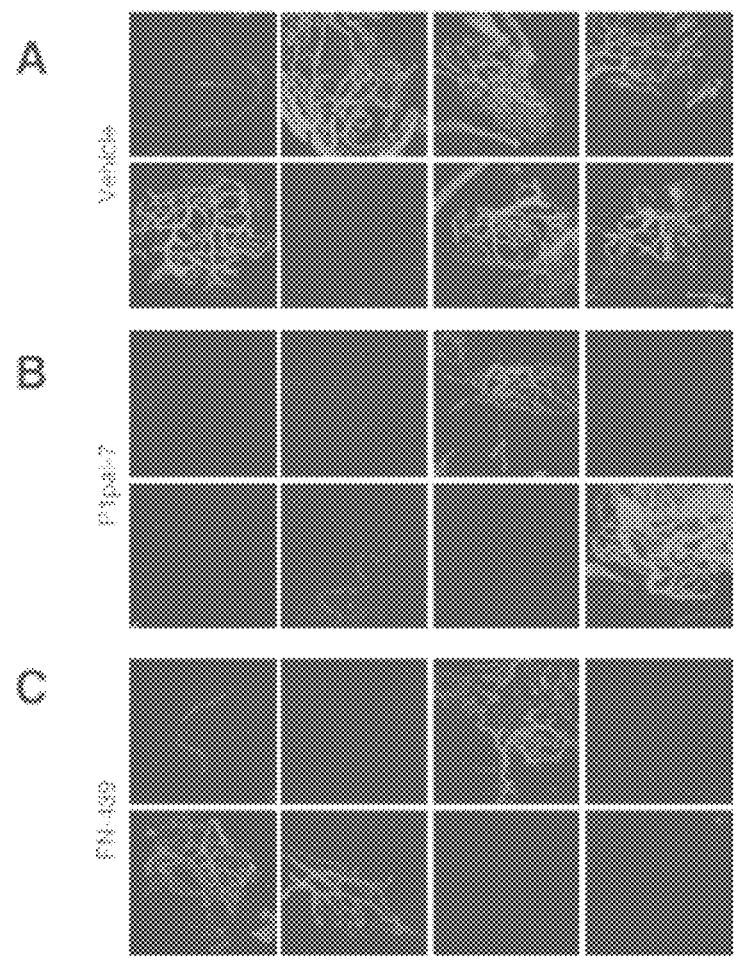
FIGS. 12A-12C show angiogenesis in the abdominal aorta of ApoE−/− Mice.
Figure 13A:
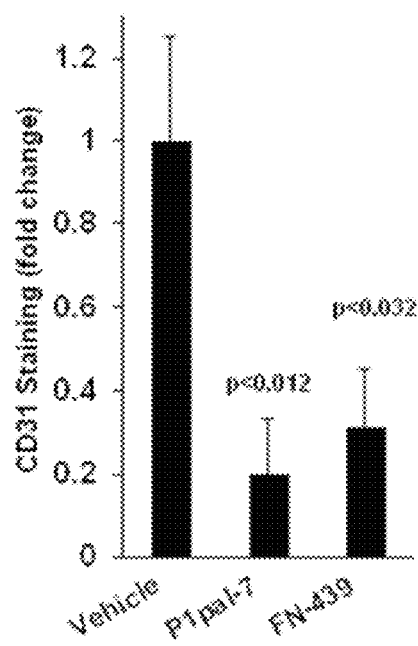
FIGS. 13A-13C shows that P1pal-7 and MMP1 inhibitors reduce angiogenesis in the abdominal aorta of ApoE-deficient mice.
Figure 13B:
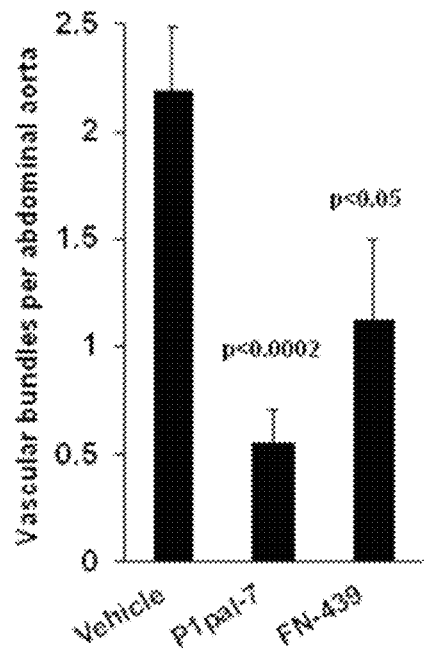
Figure 13C:
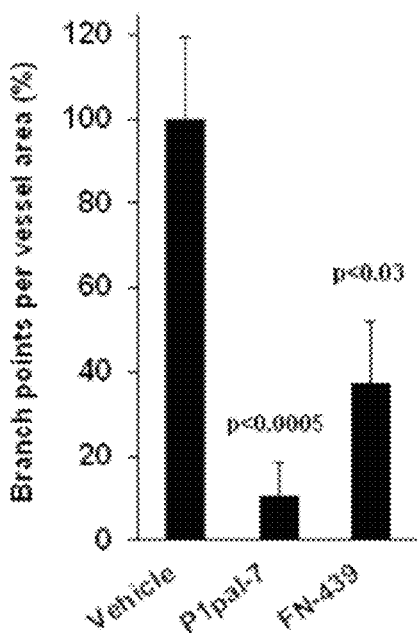

FIG. 12 shows the mount immunostaining for CD31 in the abdominal aorta of ApoE−/− mice treated with vehicle (FIG. 12A), P1pal-7 (FIG. 12B), MMP Inh-I (FN-439) (FIG. 12C) as in FIG. 10. Both P1pal-7 treatment and FN-439 treatment significantly reduced the amount of CD31-positive vessels (FIGS. 12B and 12C). Quantitation of CD31 staining (FIG. 13A) was evaluated in vascular bundles (FIG. 13B), and branch points (FIG. 13C) of the abdominal aorta of ApoE−/− mice treated with vehicle, P1pal-7 or MMP1 Inh-I (FN-439) as in FIG. 10. Angiogenesis was not homogeneous over the entire adventitia of the aorta and vascular bundles appeared in distinct locations, possibly corresponding to locations of atherosclerotic plaques. Both P1pal-7 treatment and FN-439 treatment significantly reduced the number of vascular bundles in the adventitia of the aorta (FIG. 13). To evaluate the structure of the nascent vessels, branch points were counted. P1pal-7 and FN-439 treatment significantly inhibited the number of branch points per vessel area. These findings suggest that both MMP-1 and PAR1 are promoting plaque angiogenesis.

II-(H) Other Inhibitors of MMP-1/PAR-1 Signaling

The MMP-1/PAR-1 signaling pathway may be inhibited in platelets using other potential inhibitors of the MMP-1 PAR-1 signaling pathway, including, but limited to, inhibitors of MMP-1 or MMP-2. The efficacy of these compounds in inhibiting platelet aggregation can be evaluated using the cell-based assays and animals models of a thrombotic disease state described herein.

Since MMPs contain a zinc atom in the catalytic domain and need calcium to function, a chelating compound may inhibit MMP activity. In addition, synthetic derivatives that mimic natural substrates have been designed as MMP inhibitors. Several classes of structures such as carboxylic acid derivatives; heterocyclic structures; hydroxamate moieties with a peptide, peptidomimetic, or nonpeptide backbone; biphenyl moieties with nonpeptide backbone; and tetracycline analogs are the most common low-molecular-weight compounds that have in vitro inhibitory activity against MMPs.

Non-limiting examples of MMP-1 inhibitors include FN-439, tissue inhibitors of metalloprotease (TIMPs), MMP-200, Cipemastat (rINN, also known as Ro 32-3555 and by the tentative trade name Trocade marketed by Roche). Ancorinosides B-D (Fujita et al. Tetrahedron, Vol. 57, Issue 7, 1229-1234, 2001).

Matrix metalloproteinase inhibitors that have entered clinical trials for an oncologic indication include Prinomastat (AG3340; Agouron/Pfizer), BAY 12-9566 (Bayer Corp.), Batimistat (BB-94; British Biotech, Ltd), BMS-275291 (formerly D2163; CelltechlBristol-Myers Squibb), Marimastat (BB 2516; British Biotech, LtdJSchering-Plough), MMI270 (B) (formerly CGS-27023A; Novartis), and Metastat (COL-3; CollaGenex) and Ro 32-3555 & RS-130,830 (Roche Bioscience).

Additional MMP inhibitors that may be used with the compounds and therapeutical applications of this application are disclosed in Design and Therapeutic Application of Matrix Metalloproteinase Inhibitors Mark Whittaker, Floyd at al. Chem. Rev., 1999, 99 (9), 2735-2776 and Prevention of progressive joint destruction in collagen-induced arthritis in rats by a novel matrix metalloproteinase inhibitor, FR255031, Ishikawa et al. British Journal of Pharmacology (2005) 144, 133-143, the contents of which are incorporated herein by reference in their entirety.

Additional MMP inhibitors include PD 166793 (available Axon MedChem; H León et al., Br. J. Pharmacol. (2008) 153, 676-683.

The invention further contemplates other peptide antagonists that interfere with collagen induced platelet activation and may be combined with the herein-described agents that modulate the MMP-1 mediated cleavage of PAR-1 between aspartic acid at position 39 (D39) and proline at position 40 (P40) of said patient's protease-activated receptor-1 (PAR-1). MMP peptide inhibitors based on synthetic triple-helical peptides (THPs) are described in U.S. Patent Application No. 2008/0125354. PAR-1 antibody or peptide antagonists are described in the PCT application WO 2008/011107. The contents of these patent documents are hereby incorporated herein by reference in their entirety.

The invention also provides for combination of the herein described modulators of MMP-1 mediated PAR-1 cleavage with one or more PAR1 pepducin lipopeptides, including those pepducin lipopeptides described in U.S. Patent Publication US200710179090, the contents of which are hereby incorporated herein by reference in its entirety.

Examples of PAR1 pepducin lipopeptides include pepducin lipopeptides comprising a polpeptide sequence taken from the i1, i2, i3 or i4 intracellular loops of PAR-1. In one embodiment, pepducin lipopeptides used herein may have a N-terminal lipid that can be a palmitate, myristate, lithocholate, fatty acids, steriods, etc. In another embodiment, pepducin lipopeptides used herein may have a C-terminal lipid that can be a palmitate, myristate, lithocholate, fatty acids, steriods, etc.

Examples of PAR1 pepducin lipopeptides are depicted in TABLE 1.

TABLE 1

| NAME | TARGET | LOOPS | AMINO ACID SEQUENCE | ATTACHED LIPID |
|---|---|---|---|---|
| P1i3pal-7 (a.k.a. P1pal-7) | PAR1 | i3 | KKSRALF (SEQ ID NO. 2) | palmitate |
| P1i3pal-12 | PAR1 | i3 | RCLSSSAVANRS (SEQ ID NO. 3) | palmitate |
| P1i3pal-12S | PAR1 | i3 | RSLSSSAVANRS (SEQ ID NO. 4) | palmitate |
| P1i3pal-10S | PAR1 | i3 | NRSKKSSALF (SEQ ID NO. 5) | palmitate |
| P1i1pal-11 | PAR1 | i1 | ILKMKVKKPAV (SEQ ID NO. 6) | palmitate |

TABLE 1-continued

| NAME | TARGET | AMINO ACID LOOPS | SEQUENCE | ATTACHED LIPID |
|---|---|---|---|---|
| P1i2pal-7 | PAR1 | i2 | TLGRASF (SEQ ID NO. 7) | palmitate |
| P1i2pal-11 | PAR1 | i2 | LSWRTLGRASF (SEQ ID NO. 8) | palmitate |
| P1i2pal-16 | PAR1 | i2 | YPMQSLSWRTLGRASF (SEQ ID NO. 9) | palmitate |
| P1i2pal-21 | PAR1 | i2 | FLAVVYPMQSLSWRTLGRASF (SEQ ID NO. 10) | palmitate |
| P1i4pal13 | PAR1 | i4 | ASSESQRYVYSIL (SEQ ID NO. 11) | palmitate |
| P1i4pal13R | PAR1 | i4 | LISYVYRQSESSA (SEQ ID NO. 12) | palmitate |

In other embodiments, the invention provides for small molecule inhibitors of PAR-1 signaling activity including, but limited to the compound SCH 530348. SCH 530348 blocks the platelet PAR-1 receptor to which thrombin binds, thus inhibiting thrombin-induced activation of platelets, and is therefore classified as a thrombin-receptor antagonist (TRA). SCH 530348 is further described in Chintala et al. J Pharmacol Sci 108, 433-438 (2008), Chackalamannil et al. J. Med. Chem. 2008, 51, 3061-3064 and the published U.S. patent application, US 2008/0234236, the content of which are hereby incorporated by reference in their entireties. For purposes of this disclosure, reference to the compound SCH 530348 includes all isomers, enantiomers and chemical derivatives of SCH 530348.

In yet another embodiment, an antagonist of the MMP-1 mediated PAR-1 signaling pathway may be a tetracycline compound or tetracycline derivative, such as doxycycline. Tetracyclines are a group of broad-spectrum antibiotics. They are so named for their four ("tetra-") hydrocarbon rings ("-cycl-") derivation ("-ine"). More specifically, they are defined as "a subclass of polyketides having an octahydrotetracene-2-carboxamide skeleton". They are collectively known as derivatives of polycyclic naphthacene carboxamide having the basic structure:

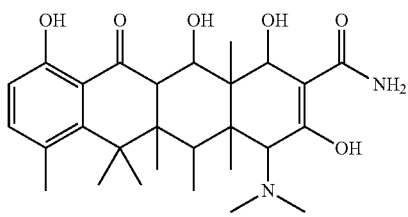 [SMILES: Cc1ccc(O)c2c1C(C)(C)C1(C)C(C2=O)C(O)C2(C)C(O)C(C(N)=O)=C(O)C(N(C)C)C2(C)C1C]

Examples of tetracycline derivatives that may be tested for inhibitory activity on the MMP-1 mediated PAR-1 signaling pathway include, but are not limited to, Chlortetracycline, Oxytetracycline, Demeclocycline, Doxycycline, Lymecycline, Medocycline, Methacycline, Minocycline, Rolitetracycline and Tigecycline. Non-limiting examples of tetracycline derivatives have been described in U.S. Pat. Nos. 2,980,584; 2,990,331; 3,062,717; 3,165,531; 3,454,697; 3,557,280; 3,674,859; 3,957,980; 4,018,889; 4,024,272; and 4,126,680, the contents of which are hereby incorporated herein by reference.

III Drug Administration

Inhibitors of MMP-1 mediated PAR-1 activation may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

Inhibitors of MMP-1 mediated PAR-1 activation include known MMP-1 or PAR-1 inhibitors, as defined herein.

The compounds or "agents" may be used in combination with one or more other known anti-thrombotic agents or pharmaceutical agents, including, e.g., a TP antagonist, a thromboxane antagonist, an ADP receptor antagonist, or a Factor Xa antagonist. When used in combination, it is understood that lower dosages of one or more of the combined anti-thrombotic agents may be utilized to achieve a desired effect, since the two or more anti-thrombotic agents may act additively or synergistically. Accordingly, a therapeutically effective dosage of one or more combined anti-thrombotic agents may correspond to less than 90%, less than 80%, less than 70%, less than 60%, less than 50%, less than 40%, less than 30% or less than 20% of the therapeutically effective dosage when the anti-thrombotic 'agent' is administered alone. The two or more anti-thrombotic agents may be administered at the same time or at different times, by the same route of administration or by different routes of administration. For example, in order to regulate the dosage schedule, the anti-thrombotic agents may be administered separately in individual dosage units at the same time or different coordinated times. The respective substances can be individually formulated in separate unit dosage forms in a manner similar to that described above. However, fixed combinations of the anti-thrombotic agents are more convenient and are preferred, especially in tablet or capsule form for oral administration. Thus, the present invention also provides unit dose formulations comprising two or more anti-thrombotic agents, wherein each thrombotic "agent" is present in a therapeutically effective amount when administered in the combination.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or *acacia*, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum *acacia*; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example *arachis* oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending "agent" and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or *arachis* oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbito or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol. The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic add, polyepsilon caprolactone, polyhydroxy butyric acid, polyorthoesters, polyacetals, polydihydropyrans, polycyanoacrylates and crosslinked or amphipathic block copolymers of hydrogels.

When a composition according to this invention is administered into a human subject, the prescribing physician will normally determine the daily dosage with the dosage generally varying according to the age, weight, and response of the individual patient, as well as the severity of the patient's symptoms. In an embodiment, a suitable amount of an "agent" is administered to a mammal undergoing treatment for thrombosis. Administration occurs in an amount of "agent" of between about 0.1 mg/kg of body weight to about 60 mg/kg of body weight per day, or between 0.5 mg/kg of body weight to about 40 mg/kg of body weight per day. Another therapeutic dosage that comprises the instant composition includes from about 0.01 mg to about 1000 mg of agent. In another embodiment, the dosage comprises from about 1 mg to about 5000 mg of agent.

IV Combination Therapy

One intended use of the herein described PAR-1 signaling agents is the prophylactic treatment of patients at risk of a thrombotic disease state or a recurrence of a thrombotic disease state, such as atherosclerosis. Patients presenting with risk factors such as high blood pressure or high cholesterol levels would be given a therapeutically effective dose of the agent according to a physician prescribed daily regimen. Patients would require close monitoring to ensure the treatment does not incur any undesirable side effects. Appropriate dosage would depend on the severity of any risk factors as well as age, gender of the patient and whether or not the patent has a family history of a thrombotic disease state or other genetic predisposition to a thrombotic disease state. In one embodiment, the herein described agent may be administered prophylactidy to a patient who is at an increased risk of thrombosis, for example, after surgery or after implantation of a medical device such as a stent or artificial organs, such as an artificial heart.

This application further contemplates the combination therapy of the herein described "agent" with one or more drugs that are known to treat one or more risk factors of thrombotic disease state.

In one embodiment, the drugs may be other known inhibitors of platelet activation and aggregation, including, but not limited to, inhibitors of protease activated (PAR) receptors, inhibitors of MMP-1 or MMP-2 activity and inhibitors of thrombin-mediated activation of PAR-1 and combinations thereof.

For example, combination therapy may include known inhibitors of platelet aggregation such as those described in U.S. Pat. Nos. 4,529,596; 4,847,265; 6,429,210B1, 5,288, 726; 6,693,115 and U.S. Patent Applications No. 2008/0214599 or 200310224999, the contents of which are herein incorporated herein in their entirety.

In another example, combination therapy with the herein described "agent" may include known inhibitors of matrix metalloproteinase including, but are not limited to, FN-439, MMP-200 and tissue inhibitors of metalloproteases (TIMPs including TIMP1, TIMP2, TIMP3 and TIMP4). MMP inhibitors are further described in U.S. Pat. No. 3,784,701 and WO 96/15096. MMP peptide inhibitors are described in U.S. Pat. Nos. 5,300,501; 5,530,128; 5,455,258; 5,552,419; WO 95/13289; WO 96/11209 and U.S. Patent Publication No. 2004/0127420, all of which are incorporated herein by reference.

In other examples, combination therapy with the herein described "agent" may include anticoagulants induding, but not limited to, a thrombin inhibitor (e.g., melagatran, E-5555, MCC-977, and bivalirudin (Angiomax™)), Factor Xa inhibitor, tissue factor inhibitor, Factor VIIIa inhibitor, Factor IXa inhibitor, Factor Va inhibitor, Factor XIa inhibitor, Factor XIIa inhibitor, TAFI.alpha. inhibitor, .alpha.2-antiplasmin inhibitor, PAI-1 inhibitor, PAI-2 inhibitor, PAI-3 inhibitor, prothrombinase inhibitor, tick anticoagulation peptide, protein C, warfarin, heparin, lepirudin, aspirin, tidopidine, dopidogrel, tirofiban, and eptifibatide.

In other embodiments, combination therapy with the herein described "agent" may include inhibitors of platelet function, including, but not limited to, GPIIb/IIIa receptor inhibitors, ADP receptors (e.g., P2Y.sub.1, and P2Y.sub.12) inhibitors, thrombin receptor (e.g., PAR-1 and PAR-4) inhibitor, CD40 inhibitors, CD40L (CD40 ligand) inhibitors, Gas6 inhibitors, Gas6 receptor axl inhibitors, Gas6 receptor inhibitors Sky, Gas6 receptors Mer inhibitor, P-selectin inhibitor, P-selectin receptor PSGL-1 inhibitors, thromboxane inhibitors, synthetase inhibitors, fibrinogen receptor antagonists, prostacydin mimetics, phosphodiesterase inhibitors, RANTES inhibitor, phosphoinositide-3-kinase (PI(3)K) isoform .beta. inhibitors, phosphoinositide-3-kinase (PI(3)K) isoform.gamma. inhibitors, eptifibatide, tirofiban, tidopidine, and dopidogrel.

In other embodiments, the "agent" described herein may be combined with known drugs that a physician may use to treat medical conditions known to increase the risk of cardiovascular disease. For example, the herein described "agent" may be combined with a HMG-CoA reductase inhibitor, otherwise known as a statin, including, but are not limited to, simvastatin, pravastatin, rivastatin, mevastatin, fluindostatin, cerivastatin, velostatin, fluvastatin, dalvastatin, dihydrocompactin, compactin, or lovastatin; or a pharmaceutically acceptable salt of simvastatin, pravastatin, rivastatin, cerivastatin, mevastatin, fluindostatin, velostatin, fluvastatin, dalvastatin, dihydrocompactin, compactin, lovastatin, or pharmaceutically acceptable salts thereof. Similar combination therapy regimens using statins are disclosed in U.S. Patent Publication No. 2005/0020607, the contents of which are hereby incorporated herein by reference in its entirety.

In certain embodiments, the combination therapy with the herein described 'agent' may include a known drug that is used to prevent or treat a thrombotic disease state. Preferably, though not necessarily, the drug may be one that has already been deemed safe and effective for use in humans or animals by the appropriate governmental agency or regulatory body. For example, drugs approved for human use are listed by the FDA under 21 C.F.R. sections 330.5, 331 through 361, and 440 through 460, incorporated herein by reference; drugs for veterinary use are listed by the FDA under 21 C.F.R. sections 500 through 589, incorporated herein by reference.

V Diagnostic Kits

A variety of methods can be used to determine the level of activated PAR-1 in platelets taken from a patient. In general, these methods include contacting an agent that selectively binds to the MMP-1 mediated PAR-1 peptide (residues 1-39), such as an antibody with a sample, to evaluate the level of the peptide in the sample. In another embodiment, the methods detect MMP-1 cleaved PAR-1 or parameters associated with PAR-1 activation. In a preferred embodiment, the antibody bears a detectable label. Antibodies can be polydonal, or more preferably, monoclonal. An intact antibody, or a fragment thereof (e.g., Fab or F(ab)2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance.

In vitro techniques for detection of PAR-1(1-39) peptide or MMP-1 cleaved PAR-1 include enzyme linked immunosorbent assays (ELISAs), immunoprecipitations, immunofluorescence, enzyme immunoassay (EIA), radioimmunoassay (RIA), and western blot analysis.

The invention also includes kits for detecting the presence of activated PAR-1 in a biological sample. For example, the kit can include a compound or agent capable of detecting PAR-1 peptide (1-39) or MMP-1 cleaved PAR-1 in a biological sample and a standard. The compound or agent can be packaged in a suitable container. The kit can further comprise instructions for using the kit to detect PAR-1 peptide (1-39) or MMP-1 cleaved PAR-1.

For antibody-based kits, the kit can include: (1) a first antibody (e.g., attached to a solid support) which binds to a PAR-1 (1-39) peptide; and, optionally, (2) a second, different antibody which binds to either the peptide or the first antibody and is conjugated to a detectable agent. The kit can also include a buffering agent, a preservative, or a protein stabilizing agent. The kit can also include components necessary for detecting the detectable agent (e.g., an enzyme or a substrate). The kit can also contain a control sample or a series of control samples, which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing a thrombotic disease state. The prognostic assays described herein can be used to determine whether a subject can be administered an agent (e.g., a antagonist, peptidomimetic, protein, peptide, nucleic acid, small molecule, or other drug candidate).

In another aspect, the invention features a computer medium having a plurality of digitally encoded data records. Each data record includes a value representing the level of activated PAR-1 in a sample, and a descriptor of the sample. The descriptor of the sample can be an identifier of the sample, a subject from which the sample was derived (e.g., a patient), a diagnosis, or a treatment (e.g., a preferred treatment).

In a preferred embodiment, the data record further includes values representing the level of other risk factors associated with a thrombotic disease state. The data record can be structured as a table, e.g., a table that is part of a database such as a relational database (e.g., a sql database of the oracle or sybase database environments).

Also featured is a method of evaluating a sample. The method includes providing a sample, e.g., from the subject, and determining PAR-1 activation. The method can further include comparing the value or the profile (i.e., multiple values) to a reference value or reference profile.

The method can be used to diagnose and monitor a thrombotic disease state in a subject wherein an increase or decrease in PAR-1 activation is an indication that the subject has or is disposed to having a thrombotic disease state. The method can also be used to monitor treatment of a thrombotic disease state in a subject. The PAR-1 activation profile can be compared to a reference profile or to a profile obtained from the subject prior to treatment or prior to onset of the disorder.

In another aspect, the invention features, a method of evaluating a subject. The method includes: a) obtaining a sample from a subject, e.g., from a caregiver, e.g., a caregiver who obtains the sample from the subject; b) determining a PAR-1 activation profile for the sample. Optionally, the method further includes either or both of steps: c) comparing the subject profile to one or more reference profiles; and d) selecting the reference profile most similar to the subject reference profile. A variety of routine statistical measures can be used to compare two reference profiles.

The invention also contemplates kits for the detection of polymorphism(s) in MMP-1 genes and associated factors (such natural MMP-1 inhibitors such TIMPs) that may predispose a patient to a thrombotic disease state. Several polymorphisms in the promoters of a number of MMP genes, including MMP-1, have been well characterized. These polymorphisms are thought to affect the respective MMP production in an allele-specific manner. For example, the promoter region of the MMP-1 gene contains consensus sequences for DNA-binding proteins such as AP-1, AP-2, EtsIPEA-3, and responsive elements to glucocorticoids, retinoic acid, and cyclic AMP (Rutter et al, 1997). A single nucleotide polymorphism (SNP) has been identified at position ~1607 bp within the MMP-1 promoter region, whereby the insertion of an additional guanine (G) residue creates an extra Ets-binding site (Rutter et al, (1998) Cancer Res 58: 5321-5325). A promoter containing this SNP (giving rise to the 2G genotype) displays significantly 'higher' transcriptional activity in normal and malignant cells compared to cells possessing a 1G allele (Rutter et al, 1998; Wyatt et al, (2002) Cancer Res 62: 7200-7202) with 'lower' transcriptional activity. Hence, this MMP-1 polymorphism may be a predictor of an innate predisposition to a thrombotic disease state.

Kit components for the detection of polymorphism are well known in the art and may include polymorphism specific primers and reagent for PCT amplification.

VI Platelet Storage Medium

Platelets can be obtained as a by-product from whole blood donations and from plateletpheresis. Donated blood is typically processed to separate various blood components including platelets that can be separately used. For example, a unit of donated whole blood can be processed to separate red cells, usually concentrated as packed red cells (prc), platelets, usually concentrated as platelet concentrate (PC), and plasma. In accordance with typical processing protocols, blood can be processed to form, among other fractions, a platelet-containing fluid, e.g., platelet-rich-plasma (PRP) or buffy coat, that are further processed (including centrifugation) to form the PC. Moreover, multiple units of platelets or buffy coat can be pooled before producing the final transfusion product.

In accordance with current conventional blood banking practice, pc produced in a dosed (sterile) system can be stored for up to only 5 days before being used as a transfusion product. In some processing protocols, a platelet additive solution is added to the platelet-containing fluid (e.g., the buffy coat) and the platelets are resuspended in the additive solution before the platelets are stored, wherein most of the plasma is removed before the additive solution is added. Alternatively, platelets can be stored in their own plasma.

In order to provide optimal platelet function and viability during storage, it is recommended that the platelet-containing fluid (with or without an additive solution) be maintained at a ph in the range of from 6.8 to 7.4 (European practice), or maintained at a ph of 6.2 or greater (us practice) during the storage period. It is also recommended that the platelets be stored in the presence of glucose or dextrose to maintain platelet quality. In addition, platelets may become activated during the processing of blood to concentrate the platelets (including during the subsequent resuspension of the platelets in the additive solution), leading to platelet aggregation and loss of viability. Hence, common components added to the platelet storage medium include an anticoagulant, typically a citrate.

Further examples of the medium and methods commonly used in blood donation, preparation, storage and transportation can be found in a variety of literatures, e.g., "Textbook Of Blood Banking And Transfusion Medicine" written by Sally v. Rudmann, and published by Elsevier Health Sciences, 2005.

Based on the present discovery of the role of MMP-1 activated PAR-1 in platelet aggregation, an aspect of the present invention is to provide in a platelet-containing medium, at any time during the preparation, storage or transportation of such a medium, the "agent" of the present invention, which substantially inhibits proteolytic cleavage between the aspartic add at position 39 (d39) and the proline at position 40 (p40) of the PAR-1 on the platelets surface. In an embodiment, the "agent" of the invention inhibits activation of MMP-1 or MMP-1 enzymatic activity. In an another embodiment, the "agent" may inhibit PAR-1 signaling activity after proteolytic cleavage between the aspartic acid at position 39 (d39) and the proline at position 40 (p40) of the PAR-1. The "agent" of the invention can be added to a platelet-storage medium in addition to or in place of a more conventional anti-coagulant. In an embodiment, the storage medium with the "agent" of the invention prolongs the shelf-life of platelets contained therein beyond the current 5 days at room temperature (about 22° C.), e.g., by 0.5, 1, 2, 3, 4, 5, 6, or even 7 days.

VII Medical Devices

Surfaces of implantable medical devices such as stents

The compound described herein made used alone or in combination with other know anti-thrombotic agents to coat medical devices.

Methods of coating are well known in the art. For example, PCT application WO2005/097223 A1-Stucke et al, discloses a method wherein a mixture of heparin conjugated with photoactive crosslinkers with dissolved or dispersed with other durabal polymers such as Poly(butyl methacrylate) and poly(vinyl pyrrolidone) in a same coating solution and crosslinked with UV light in the solution or after the coating is applied.

Another general approach as disclosed in US 200510191333 A1, US 2006/0204533 A1, and WO 2006/099514 A2, all by Hsu, Li-Chien, et al., uses a low molecular weight complex of heparin and a counter ion (stearylkonium heparin), or a high molecular weight polyelectrolyte complex, such as dextran, pectin to form a complex form of an anti-thrombotic entity. These anti-thrombotic complexes are further dispersed in a polymer matrix that may further comprise a drug.

U.S. Published Patent application No. 2008/0269875 also discloses methods of applying multiple layers of polymeric compositions to a medical device. One layer may comprise a base coat that allows additional layers to adhere thereto. An additional layer(s) can carry bioactive agents within their polymer matrices.

The contents of these patent documents are hereby incorporated herein by reference in their entirety.

VIII Other Therapeutic Applications

MMP-1/PAR-1 test compounds described herein may also find uses for the diagnosis and treatments of other medical conditions associated with PAR-1 activation. For example, medical conditions that may benefit from the compounds described herein, include, but not limited to, chronic intestinal inflammatory disorders, including inflammatory bowel disease (IBD), irritable bowel syndrome (IBS) and ulcerative colitis and fibrotic disorders, including liver fibrosis and lung fibrosis (see, for example, Vergnolle, et al., J Clin Invest (2004) 114(10): 1444; Yoshida, et al, Aliment Pharmacol Ther (2006) 24(Suppl 4):249; Mercer, et al, Ann NY Acad Sd (2007) 1096:86-88; Sokolova and Reiser, Pharmacol Ther (2007) PMID: 17532472), ischemia-reperfusion injury, including myocardial, renal, cerebral and intestinal ischemia-reperfusion injury (see, for example, Strande, et al., Basic Res. Cardiol (2007) 102(4):350-8; Sevastos, et al., Blood (2007) 109(2):577-583; Junge, et al., Proc Natl Acad Sci USA. (2003) 100(22): 13019-24 and Tsuboi, et al., Am J Physiol Gastrointest Liver Physiol (2007) 292(2):G678-83. Inhibiting PAR1 intracellular signaling can also be used to inhibit herpes simple virus (HSVI and HSV2) infection of cells. See, Sutherland, et al., J Thromb Haemost (2007) 5(5): 1055-61), in the pathogenesis of neurodegenerative diseases including Alzheimer's disease (AD) and Parkinson's disease (see Nishimura at al. Cell, Vol. 116, Issue 5, 671-682. (2004). Ishida et al. J Neuropathol Exp Neurol. 2006 January; 65(1): 6677; Rosenberg (2009) The Lancet Neurology, Vol. 8, 205-216, sepsis (Kaneider et al., Nature Immunology 8, 1303-1312 (2007)) or endometriosis (Hirota et al. J Clin Endocrinol Metab 2005; 90(6):3673-3679), cancer and angiogenesis (reviewed by Tsopanoglou N E and Maragoudakis M E. Semin Thromb Hemost. 2007 October; 33 (7):680-7).

The biology and pathophysiology of PAR activation in different tissues, cells, and species was recently reviewed by Steinhoff et al. Endocrine Reviews, February 2005, 26(1): 1-43.

Any patent, patent application, publication, or other disclosure material identified in the specification is hereby incorporated by reference herein in its entirety. Any material, or portion thereof, that is said to be incorporated by reference herein, but which conflicts with existing definitions, statements, or other disclosure material set forth herein is only incorporated to the extent that no conflict arises between that incorporated material and the present disclosure material.

Sequence listings and related materials in the ASCII text file named "TMC0407US2_Seq.txt" and created on Oct. 9, 2014 with a size of about 12 kilobytes, is hereby incorporated by reference.

REFERENCES

Bergmeier, W., Burger. P. C., Piffath, C. L., Hoffmeister, K. M., Hartwig, J. H., Nieswandt, B., and Wagner, D. D. (2003). Metalloproteinase inhibitors improve the recovery and hemostatic function of in vitro-aged or -injured mouse platelets. Blood 102, 4229-4235.

Bergmeier, W., Rabie, T., Strehl, A., Piffath, C. L., Prostredna, M., Wagner, D. D., and Nieswandt, B. (2004). GPVI down-regulation in murine platelets through metalloproteinase-dependent shedding. Thromb Haemost 91, 951-958.

Berman. J., Green, M., Sugg, E., Anderegg, R., Millington, D. S., Norwood, D. L., McGeehan, J., and Wiseman. J. (1992). Rapid optimization of enzyme substrates using defined substrate mixtures. J Biol Chem 267, 1434-1437.

Bhatt, D. L., and Topol, E. J. (2003). Scientific and Therapeutic Advances in Antiplatelet Therapy. Nature Rev Drug Discovery 2, 15-28.

Boire, A., Covic, L., Agarwal, A., Jacques, S., Sharifi, S., and Kuliopulos, A. (2005). PAR1 is a Matrix Metalloprotease-1 Receptor that Promotes Invasion and Tumorigenesis of Breast Cancer Cells. Cell 120, 303-313.

Chang, J. Y. (1985). Thrombin specificity. Requirement for apolar amino acids adjacent to the thrombin cleavage site of polypeptide substrate. Eur J Biochem 151, 217-224.

Chackalamannil S, Wang Y, Greenlee W J, Hu Z, Xia Y, Ahn H S, Boykow G, Hsieh Y, Palamanda J, Agans-Fantuzzi J, Kurowski S, Graziano M. Chintala M. (2008) Discovery of a novel, orally active himbadne-based thrombin receptor antagonist (SCH 530348) with potent antiplatelet activity. J Med Chem. June 12; 51(11):3061-4

Chackalamannil S, Wang Y, Greenlee W J, Hu Z, Xia Y, Ahn H S, Boykow G, Hsieh Y, Palamanda J, Agans-Fantuzzi J, Kurowski S, Graziano M, Chintala M. Chesney, C. M., Harper, E., and Colman, R. W. (1974). Human platelet collagenase. J Clin Invest 53, 1647-1654.

Chintala M., Shimizu K., Ogawa M., Yamaguchi H., Doi M., and Jensen P. (2008) Basic and Translational Research on Proteinase-Adivated Receptors: Antagonism of the Proteinase-Activated Receptor 1 for Thrombin, a Novel Approach to Antiplatelet Therapy for Atherothrombotic Disease J Pharmacol Sci 108, 433-438

Conant, K., Hillaire, C. S., Nagase, H., Visse, R., Gary. D., Haughey, N., Anderson. C. Turchan, J., and Nath, A. (2004). Matrix metalloproteinase 1 interacts with neuronal integrins and stimulates dephosphorylation of Akt. J Biol Chem 279, 8056-8062.

Coughlin, S. R. (2000). Thrombin signalling and protease-activated receptors. Nature 407, 258-264.

Covic, L., Gresser. A. L., Talavera, J., Swift, S., and Kuliopulos, A. (2002a). Activation and inhibition of G protein-coupled receptors by cell-penetrating membrane-tethered peptides. Proc Nati Acad Sci (USA) 99, 643-648.

Dollery, C. M., and Libby, P. (2006). Atherosclerosis and proteinase activation. Cardiovasc Res 69, 625-635.

Dumin, J. A., Dickeson, S. K., Stricker, T. P., Bhattacharyya-Pakrasi, M., Roby, J. D., Santoro, S. A., and Parks, W. C. (2001). Pro-collagenase-1 (matrix metalloproteinase-1) binds the alpha(2)beta(1) integrin upon release from keratinocytes migrating on type I collagen. J Biol Chem 276, 29368-29374.

Egeblad, M., and Werb, Z. (2002). New Functions for the Matrix Metalloproteinases in Cancer Progression. Nature Rev Cancer 2, 161-174.

Fressinaud, E., Sakariassen, K. S., Rothschild, C., Baumgartner, H. R., and Meyer. D. (1992). Shear rate-dependent impairment of thrombus growth on collagen in nonanticoagulated blood from patients with von Willebrand disease and hemophilia A. Blood 80, 988-994.

Furie, B., and Furie, B. C. (2008) Mechanisms of Thrombus Formation. N. Engl. J. Med. 359: 938-49.

Gait, S. W., Lindemann, S., Allen, L., Medd, D. J., Falk, J. M., McIntyre, T. M., Prescott, S. M., Kraiss, L. W., Zimmerman, G. A., and Weyrich, A. S. (2002). Outside-in signals delivered by matrix metalloproteinase-1 regulate platelet function. Circ Res 90, 1093-1099.

Gast, A., Tschopp, T. B., and Baumgartner, H. R. (1994). Thrombin plays a key role in late platelet thrombus growth and/or stability. Effect of a specific thrombin inhibitor on thrombogenesis induced by aortic subendothelium exposed to flowing rabbit blood. Arteriosder Thromb 14, 1466-1474.

Giesen, P. L., Rauch, U., Bohrmann, B., Kling, D., Roque, M., Fallon, J. T., Badimon, J. J., Himber, J., Riederer, M. A., and Nemerson, Y. (1999). Blood-borne tissue factor: another view of thrombosis. Proc Natl Acad Sci USA 96, 2311-2315.

Glass, C. K., and Witztum, J. L. (2001). Atherosclerosis, the road ahead. Cell 104, 503-516.

Gogly, B., Groult, N., Homebeck, W., Godeau, G., and Pellat, B. (1998). Collagen zymography as a sensitive and specific technique for the determination of subpicogram levels of interstitial collagenase. Anal Biochem 255, 211-216.

He, L., Pappan, L. K., Grenache, D. G., Li, Z., Tollefsen, D. M., Santoro, S. A., and Zutter, M. M. (2003). The contributions of the $a_2b_1$ integrin to vascular thrombosis in vivo. Blood 102, 3652-3657.

Huang, J. S., Dong, L., Kozasa, T., and Le Breton. G. C. (2007). Signaling through G(alpha)13 switch region I is essential for protease-activated receptor 1-mediated human platelet shape change, aggregation, and secretion. J Biol Chem 282, 10210-10222.

Huebner, J. L., Ottemrness, I. G., Freund, E. M., Caterson, B., and Kraus, V. B. (1998). Collagenase 1 and collagenase 3 expression in a guinea pig model of osteoarthritis. Arthritis Rheum 41, 877-890.

Inauen, W., Baumgartner, H. R., Bombeli, T., Haeberli, A., and Straub, P. W. (1990). Dose- and shear rate-dependent effects of heparin on thrombogenesis induced by rabbit aorta subendothelium exposed to flowing human blood. Arteriosclerosis 10, 607-615.

Jackson, S. P., Nesbitt, W. S., and Kulkarni, S. (2003). Signaling events underlying thrombus formation. J Thromb Haemost 1, 1602-1612.

Kaneider, N. C., Leger, A. J., Agarwal, A., Nguyen, N., Perides, G., Derian, C., Covic, L., and Kuliopulos, A. (2007). Role reversal for the receptor PAR1 in sepsis-induced vascular damage. Nature Imm 8, 1303-1312.

Kazes, I., Elalamy, I., Sraer, J. D., Hatmi, M., and Nguyen, G. (2000). Platelet release of trimolecular complex components MT1-MMP/TIMP2/MMP2: involvement in MMP2 activation and platelet aggregation. Blood 96, 3064-3069.

Kuliopulos, A., Covic, L., Seeley, S. K., Sheridan, P. J., Helin, J., and Costello, C. E. (1999). Plasmin Desensitization of the PAR1 Thrombin Receptor: Kinetics, Sites of Truncation, and Implications for Thrombolytic Therapy. Biochemistry 38, 4572-4585.

Kuliopulos, A., Mohanlal, R., and Covic, L. (2004). Effect of Selective Inhibition of the p38 MAP Kinase Pathway on Platelet Aggregation. Thromb Haemost 92, 1387-1393.

Leger, A., Jacques, S. L., Badar, J., Kaneider, N. C., Derian, C. K., Andrade-Gordon, P., Covic, L., and Kuliopulos, A. (2006a). Blocking the Protease-Activated Receptor 1-4 Heterodimer in Platelet-Mediated Thrombosis. Circulation 113, 1244-1254.

Leger, A. J., Covic, L., and Kuliopulos, A. (2006b). Protease-Activated Receptors and Cardiovascular Diseases. Circulation 113, 1070-1077.

Levy, G. G., Nichols, W. C., Lian, E. C., Foroud, T., McClintick, J. N., McGee. B. M., Yang. A. Y., Siemieniak, D. R., Stark, K. R., Gruppo, R., et al. (2001). Mutations in a member of the ADAMTS gene family cause thrombotic thrombocytopenic purpura. Nature 413, 488-494.

Loew, D., Perrault, C., Morales, M., Moog, S., Ravanat, C., Schuhler, S., Arcone, R., Pietropaolo, C., Cazenave, J. P., van Dorsselaer, A., et al. (2000). Proteolysis of the exodomain of recombinant protease-activated receptors: prediction of receptor activation or inactivation by MALDI mass spectrometry. Biochemistry 39, 10812-10822.

Mackman, N. (2004). Role of tissue factor in hemostasis, thrombosis, and vascular development. Arterioscier Thromb Vasc Biol 24, 1015.1022.

Mann, K. G., Whelihan, M. F., Butenas, S., and Orfeo, T. (2007). Citrate anticoagulation and the dynamics of thrombin generation. J Thromb Haemost 5, 2055-2061.

Moers, A., Nieswandt, B., Massberg, S., Wettschureck, N., Gruner, S., Konrad, I., Schulte, V., Aktas, B., Gratacap, M. P., Simon, M. I., et al. (2003). G13 is an essential mediator of platelet activation in hemostasis and thrombosis. Nat Med 9, 1418-1422.

Netzel-Amett, S., Fields. G. B., Birkedal-Hansen, H., Van Wart, H. E., and Fields, G. (1991). Sequence specificities of human fibroblast and neutrophil collagenases [published erratum appears in J Biol Chem 1991 Nov. 5; 266 (31):21326]. J Biol Chem 266, 6747-6755.

Nieswandt, B., and Watson, S. P. (2003). Platelet-collagen interactions: is GPVI the central receptor? Blood 102, 449-461.

Odake, S., Morita, Y., Morikawa, T., Yoshida, N., Hori, H., and Nagai, Y. (1994). Inhibition of matrix metalloproteinases by peptidyl hydroxamic acids. Biochem Biophys Res Commun 199, 1442-1446.

Offermanns, S., Laugwitz, K.-L., Spicher, K., and Schultz, C. (1994). G Proteins of the Gr Family are Activated Via Thromboxane A$_2$ and Thrombin Receptors in Human Platelets. Proc Nati Acad Sci (USA) 91, 504-508.

Okorie, U. M., Denney, W. S., Chatterjee, M. S., Neeves, K. B., and Diamond, S. L. (2008). Determination of surface tissue factor thresholds that trigger coagulation at venous and arterial shear rates: amplification of 100 fM circulating tissue factor requires flow. Blood 111, 3507-3513.

Parry, M. A. A., Myles, T., Tschopp, J., and Stone, S. R. (1996). Cleavage of the Thrombin Receptor: Identification of Potential Activators and Inactivators. Biochem J 320, 335-341.

Pearce, E., Tregouet, D. A., Samnegard, A., Morgan, A. R., Cox, C., Hamsten, A., Eriksson, P., and Ye, S. (2005). Haplotype effect of the matrix metalloproteinase-1 gene on risk of myocardial infarction. Circ Res 97, 1070-1076.

Rand, M. D., Lock, J. B., Veer, C. V.t., Gaffney, D. P., and Mann, K. G. (1996). Blood Clotting in Minimally Altered Whole Blood. Blood 88, 3432-3445.

Ruggeri, Z. M. (2002). Platelets in atherothrombosis. Nature Med 8, 1227-1234.

Rutter J L, Mitchell T I, Buttice G, Meyers J, Gusella J F, Ozelius L J, Brinckerhoff C E (1998) A single nucleotide polymorphism in the matrix metalloproteinase-1 promoter creates an Ets binding site and augments transcription. Cancer Res 58: 5321-5325

Sawicki, G., Salas, E., Murat. J., Miszta-Lane, H., and Radomski, M. W. (1997). Release of gelatinase A during platelet activation mediates aggregation. Nature 386, 616-619.

Schwertz, H., Tolley, N. D., Foulks, J. M., Denis, M. M., Risenmay, B. W., Buerke, M., Tilley, R. E., Rondina, M. T., Harris, E. M., Kraiss, L. W., et al. (2006). Signal-dependent splicing of tissue factor pre-mRNA modulates the thrombogenicity of human platelets. J Exp Med 203, 2433-2440.

Seeley, S., Covic. L., Jacques, S. L., Sudmeier. J., Baleja. J. D., and Kuliopulos, A. (2003). Structural Basis for Thrombin Activation of a Protease-Activated Receptor: Inhibition of Intramolecular Liganding. Chemistry & Biology 10, 1033-1041.

Steinhubl, S. R., Schneider, D. J., Berger, P. B., and Becker, R. C. (2007). Determining the efficacy of antiplatelet therapies for the individual: lessons from clinical trials. J Thromb Thrombolysis.

Stephens, G., Yan, Y., Jandrot-Perrus, M., Villeval, J. L., Clemetson, K. J., and Phillips, D. R. (2004). Platelet activation induces metalloproteinase-dependent GP VI cleavage to down-regulate platelet reactivity to collagen. Blood 105, 186-191.

Sukhova. G. K., Schonbeck, U., Rabkin, E., Schoen, R. J., Poole, A. R., Billinghurst. R. C., and Libby, P. (1999). Evidence for Increased Collagenolysis by Interstitial Collagenases-1 and -3 in Vulnerable Human Atheromatous Plaques. Circulation 99.

Sundaresan, P., and Farndale, R. W. (2002). p38 mitogen-activated protein kinase dephosphorylation is regulated by protein phosphatase 2A in human platelets activated by collagen. FEBS letts 528, 139-144.

Suzuki, H., Kusuyama, T., Sato, R., Yokota, Y., Tsunoda, F., Sato, T., Shoji, M., Iso, Y., Koba, S., and Katagiri, T. (2008). Elevation of matrix metalloproteinases and interleukin-6 in the culprit coronary artery of myocardial infarction. Eur J Clin Invest 38, 166-173.

Turk, B. E., Huang, L. L., Piro, E. T., and Cantley, L. C. (2001). Determination of protease cleavage site motifs using mixture-based oriented peptide libraries. Nat Biotech 19, 661-667.

Veen, G., Meyer, A., Verheugt, F. W., Werter, C. J., de Swart, H., Lie, K. I., van der Pol, J. M., Michels, H. R., and van Eenige, M. J. (1993). Culprit lesion morphology and stenosis severity in the prediction of reocdusion after coronary thrombolysis: angiographic results of the APRICOT study. Antithrombotics in the Prevention of Reocclusion in Coronary Thrombolysis. J Am Coll Cardiol 22, 1755-1762.

Vu, T.-K. H., Hung, D. T., Wheaton, V. I., and Coughlin, S. R. (1991). Molecular Cloning of a Functional Thrombin Receptor Reveals a Novel Proteolytic Mechanism of Receptor Action. Cell 64, 1057-1068.

Wyatt C A, Coon C I, Gibson J J, Brinckerhoff C E (2002) Potential for the 2G single nucleotide polymorphism in the promoter of matrix metalloproteinase to enhance gene expression in normal stromal cells. Cancer Res 62: 7200-7202.

The invention claimed is:

1. A method of treating a thrombotic disease state in a patient, said method comprising administering to a patient diagnosed with or at substantial risk of developing a thrombotic disease state a therapeutically effective amount of an agent that substantially inhibits said patient's protease-activated receptor-1(PAR-1) signaling activity that results from a proteolytic cleavage by matrix metalloprotease-1 (MMP-1) between aspartic acid at position 39(D39) and proline at position 40 (P40) of said patient's protease-activated receptor-1 (PAR-1).

2. The method of claim 1, wherein said thrombotic disease state comprises a pathology resulting from platelet aggregation.

3. The method of claim 2, wherein said pathology is selected from the group consisting of acute coronary syndrome, arterial thrombosis, venous thrombosis, peripheral arterial disease, unstable angina, atrial fibrillation, first myocardial infarction, recurrent myocardial infarction, ischemic sudden death, transient ischemic attack, stroke, atherosclerosis, deep vein thrombosis, thrombophlebitis, arterial embolism, coronary arterial thrombosis, cerebral arterial thrombosis, cerebral embolism, kidney embolism and pulmonary embolism.

4. The method of claim 1, wherein said patient is diagnosed with cancer.

5. The method of claim 1, wherein said administration of said agent substantially inhibits platelet activation in said patient.

6. The method of claim 1, further comprising administering to said patient a second agent that substantially inhibits thrombin-dependent activation of PAR1.

7. The method of claim 1, further comprising administering to said patient a second anti-thrombotic agent.

8. The method of claim 7, wherein said second anti-thrombotic agent is selected from the group consisting of anti-platelet drugs, anticoagulant drugs, and thrombolytic drugs.

9. The method of claim 7, wherein said second anti-thrombotic agent is selected from the group consisting of thienopyridines, prostaglandin analogs, COX inhibitors, vitamin K antagonists, glycoprotein IIB/IIIA inhibitors and thrombin inhibitors.

10. The method of claim 7, wherein said second anti-thrombotic agent is selected from the group consisting of aspirin, clopidogrel, ticlopidine, prasugrel, heparin, abciximab, eptifibatid, tirofiban and bivalirudin.

11. The method of claim 1, wherein said agent comprises a pepducin lipopeptide of a PAR family member.

12. The method of claim 11, wherein said pepducin lipopeptide of a PAR family member comprises a PAR-1 pepducin lipopeptide.

13. The method of claim 12, wherein said PAR-1 pepducin lipopeptide is selected from the group consisting of Pli3pal-7, Pli3pal-12, Pli3pal-12S, Pli3pal-10S, Pli1pal-11, Pli2pal-7, Pli2pal-11, Pli2pal-16, Pli2pal-21, Pli4pal13 and Pli4pal13R.

14. The method of claim 1, wherein said agent is administered through a means selected from the group consisting of intravenous (I.V.) injection, subcutaneous injection, intramuscular injection, oral ingestion, nasal, topical, rectal, vaginal and parenteral intake.

15. The method of claim 1, wherein said agent is formulated with a pharmaceutically acceptable excipient, carrier or diluent.

16. A method of treating atherosclerosis, said method comprising administering to a patient diagnosed with or at substantial risk of developing atherosclerosis a therapeutically effective amount of an agent that substantially inhibits said patient's protease-activated receptor-1 (PAR-1) signaling activity that results from a proteolytic cleavage by matrix metalloprotease-1 (MMP-1) between aspartic acid at position 39 (D39) and proline at position 40 (P40) of said patient's protease-activated receptor-1 (PAR-1).

17. The method of claim 16, administered after at least a procedure selected from the group consisting of an angioplasty procedure, a coronary bypass procedure, and an open-heart surgery has been performed on said patient.

18. The method of claim 16, administered for no more than two weeks on said patient.

19. The method of claim 16, wherein said agent comprises a pepducin lipopeptide of a PAR family member.

20. The method of claim 19, wherein said pepducin lipopeptide of a PAR family member comprises a PAR-1 pepducin lipopeptide.

21. The method of claim 20, wherein said PAR-1 pepducin lipopeptide is selected from the group consisting of Plip3pal-7, Pli3pal-12, Pli3pal-12S, Pli3pal-10S, Pli1pal-11, Pli2pal-7, Pli2pal-11, Pli2pal-16, Pli2pal-21, P1i4pal13 and P1i4pal13R.

22. The method of claim 16, wherein said agent reduces the size of atherosclerotic plaque within the aorta of said patient.

* * * * *